(12) United States Patent
Liu et al.

(10) Patent No.: US 11,332,492 B2
(45) Date of Patent: May 17, 2022

(54) CD73 INHIBITORS AND THERAPEUTIC USES THEREOF

(71) Applicants: Jiangsu Hengrui Medicine Co., Ltd., Lianyungang (CN); Shanghai Hengrui Pharmaceutical Co., Ltd., Shanghai (CN)

(72) Inventors: Jian Liu, Edison, NJ (US); Heping Wu, Edison, NJ (US); Linghang Zhuang, Chalfont, PA (US); Suxing Liu, Edison, NJ (US); Rumin Zhang, Edison, NJ (US); Feng He, Shanghai (CN); Weikang Tao, North Brunswick, NJ (US)

(73) Assignees: Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 17/270,806

(22) PCT Filed: Aug. 28, 2019

(86) PCT No.: PCT/US2019/048552
§ 371 (c)(1),
(2) Date: Feb. 23, 2021

(87) PCT Pub. No.: WO2020/047082
PCT Pub. Date: Mar. 5, 2020

(65) Prior Publication Data
US 2021/0253621 A1  Aug. 19, 2021

Related U.S. Application Data

(60) Provisional application No. 62/723,623, filed on Aug. 28, 2018.

(51) Int. Cl.
*C07H 19/04* (2006.01)
*C07H 19/16* (2006.01)

(52) U.S. Cl.
CPC ............ *C07H 19/04* (2013.01); *C07H 19/16* (2013.01)

(58) Field of Classification Search
None
See application file for complete search history.

(56) References Cited

U.S. PATENT DOCUMENTS

| | | |
|---|---|---|
| 2004/0023901 A1 | 2/2004 | Cook et al. |
| 2010/0104532 A1 | 4/2010 | Chen et al. |
| 2017/0044203 A1* | 2/2017 | Cacatian ............ C07D 239/72 |

FOREIGN PATENT DOCUMENTS

| | | |
|---|---|---|
| WO | 2015164573 A1 | 10/2015 |
| WO | 2017098421 A1 | 6/2017 |
| WO | 2017120508 A1 | 7/2017 |
| WO | 2017153952 A1 | 9/2017 |
| WO | 2018049145 A1 | 3/2018 |
| WO | 2018067424 A1 | 4/2018 |
| WO | 2018094148 A1 | 5/2018 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Antonioli, L., et al., Trends Mol. Med., 2013, 19, 355-367.
Colgan, S.P., et al., Purinergic Signaling, 2006, 2, 351-360.
Dunwiddie, T.V., et al., Annu. Rev. Neurosci. 2001, 24, 31-55.
Pauwels, R., et al., Drug Development Research, 1993, 28, 318-321.
Hasko, G., et al., "A Key Link between Metabolism and Brain Activity", 2013, 233-251.
Antonioli, L. et al., Trends in Cancer, 2016, 2(2), 95-109.
Allard, D., et al., Immunotherapy, 2016, 8(2), 145-163.
Yang, Q., et al., Pathol. Oncol. Res., 2013, 19, 811-814.
Loi, S., et al., PNAS, 2013, 110(27), 11091-11096.
Antonioli, L., et al., Nature Reviews Cancer, 2013, 13, 842-857.

* cited by examiner

Primary Examiner — Traviss C McIntosh, III
(74) Attorney, Agent, or Firm — Fox Rothschild LLP

(57) ABSTRACT

This application discloses CD73 inhibitors represented by the general formula (I) and analogs thereof, pharmaceutical compositions containing these compounds, methods of preparing them, and use of these compounds as therapeutic agents for the treatment of diseases or conditions associated with CD73 activity, such as various cancers.

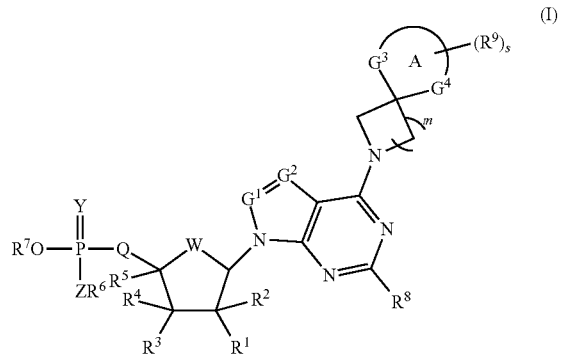

23 Claims, No Drawings

CD73 INHIBITORS AND THERAPEUTIC USES THEREOF

CROSS-REFERENCE TO RELATED APPLICATIONS

This application is a U.S. national phase application of International Application No. PCT/US2019/048552, filed on Aug. 28, 2019, which claims priority under 35 U.S.C. § 119(e) to United States Provisional Patent Application No. 62/723,623, filed on Aug. 28, 2018, the disclosures of which are incorporated herein by reference in their entirety.

FIELD OF THE INVENTION

The present invention relates to novel nucleoside and nucleotide analogs, pharmaceutical compositions containing these compounds useful as CD73 inhibitors for the treatment of cancer and other diseases mediated by CD73, and methods of preparing these compounds and compositions.

BACKGROUND OF THE INVENTION

CD73 (also known as ecto-5'-nucleotidase) is a cell surface enzyme through a glycosyl phosphatidylinositol linkage to anchor onto the cell membrane and is expressed in different tissues, especially in the colon, kidney, brain, liver, heart, lung, spleen, lymph nodes, and bone marrow (Antonioli, L., et al., *Trends Mol. Med.*, 2013, 19, 355-367). The enzymatic activity of CD73 is to catalyze the extracellular dephosphorylation of nucleoside monophosphates to their corresponding nucleosides (e.g., 5-AMP to adenosine). CD73 exerts physiological influences mainly via its enzymatic nucleoside products, particularly adenosine in extracellular space, including epithelial ion and fluid transportation, tissue barrier function control, adaptation to hypoxia, ischemic preconditioning, anti-inflammation, and immune suppression signaling (Colgan, S. P., et al., *Purinergic Signaling*, 2006, 2, 351-360).

As a ubiquitous extracellular signaling molecule with neuromodulating properties, adenosine produces a broad range of physiological responses in the human body via interaction with adenosine receptors (receptor subtypes: A1, A2A, A2B, and A3), including the vasodilation and atrioventricular conduction suppression properties in the cardiovascular system; the sedative, local neuronal excitability inhibition, anticonvulsant, and neuroprotective effects in the central nervous system (Dunwiddie, T. V., et al., *Annu. Rev. Neurosci.* 2001, 24, 31-55); the bronchoconstriction effects in the respiratory system (Pauwels, R., et al., *Drug Development Research*, 1993, 28, 318-321); and the mediation of immune/inflammatory responses in the immune system (Hasko, G., et al., "A Key Link between Metabolism and Brain Activity", 2013, 233-251).

CD73 is broadly expressed in many cancer types (Antonioli, L. et al., *Trends in Cancer*, 2016, 2(2), 95-109) and associated with many cancer types' poor prognosis (Allard, D., et al., *Immunotherapy*, 2016, 8(2), 145-163). CD73 promotes cancer metastasis (Yang, Q., et al., *Pathol. Oncol. Res.*, 2013, 19, 811-814) and chemoresistance (Loi, S., et al., *PNAS*, 2013, 110(27), 11091-11096). In the immune system, CD73 is found on the surface of macrophages, lymphocytes, regulatory T cells, myeloid-derived suppressor cells (MDSCs), and dendritic cells. The extracellular adenosine, mainly produced by CD73, can chronically accumulate in tumor microenvironment, activating adenosine receptors, promoting tumor-inducing mononuclear phagocytes, deregulating anti-tumor T cell response, expanding MDSCs population, triggering immune suppression and favoring the escape of cancer cells from immune surveillance, hence promoting cancer transformation and growth (Antonioli, L., et al., *Nature Reviews Cancer*, 2013, 13, 842-857).

Because of a wide range of physiological functions of adenosine in human body, CD73 inhibitors can be used to enhance immune response and treat adenosine and adenosine receptor related diseases or disorders, including neurological, neurodegenerative and CNS disorders and diseases, depression and Parkinson's disease, cerebral and cardiac ischaemic diseases, sleep disorders, fibrosis, immune and inflammatory disease, and cancer.

Although various small-molecule CD73 inhibitors have been disclosed in several published patent applications, such as WO2015164573, WO2017098421, WO2017120508, WO2017153952, US20170044203, WO2018049145, WO2018067424, and WO2018094148, only one compound has been reported to be in phase I clinical study. Therefore, there is still an urgent need to develop new CD73 inhibitors that are therapeutically useful in limiting tumor progression and metastasis, increasing the efficacy of anti-cancer therapy, and/or treating cancers by decreasing extracellular adenosine level in tumor microenvironments to resume effective responses of immune cells against cancer cells.

SUMMARY OF THE INVENTION

The present invention meets the foregoing need and, in one aspect, provides a compound of formula (I), or a tautomer, mesomer, racemate, enantiomer, diastereomer thereof, or mixture thereof, or a pharmaceutically acceptable salt, solvate or prodrug thereof:

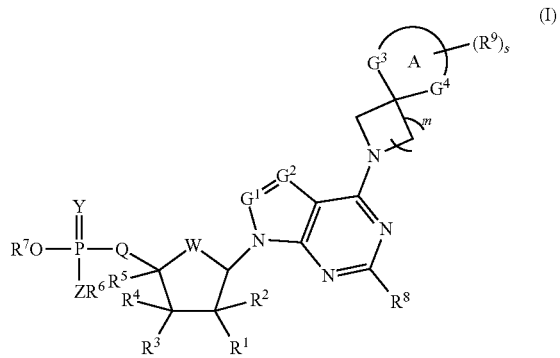

wherein:

Y is O or S;

Z is O or NH;

W is selected from the group consisting of O, S, NH, $NR^a$ and $C(R^b)_2$, wherein $R^a$ is alkyl, and $R^b$ at each occurrence is independently selected from the group consisting of hydrogen, halogen, alkyl and alkenyl;

$G^1$ and $G^2$ are each independently N or $CR^c$, wherein $R^c$ is selected from the group consisting of hydrogen, halogen, alkyl, alkoxy, hydroxy, amino, nitro, cyano, cycloalkyl, heterocyclyl, aryl and heteroaryl;

$G^3$ and $G^4$ are each independently selected from the group consisting of C, CH, $CH_2$, N, NH, O, S and $SO_2$;

Q is selected from the group consisting of —$CH_2$—O—$C(R^s)(R^r)$—, —$CH_2$—$N(R^m)$—$C(R^s)(R^r)$—, —$CH_2$—S—$C(R^s)(R^r)$—, —$CH_2$—$S(O)_2$—$C(R^s)(R^r)$—, -phenyl-O—$C(R^s)(R^r)$—, —$CH_2$-phenyl-O—$C(R^s)(R^r)$—, —$CH_2$- heterocyclyl-, —C(R′′′)(R″), —CH₂—C(R′′′)(R″)—C(Rˢ)(Rᵗ)—, —C(Rˢ)=C(Rᵗ)—, —C(R′′′)(R″)—C(Rˢ)(Rᵗ)—, —C(R′′′)(R″)—C(Rˢ)=C(Rᵗ)— and —C(Rˢ)=C(Rᵗ)—C(R′′′)(R″);

Rˢ, Rᵗ, R′′′ and R″ are each independently selected from the group consisting of H, D, halogen, alkyl, alkoxy, haloalkyl, haloalkoxy, hydroxy, hydroxyalkyl and amino;

or Rˢ and Rᵗ in any —C(Rˢ)(Rᵗ)— are taken together to form oxo;

or R′′′ and R″ are taken together to form oxo;

ring A is selected from the group consisting of C₅₋₈cycloalkyl, 5 to 8-member heterocyclyl, aryl fused C₅₋₈cycloalkyl, heteroaryl fused C₅₋₈cycloalkyl, aryl fused 5 to 8-member heterocyclyl, heteroaryl fused 5 to 8-member heterocyclyl;

R¹, R², R³ and R⁴ are each independently selected from the group consisting of hydroxy, hydrogen, halogen, alkyl, alkoxy, haloalkyl, hydroxyalkyl, cyano, amino, azide group and OR¹⁰;

or R¹ and R² together with the carbon atom they attached to form a cycloalkyl or heterocyclyl, wherein the heterocyclyl contains 1 to 2 heteroatoms which are the same or different from N, O and S, and wherein the cycloalkyl and heterocyclyl are each optionally substituted by one or more groups selected from the group consisting of halogen, alkyl, alkoxy, haloalkyl, haloalkoxy, hydroxy, hydroxyalkyl, cyano, amino, nitro, cycloalkyl and heterocyclyl;

R⁵ is selected from the group consisting of hydrogen, halogen, alkyl, alkenyl, alkynyl, alkoxy, haloalkyl, haloalkoxy, hydroxy, hydroxyalkyl, cyano, amino, nitro and azide;

R⁶ and R⁷ are each independently selected from the group consisting of hydrogen, alkyl, aryl, —C(R′′′R″)-aryl, —C(R′′′R″)—O—C(O)ORᵈ, —C(R′′′R″)—O—C(O)Rᵈ, —C(R′′′R″)C(O)ORᵈ, cycloalkyl, heterocyclyl, aryl and heteroaryl, wherein the alkyl is optionally substituted by one or more groups selected from the group consisting of cycloalkyl, heterocyclyl, aryl and heteroaryl; optionally, R⁶ and R⁷ are combined to form a 5- to 6-membered heterocyclic ring;

Rᵈ is selected from the group consisting of hydrogen, alkyl and alkoxy;

R⁸ is selected from the group consisting of hydrogen, halogen, alkyl, alkenyl, alkynyl, alkoxy, haloalkyl, haloalkoxy, hydroxy, hydroxyalkyl, cyano, amino, nitro, azide, cycloalkyl and heterocyclyl;

R⁹ is selected from the group consisting of hydrogen, halogen, alkyl, alkenyl, alkynyl, alkoxy, haloalkyl, haloalkoxy, hydroxy, hydroxyalkyl, cyano, amino, nitro, azide, cycloalkyl and heterocyclyl;

R¹⁰ is selected from the group consisting of —C(O)R¹¹, —C(O)OR¹¹, —S(O)₂R¹¹, and —P(O)(OR⁶)(OR⁷);

R¹¹ is selected from the group consisting of hydrogen, halogen, alkyl, haloalkyl, hydroxyl and hydroxyalkyl;

m is 1, 2 or 3; and s is 0, 1, 2, 3 or 4.

In another aspect, the invention provides pharmaceutical compositions comprising a therapeutically effective amount of a compound of the formula (I), or a pharmaceutically acceptable salt, solvate, or prodrug thereof, and one or more pharmaceutically acceptable carriers, diluents, and/or other excipients.

In another aspect, the invention provides methods and processes, as well as intermediate compounds, for preparing the compounds of formula (I), or a pharmaceutically acceptable salt, solvate, or prodrug thereof.

In another aspect, this invention provides a method of treating a CD73-mediated disease or condition, especially various cancers, comprising administering to a subject in need thereof a therapeutically effective amount of a compound of the formula (I), or a pharmaceutically acceptable salt, solvate, prodrug, or pharmaceutical composition thereof.

In another aspect, the invention provides a method of inhibiting CD73, comprising contacting a biological sample containing CD73 with a compound of the formula (I), or a pharmaceutically acceptable salt, solvate, or prodrug thereof.

In another aspect, the invention provides use of a compound of the formula (I), or a pharmaceutically acceptable salt, solvate, or prodrug thereof, in the manufacture of a medicament for treating a CD73-mediated disease or condition, especially various cancers.

Other aspects and benefits of the present invention will be better understood through the detailed description, Examples, and claims below.

DETAILED DESCRIPTION OF THE INVENTION

In one aspect, the present invention provides a compound of formula (I):

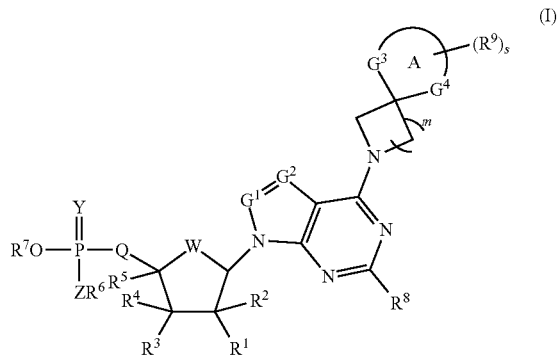

(I)

or a tautomer, mesomer, racemate, enantiomer, diastereomer thereof, or mixture thereof, or a pharmaceutically acceptable salt, solvate or prodrug thereof, wherein m, s, ring A, G¹ to G⁴, R¹ to R⁹, W, Y, and Z are as defined above.

In one embodiment of the invention, the compound of formula (I) is selected from a compound of formula (II):

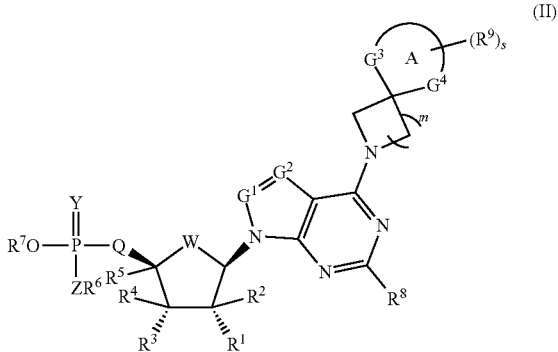

(II)

or a tautomer, mesomer, racemate, enantiomer, diastereomer thereof, or mixture thereof, or a pharmaceutically acceptable salt, solvate or prodrug thereof, wherein:

Z, Y, W, Q, $G^1$, $G^2$, $G^3$, $G^4$, ring A, $R^1$ to $R^9$, m and s are as defined in formula (I).

In one embodiment of the invention, the compound of formula (I) is selected from a compound of formula (III):

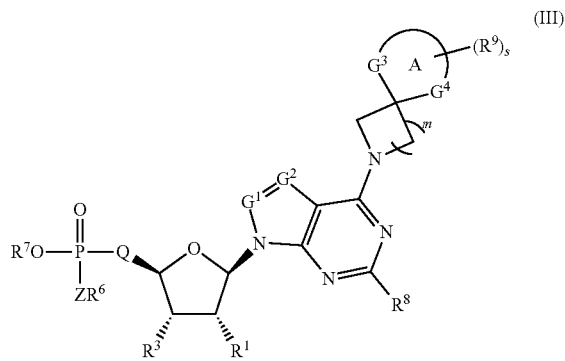

(III)

or a tautomer, mesomer, racemate, enantiomer, diastereomer thereof, or mixture thereof, or a pharmaceutically acceptable salt, solvate or prodrug thereof,
wherein:
Z, Q, $G^1$, $G^2$, $G^3$, $G^4$, ring A, $R^1$, $R^3$, $R^6$ to $R^9$, m and s are as defined in formula (I).

In one embodiment, the invention provides a compound of formula (I), or a tautomer, mesomer, racemate, enantiomer, diastereomer thereof, or mixture thereof, or a pharmaceutically acceptable salt, solvate or prodrug thereof, wherein Q is selected from the group consisting of —CH$_2$—O—C(R$^s$)(R$^t$)—, —CH$_2$—NH—C(R$^s$)(R$^t$)—, —CH$_2$—S—C(R$^s$)(R$^t$)—, —CH$_2$S(O)$_2$—C(R$^s$)(R$^t$)—, -phenyl-O—C(R$^s$)(R$^t$)—, —CH$_2$-phenyl-O—C(R$^s$)(R$^t$)— and —CH$_2$-heterocyclyl-; R$^s$ and R$^t$ are as defined in formula (I).

In one embodiment, the invention provides a compound of formula (I), or a tautomer, mesomer, racemate, enantiomer, diastereomer thereof, or mixture thereof, or a pharmaceutically acceptable salt, solvate or prodrug thereof, wherein $R^2$ and $R^4$ are hydrogen; $R^1$ and $R^3$ are each independently selected from the group consisting of hydroxy, hydrogen, halogen, alkyl, alkoxy, haloalkyl, haloalkoxy and hydroxyalkyl.

In one embodiment of the invention, the compound of formula (I) is selected from a compound of formula (IV):

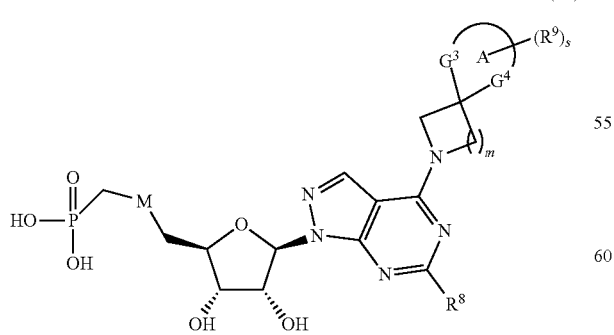

(IV)

or a tautomer, mesomer, racemate, enantiomer, diastereomer thereof, or mixture thereof, or a pharmaceutically acceptable salt, solvate or prodrug thereof, wherein:
M is selected from the group consisting of O, S, SO$_2$, NH and -phenyl-O; and
ring A, $G^3$, $G^4$, $R^8$, $R^9$, m and s are as defined in formula (I).

In one embodiment, the invention provides a compound of formula (I), or a tautomer, mesomer, racemate, enantiomer, diastereomer thereof, or mixture thereof, or a pharmaceutically acceptable salt, solvate or prodrug thereof,
wherein

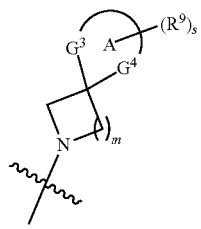

is selected from the group consisting of

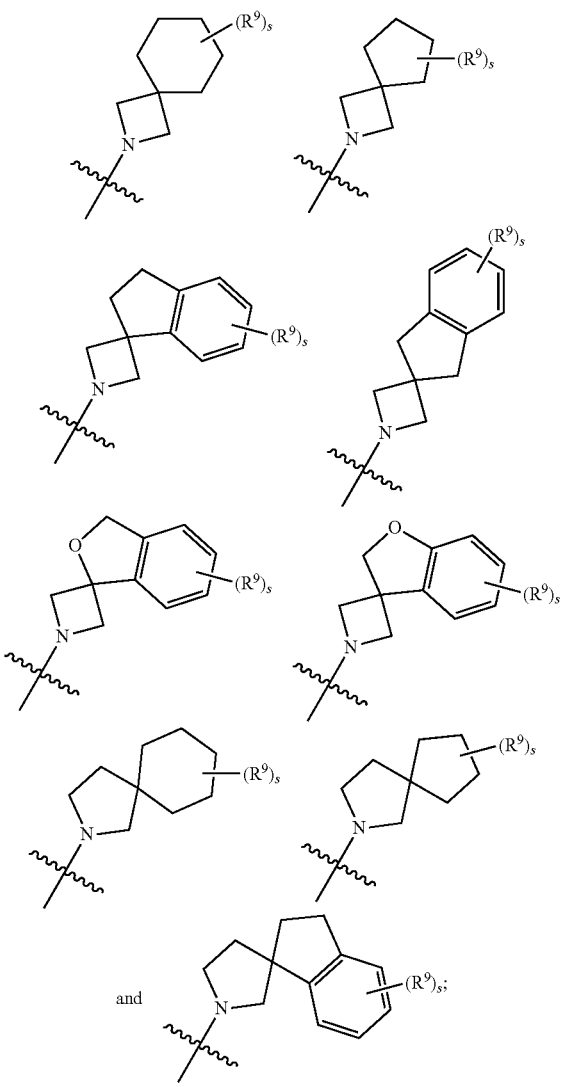

and and

R[9] and s are as defined in formula (I). In one embodiment, the invention provides a compound of formula (I), or a tautomer, mesomer, racemate, enantiomer, diastereomer thereof, or mixture thereof, or a pharmaceutically acceptable salt, solvate or prodrug thereof, wherein R[6] and R[7] are each independently selected from the group consisting of hydrogen, alkyl, and —C(R'''R'''')—O—C(O)OR[d].

In one embodiment, the invention provides a compound of formula (I), or a tautomer, mesomer, racemate, enantiomer, diastereomer thereof, or mixture thereof, or a pharmaceutically acceptable salt, solvate or prodrug thereof, wherein R[8] is selected from the group consisting of hydrogen, halogen, alkyl, alkoxy, haloalkyl and haloalkoxy.

In one embodiment, the invention provides a compound of formula (I), or a tautomer, mesomer, racemate, enantiomer, diastereomer thereof, or mixture thereof, or a pharmaceutically acceptable salt, solvate or prodrug thereof, wherein R[9] is selected from the group consisting of hydrogen, halogen, alkyl, alkoxy, haloalkyl and haloalkoxy.

In one embodiment, sometimes preferred, the present invention provides a compound of formula (V):

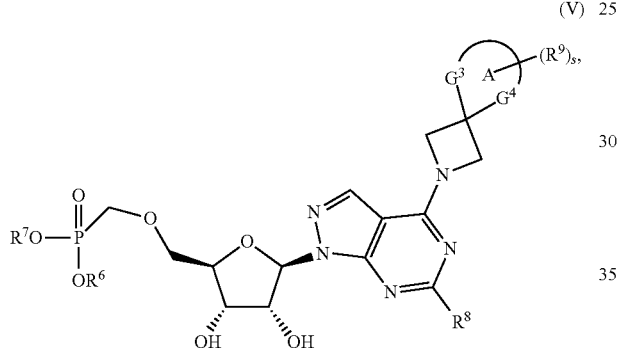

(V)

or a tautomer, enantiomer, diastereomer, or mixture thereof, or a pharmaceutically acceptable salt, solvate, or prodrug thereof, wherein: R[6] and R[7] are each independently selected from the group consisting of hydrogen, $C_1$-$C_6$ alkyl, $C_6$-$C_{10}$ aryl, —C(R'''R'''')-aryl, —C(R'''R'''')—O—C(O)OR[d], and —C(R'''R'''')—O—C(O)R[d], wherein the alkyl is optionally substituted by one or more groups selected from the group consisting of $C_3$-$C_6$ cycloalkyl, 5- to 10-membered heterocyclyl, $C_6$-$C_{10}$ aryl, and 5- to 10-membered heteroaryl;

R''' and R'''' are each independently selected from the group consisting of H, D, halogen, $C_1$-$C_4$ alkyl, $C_1$-$C_4$ alkoxy, $C_1$-$C_4$ haloalkyl, and $C_1$-$C_4$ haloalkoxy;

R[d] is $C_1$-$C_6$ alkyl;

R[8] is selected from the group consisting of hydrogen, halogen, and $C_1$-$C_4$ alkyl;

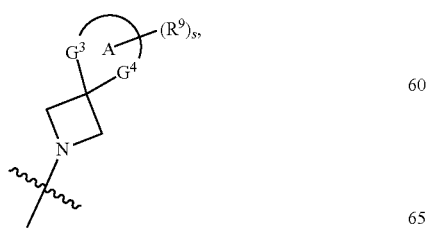

is selected from the group consisting of

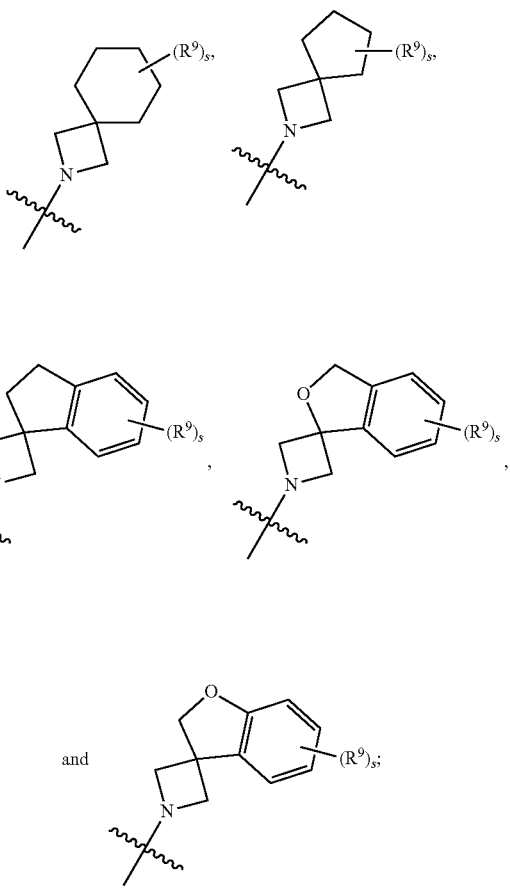

s is 0, 1, or 2; and

R[9] at each occurrence is independently selected from the group consisting of halogen, $C_1$-$C_4$ alkyl, $C_1$-$C_4$ alkoxy, $C_1$-$C_4$ haloalkyl, and $C_1$-$C_4$ haloalkoxy.

In some embodiments, sometimes more preferably, in the compound of formula (V), or a tautomer, enantiomer, diastereomer, or mixture thereof, or a pharmaceutically acceptable salt, solvate, or prodrug thereof:

R[6] and R[7] are each independently selected from the group consisting of hydrogen, $C_1$-$C_4$ alkyl, phenyl, —CH(R''')—O—C(O)OR[d], and —CH(R''')—O—C(O)R[d];

R''' is H, D, or $C_1$-$C_4$ alkyl;

R[d] is $C_1$-$C_6$ alkyl;

R[8] is hydrogen or halogen;

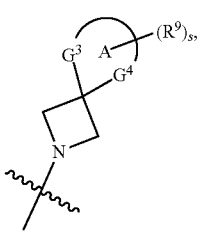

is selected from the group consisting of

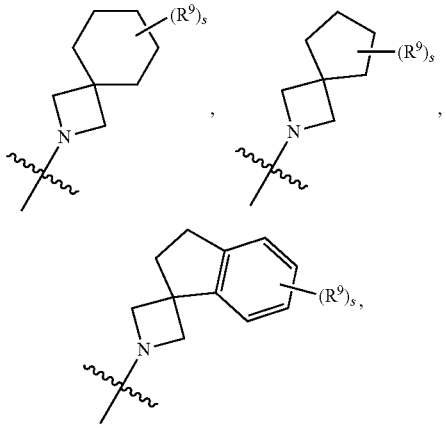

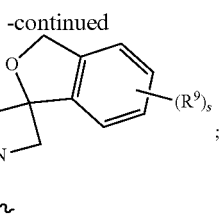 and 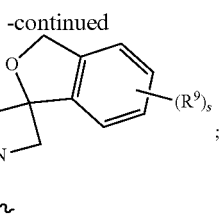 ;

s is 0, 1, or 2; and
$R^9$ at each occurrence is independently selected from the group consisting of halogen, $C_1$-$C_4$ alkyl, and $C_1$-$C_4$ alkoxy.

In other embodiments, as a person of skill in the art would understand, the present invention encompasses any and all plausible combinations of the exemplified embodiments with respect to the functional groups defined in any of the structure of formulas (I) to (V) described herein so long as such a combination forms a stable compound that does not violate chemical bonding principles.

Exemplified compounds of the invention include, but are not limited to:

| Example No. | Compound structure and name |
|---|---|
| 1 | 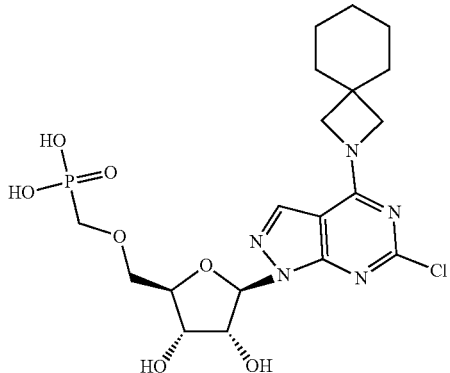 [SMILES: O=P(O)(O)COC[C@H]1O[C@@H](n2ncc3c(N4CC5(CCCCC5)C4)nc(Cl)nc32)[C@H](O)[C@@H]1O]<br>((((2R,3S,4R,5R)-5-(6-chloro-4-(2-azaspiro[3.5]nonan-2-yl)-1H-pyrazolo[3,4-d]pyrimidin-1-yl)-3,4-dihydroxytetrahydrofuran-2-yl)methoxy)methyl)phosphonic acid 1 |
| 2 | 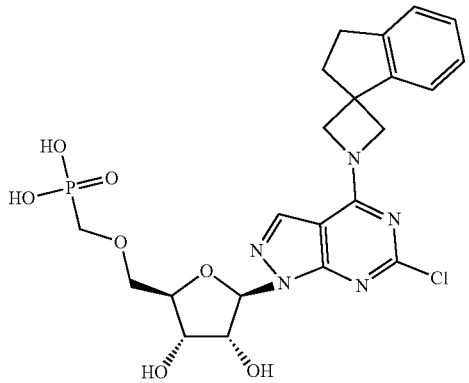 [SMILES: O=P(O)(O)COC[C@H]1O[C@@H](n2ncc3c(N4CC5(CCc6ccccc65)C4)nc(Cl)nc32)[C@H](O)[C@@H]1O]<br>((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 2 |

-continued

| Example No. | Compound structure and name |
|---|---|
| 3 | 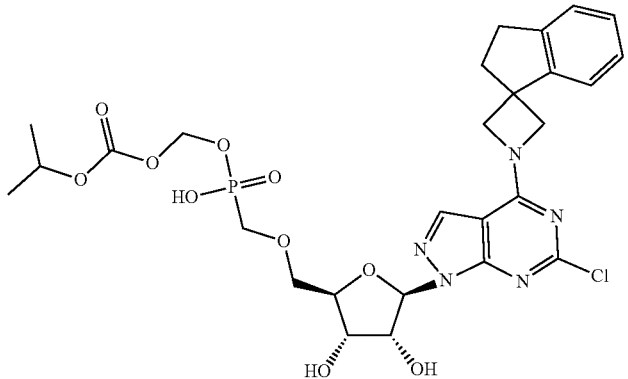<br>3<br>((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4- |
| 4 | 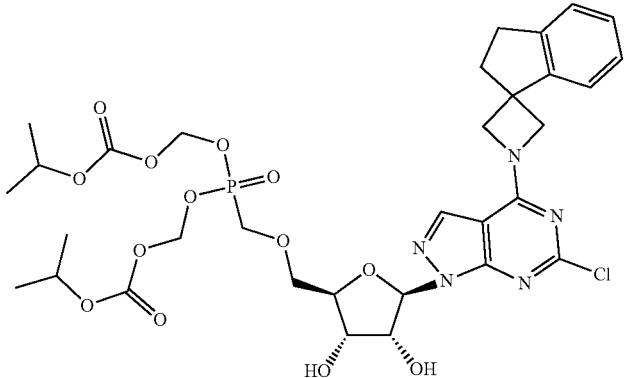 [SMILES: CC(C)OC(=O)OCOP(=O)(COC[C@H]1O[C@@H](n2ncc3c(N4CC5(CCc6ccccc65)C4)nc(Cl)nc32)[C@H](O)[C@@H]1O)OCOC(=O)OC(C)C]<br>4<br>((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphoryl)bis(oxy))bis(methylene) diisopropyl decarbonate 4 |
| 5 | 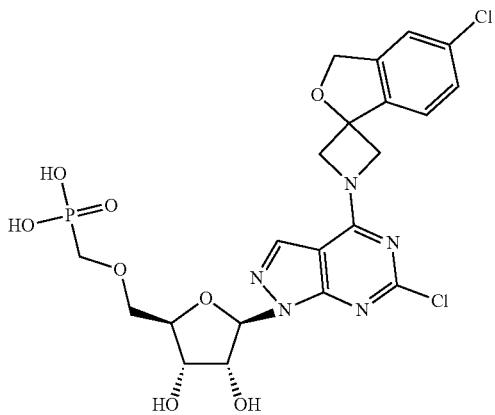 [SMILES: O=P(O)(O)COC[C@H]1O[C@@H](n2ncc3c(N4CC5(C4)OCc4cc(Cl)ccc45)nc(Cl)nc32)[C@H](O)[C@@H]1O]<br>5<br>(((((2R,3S,4R,5R)-5-(6-chloro-4-(5'-chloro-3'H-spiro[azetidine-3,1'-isobenzofuran]-1-yl)-1H-pyrazolo[3,4-d]pyrimidin-1-yl)-3,4-dihydroxytetrahydrofuran-2-yl)methoxy)methyl)phosphonic acid 5 |

| Example No. | Compound structure and name |
|---|---|
| 6 | 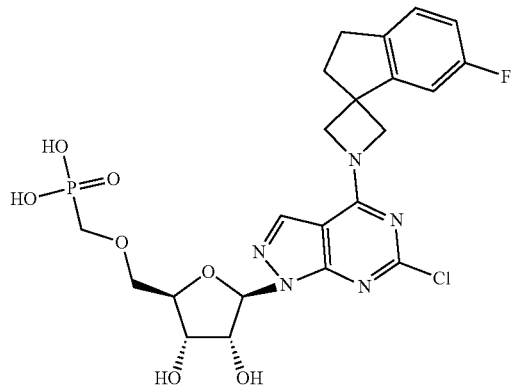 [SMILES: O=P(O)(O)COC[C@H]1O[C@@H](n2ncc3c(N4CC5(CCc6ccc(F)cc65)C4)nc(Cl)nc32)[C@H](O)[C@@H]1O]<br>((((2R,3S,4R,5R)-5-(6-chloro-4-(6'-fluoro-2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 6 |
| 7 | 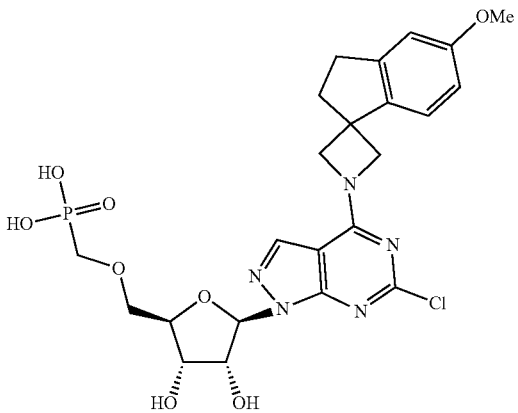 [SMILES: COc1ccc2c(c1)CCC21CN(c2nc(Cl)nc3c2cnn3[C@@H]2O[C@H](COCP(=O)(O)O)[C@@H](O)[C@H]2O)C1]<br>((((2R,3S,4R,5R)-5-(6-chloro-4-(5'-methoxy-2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 7 |

| Example No. | Compound structure and name |
|---|---|
| 8 | 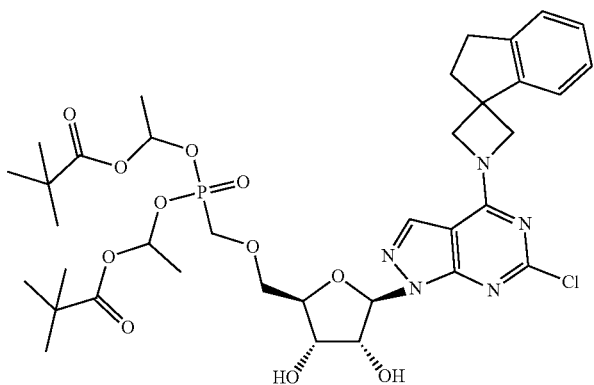 [SMILES: CC(OC(=O)C(C)(C)C)OP(=O)(COC[C@H]1O[C@@H](n2ncc3c(N4CC5(CCc6ccccc65)C4)nc(Cl)nc32)[C@H](O)[C@@H]1O)OC(C)OC(=O)C(C)(C)C]<br>8<br><br>((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphoryl)bis(oxy))bis(ethane-1,1-diyl) bis(2,2-dimethylpropanoate) 8 |
| 9 | 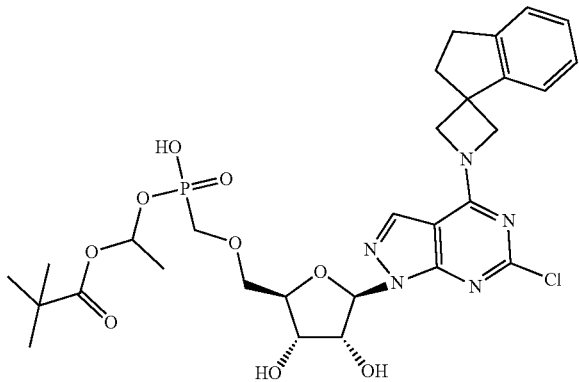 [SMILES: CC(OC(=O)C(C)(C)C)OP(=O)(O)COC[C@H]1O[C@@H](n2ncc3c(N4CC5(CCc6ccccc65)C4)nc(Cl)nc32)[C@H](O)[C@@H]1O]<br>9<br><br>1-((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)(hydroxy)phosphoryl)oxy)ethyl pivalate 9 |

| Example No. | Compound structure and name |
|---|---|
| 10 | 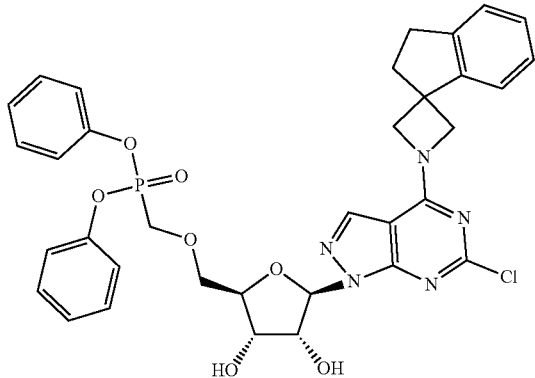 [SMILES: O=P(COC[C@H]1O[C@@H](n2ncc3c(N4CC5(CCc6ccccc65)C4)nc(Cl)nc32)[C@H](O)[C@@H]1O)(Oc1ccccc1)Oc1ccccc1]

diphenyl (((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonate 10 |
| 11 | 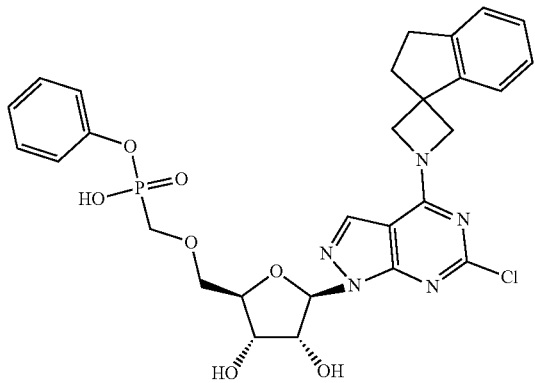 [SMILES: O=P(O)(COC[C@H]1O[C@@H](n2ncc3c(N4CC5(CCc6ccccc65)C4)nc(Cl)nc32)[C@H](O)[C@@H]1O)Oc1ccccc1]

phenyl hydrogen (((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonate 11 |
| 12 | 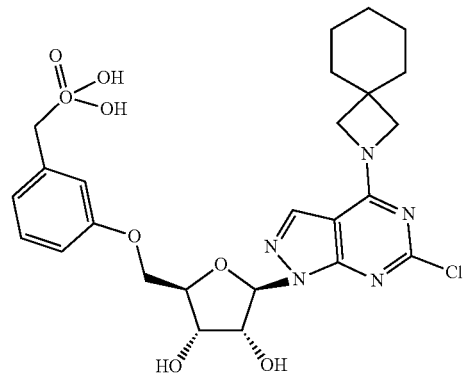

(3-(((2R,3S,4R,5R)-5-(6-chloro-4-(2-azaspiro[3.5]nonan-2-yl)-1H-pyrazolo[3,4-d]pyrimidin-1-yl)-3,4-dihydroxytetrahydrofuran-2-yl)methoxy)benzyl)phosphonic acid 12 |

In another aspect, this invention provides a compound of formula (IA), used as an intermediate for preparing a compound of formula (I):

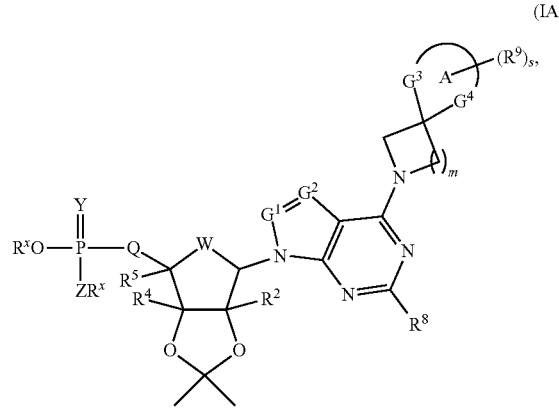

(IA)

or a tautomer, mesomer, racemate, enantiomer, diastereomer thereof, or mixture thereof, or a pharmaceutically acceptable salt, solvate or prodrug thereof, wherein:

Z is O;

$R^x$ is alkyl;

Y, W, Q, $G^1$, $G^2$, $G^3$, $G^4$, ring A, $R^2$, $R^4$, $R^5$, $R^8$, $R^9$, m and s are as defined in formula (I).

In one embodiment of the invention, the compound of formula (IA) is selected from a compound of formula (IVA):

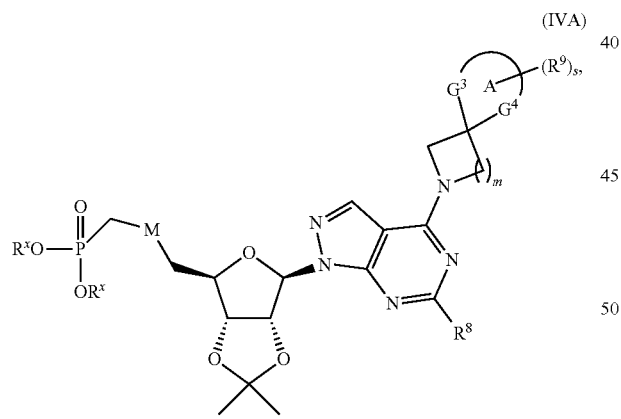

(IVA)

or a tautomer, mesomer, racemate, enantiomer, diastereomer thereof, or mixture thereof, or a pharmaceutically acceptable salt, solvate or prodrug thereof, wherein:

$R^x$ is alkyl;

M is O; and ring A, $G^3$, $G^4$, $R^8$, $R^9$, m and s are as defined in formula (IA).

Exemplified compounds of the invention include, but are not limited to:

| Example No. | Compound structure and name |
|---|---|
| 1f | 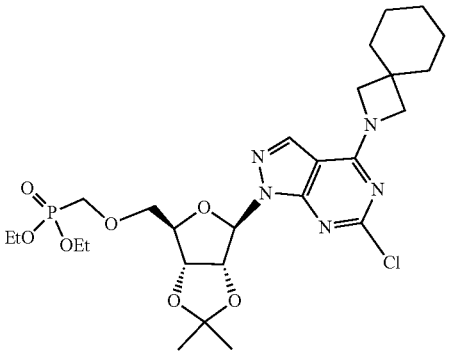 [SMILES: CCOP(=O)(COC[C@H]1O[C@@H](n2ncc3c(N4CC5(CCCCC5)C4)nc(Cl)nc32)[C@@H]2OC(C)(C)O[C@@H]21)OCC]<br>1f |
| 2j | 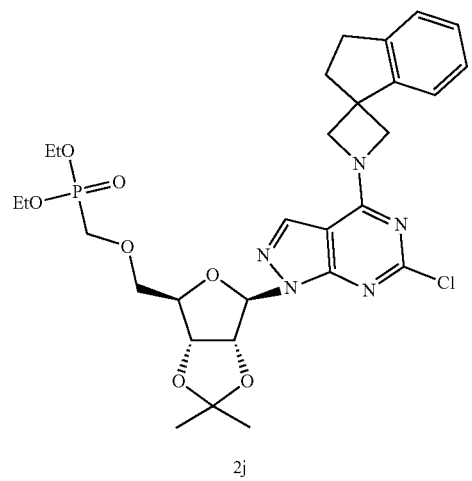<br>2j |
| 5j | 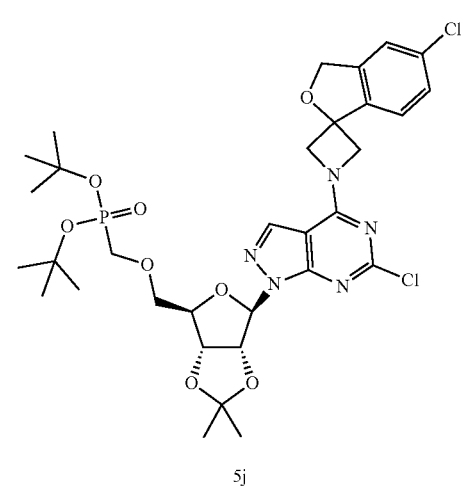<br>5j |

| Example No. | Compound structure and name |
|---|---|
| 6n | 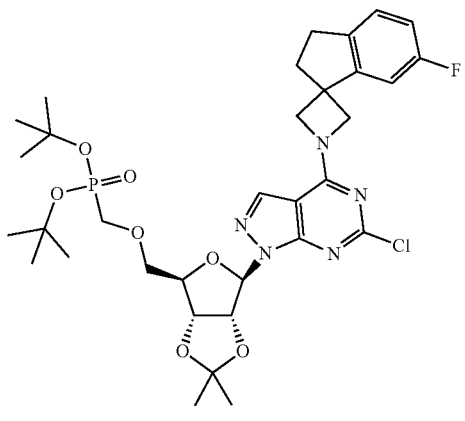 [SMILES: CC(C)(C)OP(=O)(COC[C@H]1O[C@@H](n2ncc3c(N4CC5(CCc6ccc(F)cc65)C4)nc(Cl)nc32)[C@@H]2OC(C)(C)O[C@@H]21)OC(C)(C)C]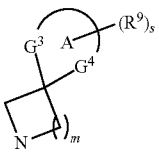<br>6n |
| 12d | 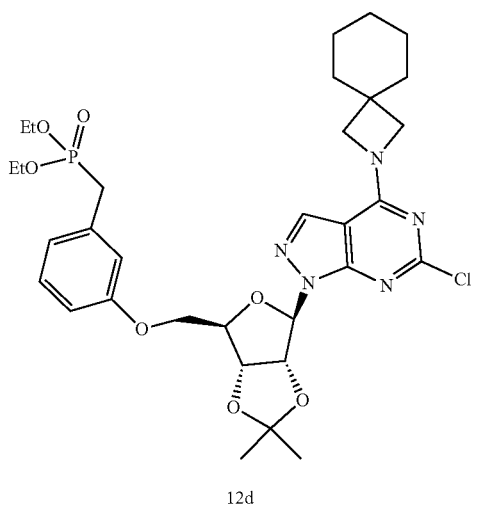<br>12d |

In another aspect, this invention provides a process for preparing a compound of formula (I), or a tautomer, mesomer, racemate, enantiomer, diastereomer, or mixture thereof, or a pharmaceutically acceptable salt thereof, the preparation process comprising the steps of:

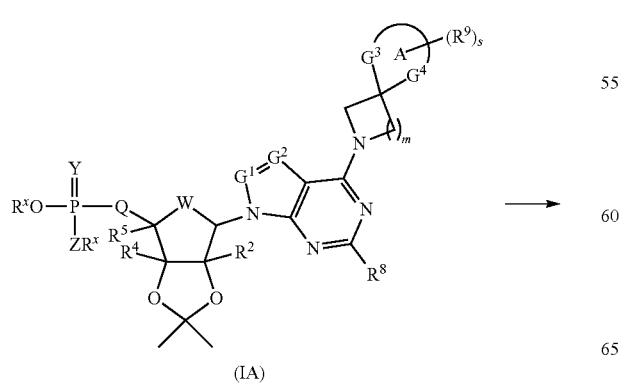

(IA)

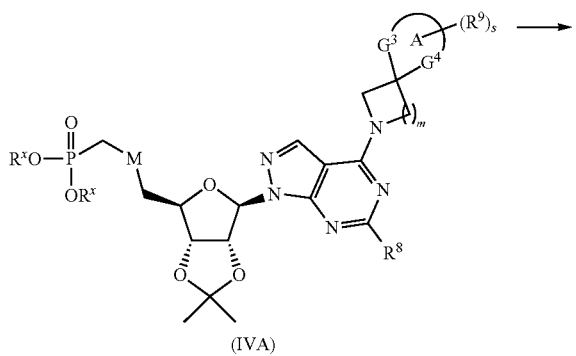

(I)

reacting to remove the protecting group of $R^x$ and acetal from a compound of formula (IA) to obtain the compound of formula (I);

wherein:

$R^x$ is alkyl;

Z is O;

$R^6$ and $R^7$ are both hydrogen; and $R^1$ and $R^3$ are both hydroxy;

Y, W, Q, $G^1$, $G^2$, $G^3$, $G^4$, ring A, $R^2$, $R^4$, $R^5$, $R^8$, $R^9$, m and s are as defined in formula (I).

In another aspect, this invention provides a process for preparing a compound of formula (IV), or a tautomer, mesomer, racemate, enantiomer, diastereomer, or mixture thereof, or a pharmaceutically acceptable salt thereof, the preparation process comprising the steps of:

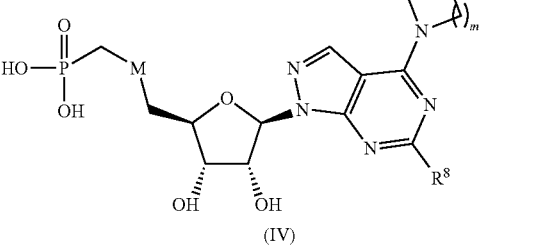

(IVA)

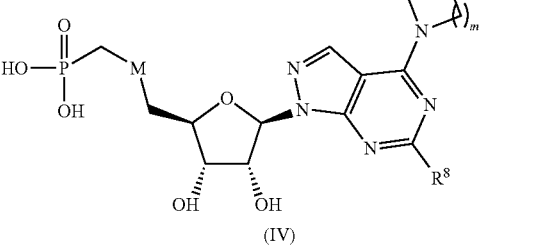

(IV)

reacting to remove the protecting group of $R^x$ and acetal from a compound of formula (IVA) to obtain a compound of formula (IV);

wherein:

$R^x$ is alkyl;

M is O; and ring A, $G^3$, $G^4$, $R^8$, $R^9$, m and s are as defined in formula (IV).

The present invention also provides a pharmaceutical composition, comprising a therapeutically effective amount of a compound of any one of formulas (I) to (V), or a tautomer, mesomer, racemate, enantiomer, diastereomer, or mixture thereof, or a pharmaceutically acceptable salt, solvate or prodrug thereof, together with one or more pharmaceutically acceptable carriers, diluents or excipients.

The present invention also relates to a method for inhibiting CD73, comprising contacting a biological sample comprising CD73 with a compound of any one of formulas (I) to (V), or a tautomer, mesomer, racemate, enantiomer, diastereomer, or mixture thereof, or a pharmaceutically acceptable salt, solvate or prodrug thereof, or a pharmaceutical composition thereof.

The present invention also relates to a method for treating a CD73-mediated disease or condition, comprising a step of administering to a subject in need thereof a therapeutically effective amount of a compound of any one of formulas (I) to (V), or a tautomer, mesomer, racemate, enantiomer, diastereomer, or mixture thereof, or a pharmaceutically acceptable salt, solvate or prodrug thereof, or a pharmaceutical composition thereof.

The present invention also relates to a method for treating a disease or condition, comprising administering to a subject in need thereof a therapeutically effective amount of the compound of any one of formulas (I) to (V), or a tautomer, mesomer, racemate, enantiomer, diastereomer, or mixture thereof, or a pharmaceutically acceptable salt, solvate or prodrug thereof, or a pharmaceutical composition thereof, wherein the disease or condition is selected from the group consisting of tumor, cancer, immune-related disease, inflammatory-related diseases, nervous system, neurodegenerative and central nervous system diseases, depression, Parkinson's disease, ischemic diseases of the brain and heart, sleep disorders and fibrosis.

The cancer is selected from the group consisting of melanoma, brain tumor, esophageal cancer, gastric cancer, liver cancer, pancreatic cancer, colorectal cancer, lung cancer, kidney cancer, breast cancer, ovarian cancer, metrocarcinoma, endometriosis, prostate cancer, skin cancer, neuroblastoma, sarcoma, osteochondroma, osteoma, osteosarcoma, seminoma, testicular tumor, uterine cancer, head and neck cancer, multiple myeloma, lymphoma, polycythemia vera, leukemia, thyroid tumor, ureteral tumor, bladder cancer, gallbladder cancer, cholangiocarcinoma, chorionic epithelial cancer, and pediatric tumor.

In another aspect, the present invention also relates to use of a compound of any one of formulas (I) to (V), or a tautomer, mesomer, racemate, enantiomer, diastereomer, or mixture thereof, or a pharmaceutically acceptable salt, solvate or prodrug thereof, or a pharmaceutical composition thereof, in the preparation of a medicament for treating a CD73-mediated disease or condition.

The CD73-mediated disease or condition includes, but is not limited to, tumor, cancer, immune-related disease, inflammatory-related diseases, nervous system, neurodegenerative and central nervous system diseases, depression, Parkinson's disease, ischemic diseases of the brain and heart, sleep disorders and fibrosis.

The compositions of this invention can be formulated by conventional methods using one or more pharmaceutically acceptable carriers. Thus, the active compounds of this invention can be formulated as various dosage forms for oral, buccal, intranasal, parenteral (e.g., intravenous, intramuscular or subcutaneous), rectal administration, inhalation or insufflation administration. The compounds of this invention can also be formulated as sustained release dosage forms.

Suitable dosage forms include, but are not limited to, a tablet, troche, lozenge, aqueous or oily suspension, dispersible powder or granule, emulsion, hard or soft capsule, or syrup or elixir. Oral compositions can be prepared according to any known method in the art for the preparation of pharmaceutical compositions. Such compositions can contain one or more additives selected from the group consisting of sweeteners, flavoring agents, colorants and preservatives, in order to provide a pleasing and palatable pharmaceutical preparation. Tablets contain the active ingredient and nontoxic pharmaceutically acceptable excipients suitable for the manufacture of tablets. These excipients can be inert excipients, granulating agents, disintegrating agents, and lubricants. The tablet can be uncoated or coated by means of a known technique to mask the taste of the drug or delay the disintegration and absorption of the drug in the gastrointestinal tract, thereby providing sustained release over an extended period. For example, water soluble taste masking materials can be used.

Oral formulations can also be provided as soft gelatin capsules in which the active ingredient is mixed with an inert solid diluent, or the active ingredient is mixed with a water soluble carrier.

An aqueous suspension contains the active ingredient in admixture with excipients suitable for the manufacture of an aqueous suspension. Such excipients are suspending agents, dispersants or humectants, and can be naturally occurring phospholipids. The aqueous suspension can also contain one or more preservatives, one or more colorants, one or more flavoring agents, and one or more sweeteners.

An oil suspension can be formulated by suspending the active ingredient in a vegetable oil, or in a mineral oil. The oil suspension can contain a thickener. The aforementioned sweeteners and flavoring agents can be added to provide a palatable preparation. These compositions can be preserved by adding an antioxidant.

The active ingredient and the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions can be preserved by adding an antioxidant such as ascorbic acid.

The present pharmaceutical composition can also be in the form of an oil-in-water emulsion. The oil phase can be a vegetable oil, or a mineral oil, or mixture thereof. Suitable emulsifying agents can be naturally occurring phospholipids. Sweeteners can be used. Such formulations can also contain moderators, preservatives, colorants and antioxidants.

The pharmaceutical composition can be in the form of a sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. The injectable solution or microemulsion can be introduced into an individual's bloodstream by local bolus injection. Alternatively, it can be advantageous to administer the solution or microemulsion in such a way as to maintain a constant circulating concentration of the present compound. In order to maintain such a constant concentration, a continuous intravenous delivery device can be utilized. An example of such a device is Deltec CADD-PLUS™5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, sterile fixed oils can easily be used as a solvent or suspending medium, and fatty acids can also be used to prepare injections.

The present compound can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

For buccal administration, the compositions can be formulated as tablets or lozenges by conventional means.

For intranasal administration or administration by inhalation, the active compounds of the present invention are conveniently delivered in the form of a solution or suspension released from a pump spray container that is squeezed or pumped by the patient, or as an aerosol spray released from a pressurized container or nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. The pressurized container or nebulizer can contain a solution or suspension of the active compound. Capsules or cartridges (for example, made from gelatin) for use in an inhaler or insufflator can be formulated containing a powder mix of the present invention and a suitable powder base such as lactose or starch.

It is well known to those skilled in the art that the dosage of a drug depends on a variety of factors, including but not limited to, the following factors: activity of the specific compound, age, weight, general health, behavior, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

Unless otherwise stated, the terms used in the specification and claims have the meanings described below.

"Alkyl" refers to a saturated aliphatic hydrocarbon group including C1-C20 straight chain and branched chain groups. Preferably an alkyl group is an alkyl having 1 to 12 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, preferably the substituent group(s) is one or more groups independently selected from the group consisting of alkyl, halogen, alkoxy, alkenyl, alkynyl, alkylsulfo, alkylamino, thiol, hydroxy, nitro, cyano, amino, cycloalkyl, heterocyclic alkyl, aryl, heteroaryl, cycloalkoxyl, heterocyclic, cycloalkylthio, heterocyclic alkylthio and oxo group.

"Alkenyl" refers to an alkyl defined as above that has at least two carbon atoms and at least one carbon-carbon double bond, for example, vinyl, 1-propenyl, 2-propenyl, 1-, 2-, or 3-butenyl, etc. preferably $C_{2-20}$ alkenyl, more preferably $C_{2-12}$ alkenyl, and most preferably $C_{2-6}$ alkenyl. The alkenyl group can be substituted or unsubstituted. When substituted, the substituent group(s) is preferably one or more group(s) independently selected from the group consisting of alkyl, halogen, alkoxy, alkenyl, alkynyl, alkylsulfo, alkylamino, thiol, hydroxy, nitro, cyano, amino, cycloalkyl, heterocyclic alkyl, aryl, heteroaryl, cycloalkoxyl, heterocyclic, cycloalkylthio, heterocyclic alkylthio and oxo group.

"Alkynyl" refers to an alkyl defined as above that has at least two carbon atoms and at least one carbon-carbon triple bond, for example, ethynyl, 1-propynyl, 2-propynyl, 1-, 2-, or 3-butynyl etc., preferably $C_{2-20}$ alkynyl, more preferably $C_{2-12}$ alkynyl, and most preferably $C_{2-6}$ alkynyl. The alkynyl group can be substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxo group.

"Alkylene" refers to a saturated linear or branched aliphatic hydrocarbon group, wherein having 2 residues derived by removing two hydrogen atoms from the same carbon atom of the parent alkane or two different carbon atoms. The straight or branched chain group containing 1 to 20 carbon atoms, preferably has 1 to 12 carbon atoms, more preferably 1 to 6 carbon atoms. Non-limiting examples of alkylene groups include, but are not limited to, methylene (—$CH_2$—), 1,1-ethylene (—$CH(CH_3)$—), 1,2-ethylene (—$CH_2CH_2$)—, 1,1-propylene (—$CH(CH_2CH_3)$—), 1,2-propylene (—$CH_2CH(CH_3)$—), 1,3-propylene (—$CH_2CH_2CH_2$—), 1,4-butylidene (—$CH_2CH_2CH_2CH_2$—) etc. The alkylene group can be substituted or unsubstituted. When substituted, the substituent group(s) is preferably one or more group(s) independently selected from the group consisting of selected from alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxo group.

"Alkenylene" refers to an alkylene defined as above that has at least two carbon atoms and at least one carbon-carbon double bond, preferably $C_{2-20}$ alkenylene, more preferably $C_{2-12}$ alkenylene, and most preferably $C_{2-6}$ alkenylene. Non-limiting examples of alkenylene groups include, but are not limited to, —CH=CH—, —CH=CHCH$_2$—, —CH=CHCH$_2$CH$_2$—, —CH$_2$CH=CHCH$_2$— etc. The alkenylene group can be substituted or unsubstituted. When substituted, the substituent group(s) is preferably one or more group(s) independently selected from the group consisting of selected from alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxo group.

"Cycloalkyl" refers to a saturated and/or partially unsaturated monocyclic or polycyclic hydrocarbon group having 3 to 20 carbon atoms, preferably 3 to 12 carbon atoms, more preferably 3 to 8 carbon atoms, and most preferably 5 to 8 carbon atoms or 5 to 6 carbon atoms. Representative examples of monocyclic cycloalkyls include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes a cycloalkyl having a spiro ring, fused ring or bridged ring.

"Spiro Cycloalkyl" refers to a 5 to 20 membered polycyclic group with rings connected through one common carbon atom (called a spiro atom), wherein one or more rings can contain one or more double bonds, it can be aryl and heteroaryl. Preferably a spiro cycloalkyl is 6 to 14 membered, and more preferably 8 to 10 membered. According to the number of common spiro atoms, a spiro cycloalkyl is divided into mono-spiro cycloalkyl, di-spiro cycloalkyl, or poly-spiro cycloalkyl, and preferably refers to a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Representative examples of spiro cycloalkyl include, but are not limited to the following groups:

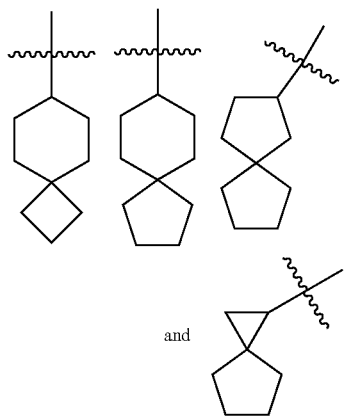

"Fused Cycloalkyl" refers to a polycyclic group, which is a cycloalkyl attached together with one or more group(s) selected from cycloalkyl, heterocyclyl, aryl and heteroaryl in a fused manner Wherein cycloalkyl, heterocyclyl, aryl and heteroaryl are as defined in the present invention. According to the number of membered rings, fused cycloalkyl is divided into bicyclic, tricyclic, tetracyclic or polycyclic fused cycloalkyl, and preferably refers to a bicyclic or tricyclic fused cycloalkyl, more preferably refers to aryl fused $C_{5-8}$cycloalkyl, heteroaryl fused $C_{5-8}$cycloalkyl. 4-membered heterocyclyl fused $C_{5-8}$ cycloalkyl, 5-membered heterocyclyl fused $C_{5-8}$ cycloalkyl, $C_6$ cycloalkyl fused $C_{5-8}$ cycloalkyl or $C_5$ cycloalkyl fused $C_{5-8}$ cycloalkyl, Representative examples of fused cycloalkyls include, but are not limited to, the following groups:

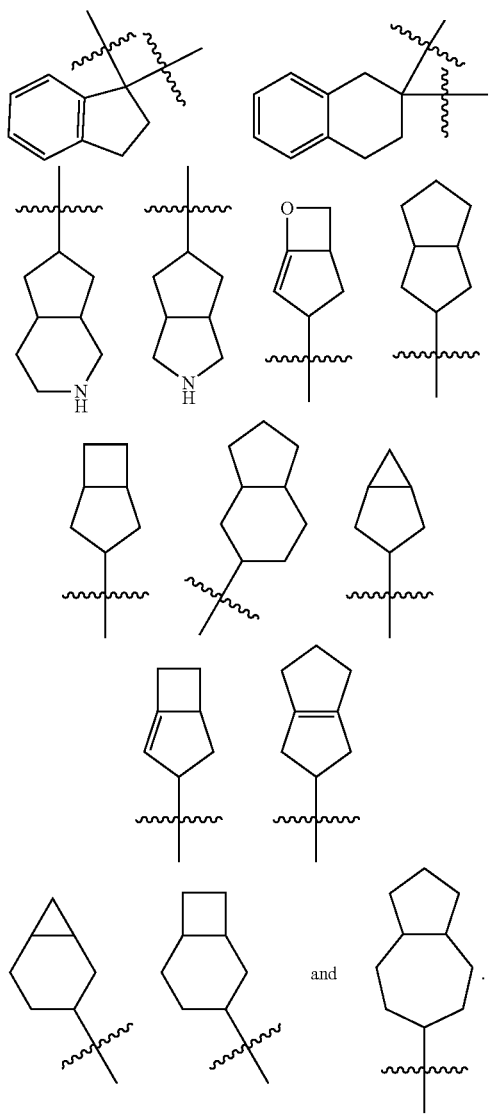

"Bridged Cycloalkyl" refers to a 5 to 20 membered polycyclic hydrocarbon group, wherein every two rings in the system share two disconnected carbon atoms. The rings can have one or more double bonds, but have no completely conjugated pi-electron system. Preferably, a bridged cycloalkyl is 6 to 14 membered, and more preferably 7 to 10 membered. According to the number of membered rings, bridged cycloalkyl is divided into bicyclic, tricyclic, tetracyclic or polycyclic bridged cycloalkyl, and preferably refers to a bicyclic, tricyclic or tetracyclic bridged cycloalkyl, more preferably a bicyclic or tricyclic bridged cycloalkyl. Representative examples of bridged cycloalkyls include, but are not limited to, the following groups:

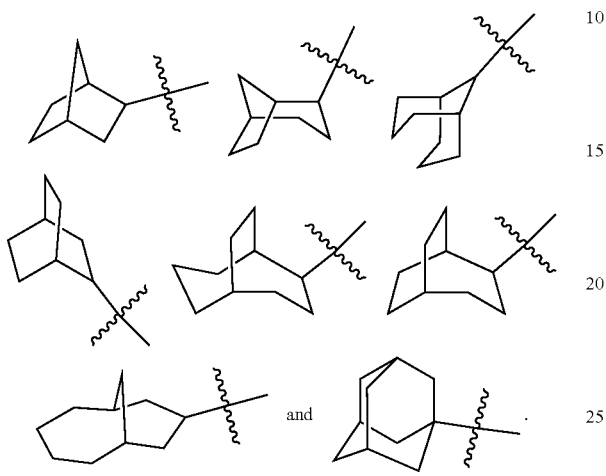

The cycloalkyl can be fused to the ring of an aryl, heteroaryl or heterocyclic alkyl, wherein the ring bound to the parent structure is cycloalkyl. Representative examples include, but are not limited to indanylacetic, tetrahydronaphthalene, benzocycloheptyl and so on. The cycloalkyl is optionally substituted or unsubstituted. When substituted, the substituent group(s) is preferably one or more groups independently selected from the group consisting of alkyl, halogen, alkoxy, alkenyl, alkynyl, alkylsulfo, alkylamino, thiol, hydroxy, nitro, cyano, amino, cycloalkyl, heterocyclic alkyl, aryl, heteroaryl, cycloalkoxyl, heterocyclic, cycloalkylthio, heterocyclic alkylthio and oxo group.

"Heterocyclyl" refers to a 3 to 20 membered saturated and/or partially unsaturated monocyclic or polycyclic hydrocarbon group having one or more heteroatoms selected from the group consisting of N, O, and S(O)m (wherein m is 0, 1, or 2) as ring atoms, but excluding —O—O—, —O—S— or —S—S— in the ring, the remaining ring atoms being C. Preferably, heterocyclyl is a 3 to 12 membered having 1 to 4 heteroatoms; more preferably a 3 to 10 membered having 1 to 3 heteroatoms; most preferably a 5 to 8 membered having 1 to 2 heteroatoms. Representative examples of monocyclic heterocyclyls include, but are not limited to, pyrrolidyl, piperidyl, piperazinyl, morpholinyl, sulfo-morpholinyl, homopiperazinyl, and so on. Polycyclic heterocyclyl includes the heterocyclyl having a spiro ring, fused ring or bridged ring.

"Spiro heterocyclyl" refers to a 5 to 20 membered polycyclic heterocyclyl with rings connected through one common carbon atom (called a spiro atom), wherein said rings have one or more heteroatoms selected from the group consisting of N, O, and S(O)m (wherein m is 0, 1 or 2) as ring atoms, the remaining ring atoms being C, wherein one or more rings can attached together with one or more group(s) selected from cycloalkyl, heterocyclyl, aryl and heteroaryl in a fused manner Wherein cycloalkyl, heterocyclyl, aryl and heteroaryl are as defined in the present invention. Preferably a spiro heterocyclyl is 6 to 14 membered. Representative examples of spiro heterocyclyl include, but are not limited to the following groups:

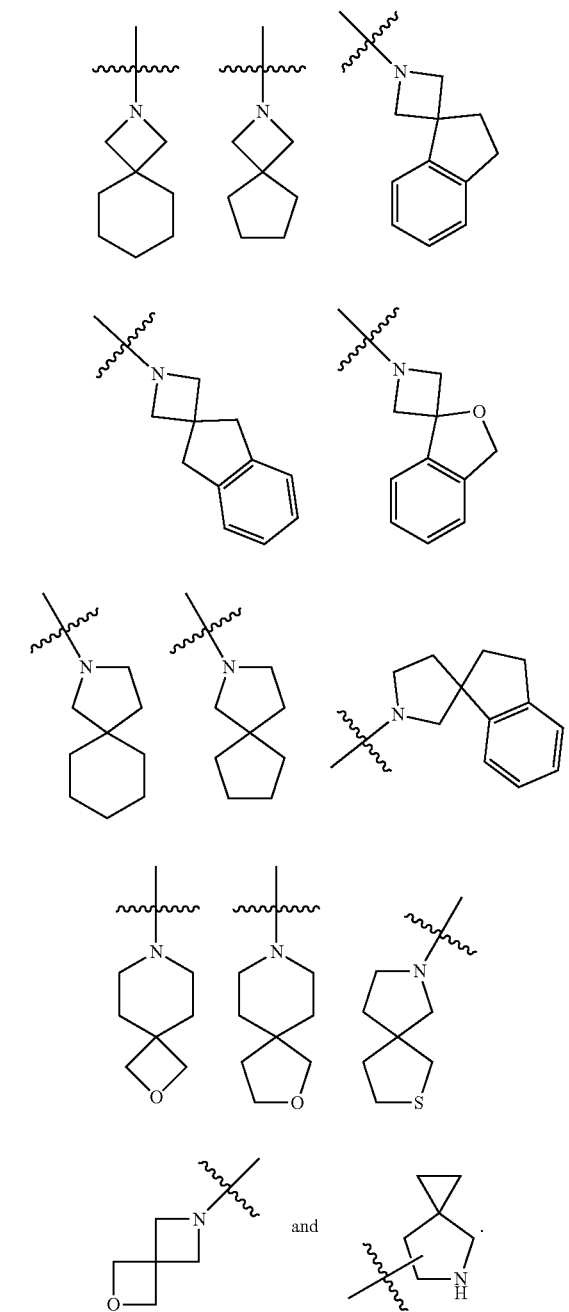

"Fused Heterocyclyl" refers to a polycyclic group, which is a heterocyclyl attached together with one or more group(s) selected from cycloalkyl, heterocyclyl, aryl and heteroaryl in a fused manner Wherein cycloalkyl, heterocyclyl, aryl and heteroaryl are as defined in the present invention. According to the number of membered rings, fused heterocyclyl is divided into bicyclic, tricyclic, tetracyclic or polycyclic fused heterocyclyl, and preferably refers to a bicyclic or tricyclic fused cycloalkyl, more preferably refers to aryl fused 5 to 8-member heterocyclyl, heteroaryl fused 5 to 8-member heterocyclyl. $C_{5-8}$ cycloalkyl fused 4-membered heterocyclyl, $C_{5-8}$ cycloalkyl fused 5-membered heterocyclyl, $C_{5-8}$ cycloalkyl fused 6-member heterocyclyl. Representative examples of fused heterocyclyl include, but are not limited to, the following groups:

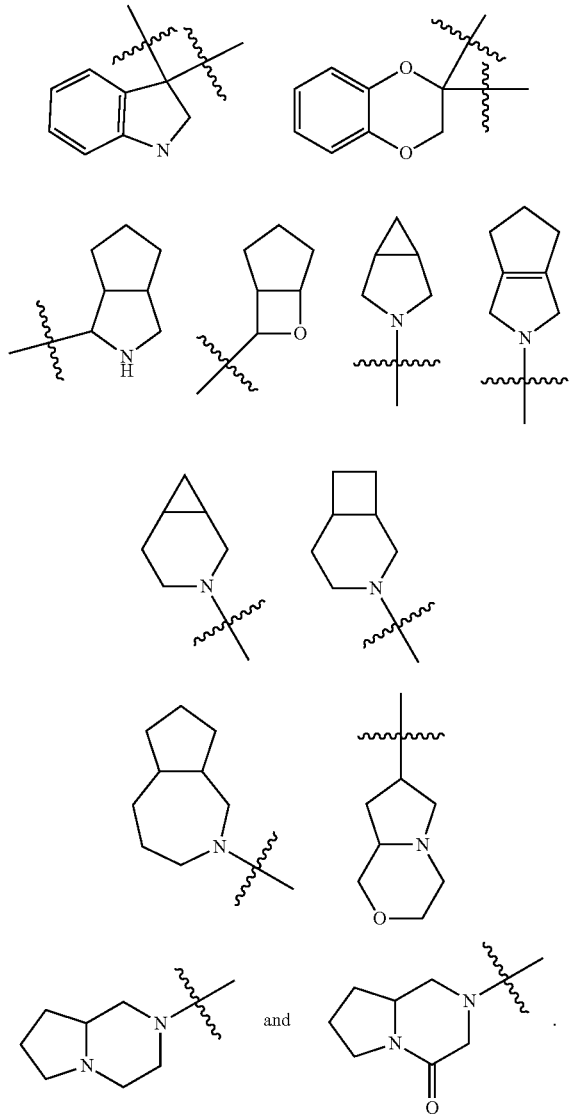

"Bridged Heterocyclyl" refers to a 5 to 14 membered polycyclic heterocyclic alkyl group, wherein every two rings in the system share two disconnected atoms, the rings can have one or more double bonds, but have no completely conjugated pi-electron system, and the rings have one or more heteroatoms selected from the group consisting of N, O, and S (O)m (wherein m is 0, 1, or 2) as ring atoms, the remaining ring atoms being C. Preferably a bridged heterocyclyl is 6 to 14 membered, and more preferably 7 to 10 membered. According to the number of membered rings, bridged heterocyclyl is divided into bicyclic, tricyclic, tetracyclic or polycyclic bridged heterocyclyl, and preferably refers to bicyclic, tricyclic or tetracyclic bridged heterocyclyl, more preferably bicyclic or tricyclic bridged heterocyclyl. Representative examples of bridged heterocyclyl include, but are not limited to, the following groups:

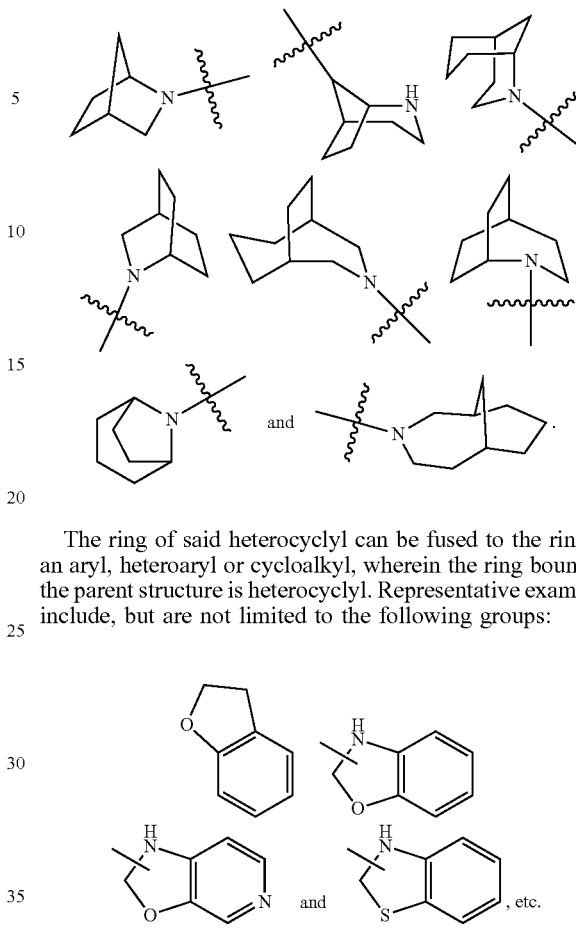

The ring of said heterocyclyl can be fused to the ring of an aryl, heteroaryl or cycloalkyl, wherein the ring bound to the parent structure is heterocyclyl. Representative examples include, but are not limited to the following groups:

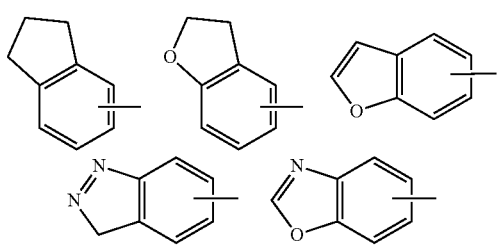

The heterocyclyl is optionally substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxy group.

"Aryl" refers to a 6 to 14 membered all-carbon monocyclic ring or a polycyclic fused ring (a "fused" ring system means that each ring in the system shares an adjacent pair of carbon atoms with another ring in the system) group, and has a completely conjugated pi-electron system. Preferably aryl is 6 to 10 membered, such as phenyl and naphthyl, most preferably phenyl. The aryl can be fused to the ring of heteroaryl, heterocyclyl or cycloalkyl, wherein the ring bound to parent structure is aryl. Representative examples include, but are not limited to, the following groups:

-continued

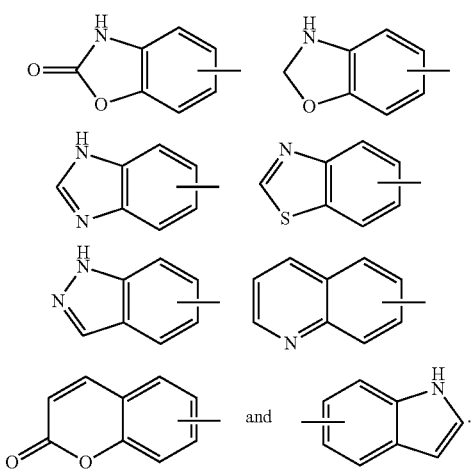

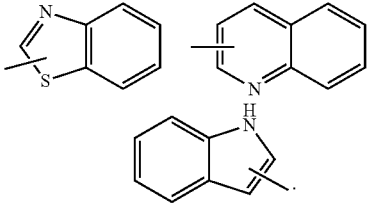 and

The aryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxy group.

"Heteroaryl" refers to an aryl system having 1 to 4 heteroatoms selected from the group consisting of O, S and N as ring atoms and having 5 to 14 annular atoms. Preferably a heteroaryl is 5- to 10-membered, more preferably 5- or 6-membered, for example, thiadiazolyl, pyrazolyl, oxazolyl, oxadiazolyl, imidazolyl, triazolyl, thiazolyl, furyl, thienyl, pyridyl, pyrrolyl, N-alkyl pyrrolyl, pyrimidinyl, pyrazinyl, imidazolyl, tetrazolyl, and the like. The heteroaryl can be fused with the ring of an aryl, heterocyclyl or cycloalkyl, wherein the ring bound to parent structure is heteroaryl. Representative examples include, but are not limited to, the following groups:

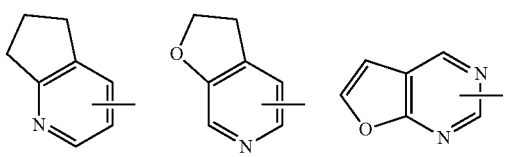

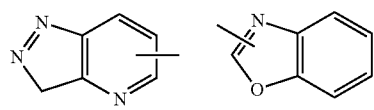

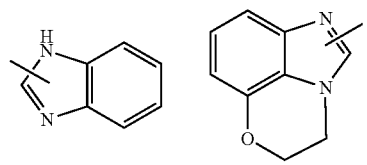

The heteroaryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxy group.

"Alkoxy" refers to both an —O-(alkyl) and an —O-(unsubstituted cycloalkyl) group, wherein the alkyl is defined as above. Representative examples include, but are not limited to, methoxy, ethoxy, propoxy, butoxy, cyclopropyloxy, cyclobutyloxy, cyclopentyloxy, cyclohexyloxy, and the like. The alkoxyl can be substituted or unsubstituted. When substituted, the substituent is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and oxy group.

"Bond" refers to a covalent bond using a sign of "—".

"Hydroxyalkyl" refers to an alkyl group substituted by a hydroxy group, wherein alkyl is as defined above.

"Hydroxy" refers to an —OH group.

"Halogen" refers to fluoro, chloro, bromo or iodo atoms.

"Amino" refers to a —NH$_2$ group.

"Cyano" refers to a —CN group.

"Nitro" refers to a —NO$_2$ group.

"Oxo group" refers to a =O group.

"Carboxyl" refers to a —C(O)OH group.

"Optional" or "optionally" means that the event or circumstance described subsequently can, but need not, occur, and the description includes the instances in which the event or circumstance may or may not occur. For example, "the heterocyclic group optionally substituted by an alkyl" means that an alkyl group can be, but need not be, present, and the description includes the case of the heterocyclic group being substituted with an alkyl and the heterocyclic group being not substituted with an alkyl.

"Substituted" refers to one or more hydrogen atoms in the group, preferably up to 5, more preferably 1 to 3 hydrogen atoms, independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxyl group having free hydrogen and carbon atoms having unsaturated bonds (such as olefinic) may be unstable.

A "pharmaceutical composition" refers to a mixture of one or more of the compounds described in the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient and thus displaying biological activity.

"Pharmaceutically acceptable salts" refer to salts of the compounds of the invention, such salts being safe and effective when used in a mammal and have corresponding biological activity.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14($^{14}$C), or non-radioactive isotopes, such as deuterium (D) or carbon-13($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of a CD73 inhibitor (or, e.g., a metabolite thereof) at a particular time post-administration may be indicative of whether a therapeutically effective amount has been used.

Synthetic Methods

In order to complete the purpose of the invention, the present invention applies, but is not limited to, the following technical solution:

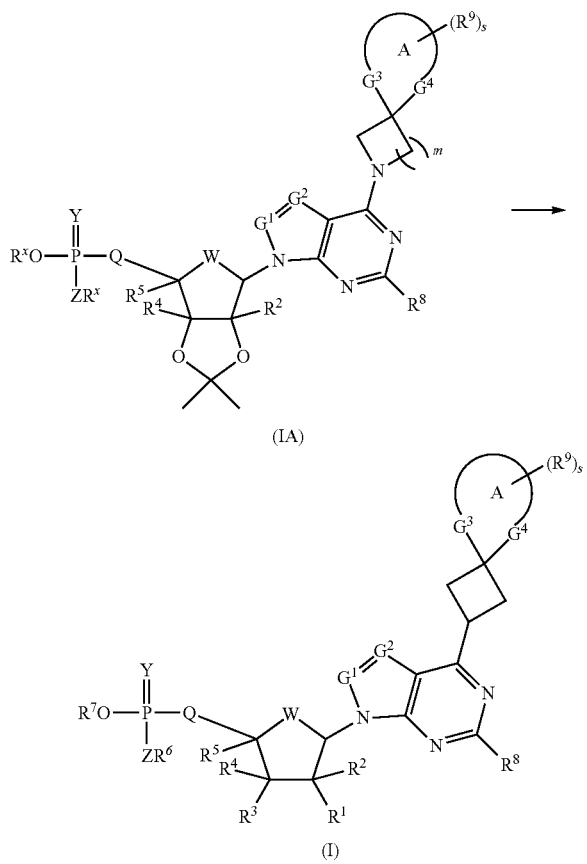

reacting to remove the protecting group of $R^x$ and acetal with a compound of formula (IA) under acidic condition (such as TMSBr) to obtain the compound of formula (I);

wherein:

$R^x$ is alkyl;

Z is O;

$R^6$ and $R^7$ are both hydrogen;

$R^1$ and $R^3$ are both hydroxy; and

Y, W, Q, $G^1$, $G^2$, $G^3$, $G^4$, ring A, $R^2$, $R^4$, $R^5$, $R^8$, $R^9$, m and s are as defined in formula (I).

Agents that provide acidic conditions include, but are not limited to, hydrogen chloride, hydrogen chloride 1,4-dioxane solution, trimethylsilyl bromide (TMSBr), ammonium chloride, trifluoroacetic acid, formic acid, acetic acid, hydrochloric acid, sulfuric acid, methanesulfonic acid, nitric acid, phosphoric acid, p-toluenesulfonic acid, p-toluenesulfonic acid monohydrate and TMSOTf;

The reaction is preferably in solvent, wherein solvent used herein includes, but is not limited to, acetic acid, methanol, ethanol, toluene, acetone, tetrahydrofuran, dichloromethane, dimethylsulfoxide, 1,4-dioxane, water, N, N-dimethylformamide and the mixture thereof.

In order to complete the purpose of the invention, the present invention applies, but is not limited to, the following technical solution:

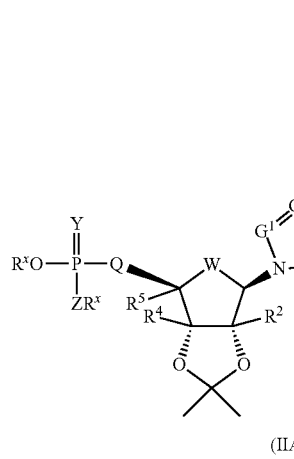

(IIA)

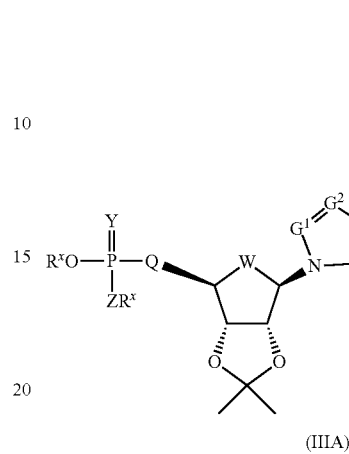

(IIIA)

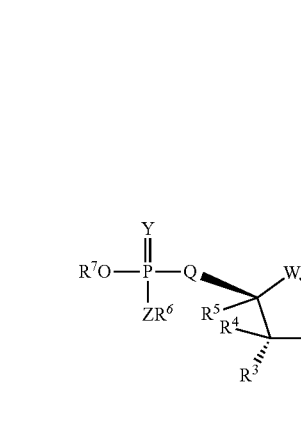

(II)

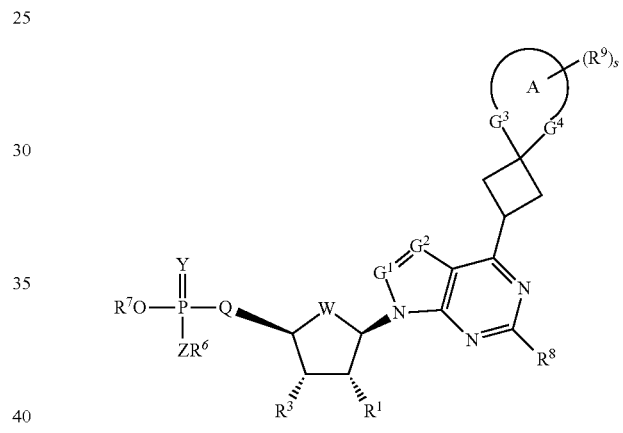

(III)

reacting to remove the protecting group of $R^x$ and acetal with a compound of formula (IIA) under acidic condition (such as TMSBr) to obtain the compound of formula (II);

wherein:

$R^x$ is alkyl;

Z is O;

$R^6$ and $R^7$ are both hydrogen;

$R^1$ and $R^3$ are both hydroxy; and

Y, W, Q, $G^1$, $G^2$, $G^3$, $G^4$, ring A, $R^2$, $R^4$, $R^5$, $R^8$, $R^9$, m and s are as defined in formula (II).

Agents that provide acidic conditions include, but are not limited to, hydrogen chloride, hydrogen chloride 1,4-dioxane solution, trimethylsilyl bromide (TMSBr), ammonium chloride, trifluoroacetic acid, formic acid, acetic acid, hydrochloric acid, sulfuric acid, methanesulfonic acid, nitric acid, phosphoric acid, p-toluenesulfonic acid, p-toluenesulfonic acid monohydrate and TMSOTf;

The reaction is preferably in solvent, wherein solvent used herein includes, but is not limited to, acetic acid, methanol, ethanol, toluene, acetone, tetrahydrofuran, dichloromethane, dimethylsulfoxide, 1,4-dioxane, water, N, N-dimethylformamide and the mixture thereof.

In order to complete the purpose of the invention, the present invention applies, but is not limited to, the following technical solution:

reacting to remove the protecting group of $R^x$ and acetal with a compound of formula (IIIA) under acidic condition (such as TMSBr) to obtain the compound of formula (III);

wherein:

$R^x$ is alkyl;

Z is O;

$R^1$ and $R^3$ are both hydroxy; and

W, Q, $G^1$, $G^2$, $G^3$, $G^4$, ring A, $R^8$, $R^9$, m and s are as defined in formula (III).

Agents that provide acidic conditions include, but are not limited to, hydrogen chloride, hydrogen chloride 1,4-dioxane solution, trimethylsilyl bromide (TMSBr), ammonium chloride, trifluoroacetic acid, formic acid, acetic acid, hydrochloric acid, sulfuric acid, methanesulfonic acid, nitric acid, phosphoric acid, p-toluenesulfonic acid, p-toluenesulfonic acid monohydrate and TMSOTf;

The reaction is preferably in solvent, wherein solvent used herein includes, but is not limited to, acetic acid, methanol, ethanol, toluene, acetone, tetrahydrofuran, dichloromethane, dimethylsulfoxide, 1,4-dioxane, water, N, N-dimethylformamide and the mixture thereof.

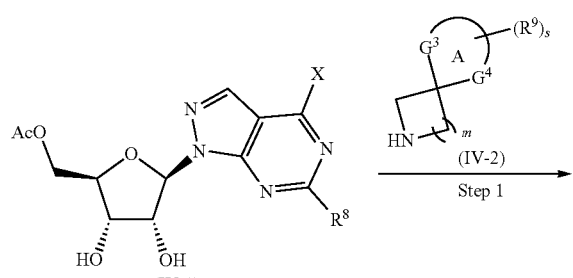

(IV-1)

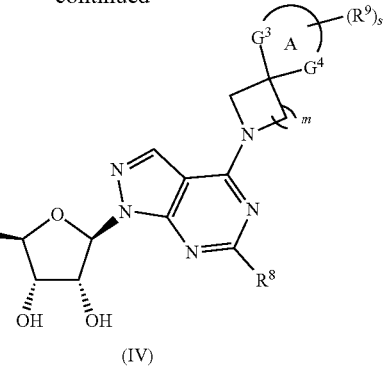

(IV)

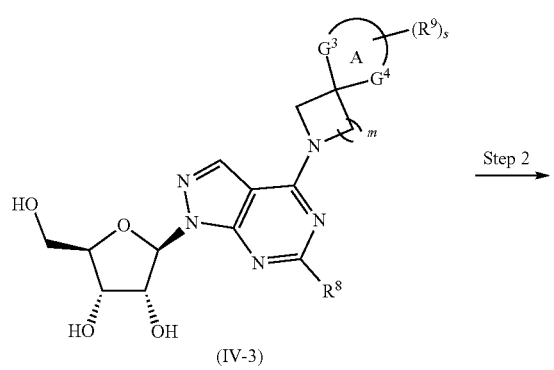

(IV-3)

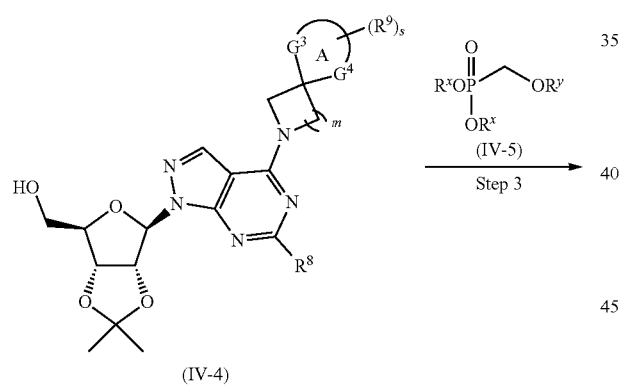

(IV-4)

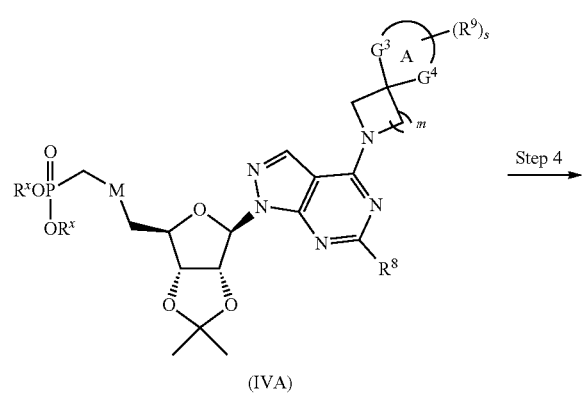

(IVA)

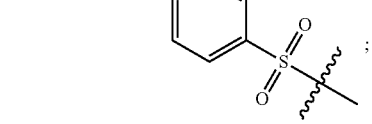

(IV-5)

Step 1, reacting with formula (IV-1) and formula (IV-2) under alkaline condition (such as DBU) to obtain formula (IV-3);

Step 2, reacting with formula (IV-3) and 2,2-dimethoxypropane under acidic condition (such as p-toluenesulfonic acid), then neutralize the reaction mixture to obtain formula (IV-4);

Step 3, reacting with formula (IV-4) and formula (IV-5) under alkaline condition (such as magnesium t-butoxide) to obtain formula (IVA);

Step 4, reacting to remove the protecting group of $R^x$ and acetal with a compound of formula (IVA) under acidic condition (such as TMSBr) to obtain the compound of formula (IV);

wherein:

X is halogen, preferably chlorine;

$R^x$ is alkyl;

$R^y$ is leaving group, preferably

M is O; and ring A, $G^3$, $G^4$, $R^8$, $R^9$, m and s are as defined in formula (IV).

The alkaline conditions are provided by an organic base or inorganic base, wherein said organic base includes, but is not limited to, triethylamine, N, N-diisopropylethylamine, 1,8-diazabicyclo[5.4.0]undec-7-ene (DBU), n-butyllithium, tert-butyl potassium alkoxide, magnesium t-butoxide; and said inorganic base includes, but is not limited to, sodium hydride, sodium carbonate, sodium bicarbonate, potassium carbonate, potassium bicarbonate, or cesium carbonate.

Agents that provide acidic conditions include, but are not limited to, hydrogen chloride, hydrogen chloride 1,4-dioxane solution, trimethylsilyl bromide (TMSBr), ammonium chloride, trifluoroacetic acid, formic acid, acetic acid, hydrochloric acid, sulfuric acid, methanesulfonic acid, nitric acid, phosphoric acid, p-toluenesulfonic acid, p-toluenesulfonic acid monohydrate and TMSOTf;

The reaction is preferably in solvent, wherein solvent used herein includes, but is not limited to, acetic acid, methanol, ethanol, toluene, acetone, tetrahydrofuran, dichloromethane, dimethylsulfoxide, 1,4-dioxane, water, N, N-dimethylformamide and the mixture thereof.

EXAMPLES

The structure of a compound is determined by mass spectrometry (MS) and or nuclear magnetic resonance (NMR). NMR shift (δ) is given in units of $10^{-6}$ (ppm).

The mass spectrum (MS) was determined using a Shimadzu LCMS-2020 liquid chromatography-mass spectrometer.

The NMR measurement was performed on a Bruker AVANCE-400 and 500 Ultrashield nuclear magnetic resonance spectrometer. The solvents were deuterated dimethylsulfoxide (DMSO-$d_6$), deuterated chloroform (CDCl$_3$) and deuterated methanol (CD$_3$OD).

HPLC was performed using a Shimadzu OPTION BOX-L high pressure liquid phase Chromatograph (Gimini 5 um NX-C18 100×21.2 mm column).

Thin-layer chromatography (TLC) silica gel plates used were Agela Technologies T-CSF10050-M silica gel plate with size of 50 mm, Column chromatography was commonly done using CombiFlash Rf+ Automated Flash Chromatography System (TELEDYNE ISCO) with Agela Technologies Flash Column Silica-CS prepacked columns.

Known starting materials of the present invention may be synthesized according to methods known in the art or may be purchased from Acros Organics, Sigma-Aldrich Chemical Company, AstaTech and other companies. Unless otherwise specified in the examples, the reaction can be carried out under an argon atmosphere or a nitrogen atmosphere.

Argon or nitrogen atmosphere refers to the reaction flask connected to a volume of about 1 L argon or nitrogen balloon.

Hydrogen atmosphere refers to the reaction bottle connected to a volume of about 1 L hydrogen balloon.

Hydrogenation reaction is usually evacuated, filled with hydrogen, repeated 3 times.

The microwave reaction used a CEM Discover-S 908860 microwave reactor.

Unless otherwise specified in the examples, the reaction temperature is room temperature and is 20° C. to 30° C.

The progress of the reaction in the examples was monitored using thin layer chromatography (TLC), developing solvent for the reaction, a column chromatography eluent for purifying compound, and developing system for thin-layer chromatography include: A: dichloromethane/methanol system, B: n-hexane/ethyl acetate system, C: dichloromethane/ethyl acetate system. The volume ratio of the solvents is adjusted according to the polarity of the compound. A small amount of triethylamine and acetic acid and other alkaline or acidic reagents can be used for adjustment.

TEA is triethylamine,
THF is tetrahydrofuran,
DBU is 1,8-diazabicyclo[5.4.0]undec-7-ene,
DIAD is diisopropyl azodicarboxylate,
DIPEA is N,N-diisopropylethylamine,
EtOAc is ethyl acetate,
Et$_3$N is triethylamine,
HATU is 1-[Bis(dimethylamino)methylene]-1H-1,2,3-triazolo[4,5-b]pyridinium 3-oxid hexafluorophosphate,
MgSO$_4$ is magnesium sulfate,
NaHCO$_3$ is sodium bicarbonate,
NH$_4$HCO$_3$ is ammonium bicarbonate,
TBAF is tetra-n-butylammonium fluoride,
p-TsOH is p-Toluenesulfonic acid,
TMSBr is bromotrimethylsilane,
TMSOTf is trimethylsilyl trifluoromethanesulfonate,
DCM is dichloromathene,
DMF is N,N-dimethylformamide,
DMSO is dimethyl sulfoxide, and
MS is mass spectroscopy with (+) referring to the positive mode which generally gives a M+1 (or M+H) absorption where M is equal to the molecular mass.

Example 1

(((((2R,3S,4R,5R)-5-(6-chloro-4-(2-azaspiro[3.5]nonan-2-yl)-1H-pyrazolo[3,4-d]pyrimidin-1-yl)-3,4-dihydroxytetrahydrofuran-2-yl)methoxy)methyl)phosphonic acid 1

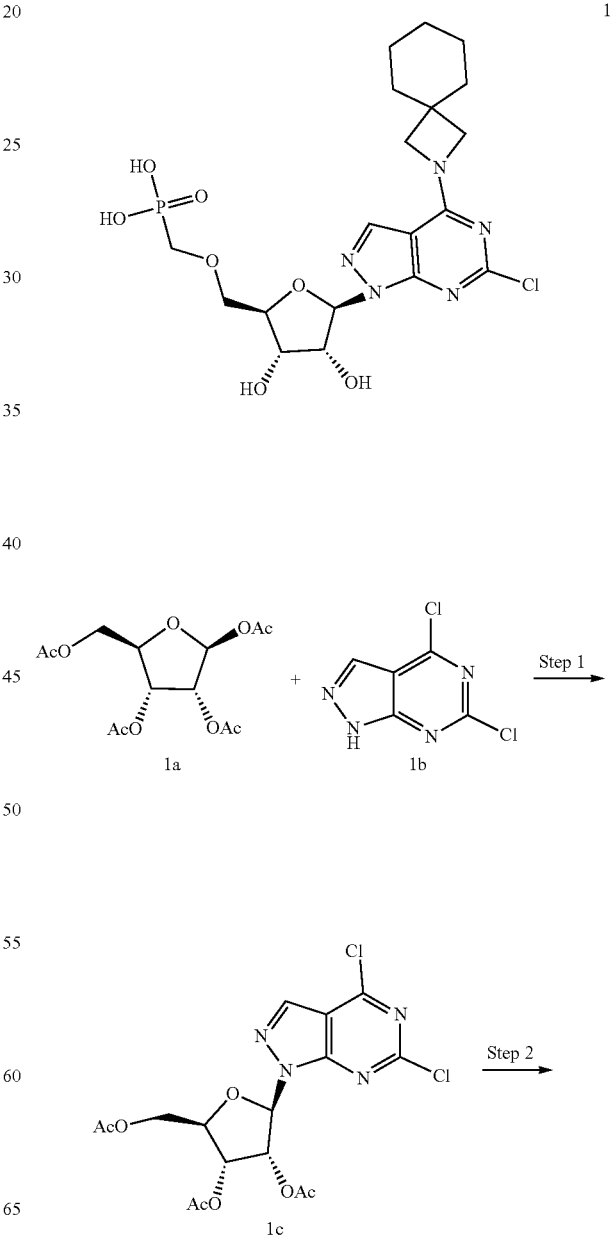

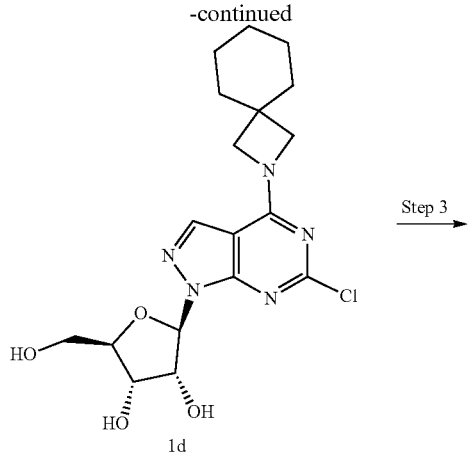

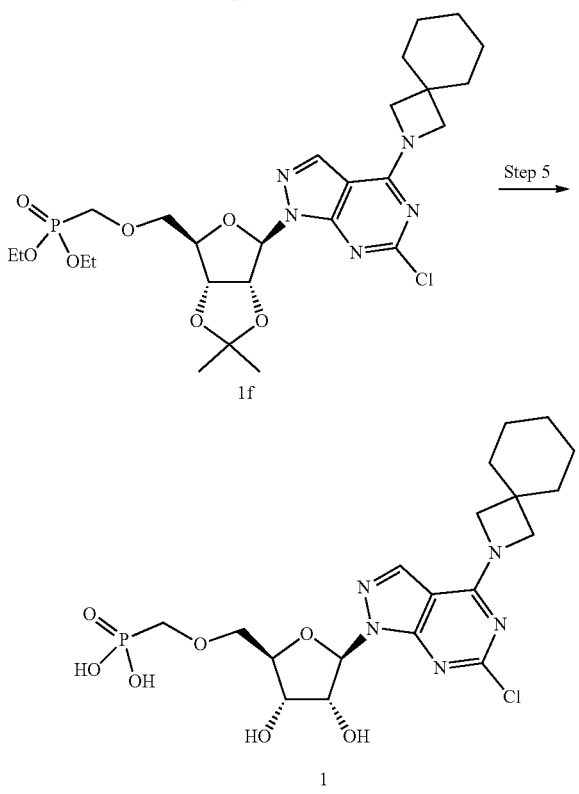

Step 1

(2R,3R,4R,5R)-2-(acetoxymethyl)-5-(4,6-dichloro-1H-pyrazolo[3,4-d]pyrimidin-1-yl)tetrahydrofuran-3,4-diyl diacetate 1c To a dried round-bottom flask (500 mL) was charged with 4,6-dichloro-1H-pyrazolo[3,4-d] pyrimidine 1b (12.5 g, 66.1 mmol), ammonium sulfate (0.1 g, 0.75 mmol) and hexamethyldisilazane (75 mL). After 3 h refluxing, the mixture was cooled to room temperature, and then concentrated to dryness in vacuo. The resulting residue was taken up into acetonitrile (150 mL) followed by addition of (2S,3R,4R,5R)-5-(acetoxymethyl)-tetrahydrofuran-2,3,4-triyl triacetate 1a (25.3 g, 79.5 mmol). The mixture was then cooled down to 0° C., followed by addition of TMSOTf (13.5 mL, 72.5 mmol) dropwise.

After 18 h stirring with the temperature slowly warmed up to room temperature, the reaction mixture was concentrated by rotavapor and the residue was taken up into EtOAc (150 mL), washed with sat. aq. NaHCO$_3$ solution and brine in sequence. The organic phase was dried over anhydrous MgSO$_4$, filtered, concentrated by rotavapor and the residue was purified by column chromatography on silica-gel with 0-40% EtOAc in hexane as eluent on the TELEDYNE ISCO system to give 1c as yellowish sticky oil (22.4 g, yield: 76%), MS (ESI): m/z=447 [M+1].

Step 2

(2R,3R,4S,5R)-2-(6-chloro-4-(2-azaspiro[3.5]nonan-2-yl)-1H-pyrazolo[3,4-d]pyrimidin-1-yl)-5-(hydroxymethyl)tetrahydrofuran-3,4-diol 1d To a solution of (2R,3R,4R,5R)-2-(acetoxymethyl)-5-(4,6-dichloro-1H-pyrazolo[3,4d]pyrimidin-1-yl)tetrahydrofuran-3,4-diyl diacetate 1e (3 g, 6.72 mmol) in MeOH (15 mL) was added 2-azaspiro[3.5]nonane (0.84 g, 6.72 mmol) and Et3N (0.94 mL, 6.72 mmol) in sequence at room temperature. After 2 h stirring at room temperature, to the mixture was added DBU (1.51 mL, 10.08 mmol). The reaction mixture was further stirred for 2 hrs at room temperature, concentrated in vacuo. The resulting residue was purified by column chromatography on silica-gel with 5% MeOH in DCM as eluent on the TELEDYNE ISCO system to yield 1d as white solids (2.1 g, yield: 76%), MS (ESI): m/z=410 [M+1].

Step 3

((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d] [1,3]dioxol-4-yl) methanol 1e To a solution of (2R,3R,4S,5R)-2-(6-chloro-4-(2-azaspiro [3.5]nonan-2-yl)-1H-pyrazolo[3,4-d]pyrimidin-1-yl)-5-(hydroxymethyl)tetrahydrofuran-3,4-diol 1d (1.12 g, 2.74 mmol) in anhydrous acetone (15 mL) was added 2,2-dimethoxypropane (4.04 mL, 32.88 mmol) and p-toluenesulfonic acid monohydrate (521 mg, 2.74 mmol) in sequence. After 2 h stirring at room temperature, to the mixture was added sodium bicarbonate (345 mg, 4.1 mmol) and water (7 mL), and the mixture was continued to stir for 2 hrs at room temperature. The mixture was diluted with water (10 mL) and extracted with EtOAc (2×50 mL). The combined organic phases were washed with brine, dried over anhydrous MgSO₄, filtered and concentrated in vacuo. The residue was purified by column chromatography on silica-gel with 0-60% EtOAc in hexane as eluent on the TELEDYNE ISCO system to give 1e as white solids (0.98 g, yield: 80%), MS (ESI): m/z=450 [M+1].

Step 4 diethyl ((((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl)methoxy)methyl)phosphonate 1f A solution of ((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl) methanol 1e (168 mg, 0.37 mmol) and magnesium t-butoxide (95 mg, 0.56 mmol) in DMF (2 mL) was stirred at room temperature for 5 min before addition of a solution of (diethoxyphosphoryl)-methyl 2-nitrobenzenesulfonate (198 mg, 0.56 mmol) in DMF (1 mL). After 3 h stirring at 40° C., the reaction mixture was concentrated in vacuo. The residue was then purified by column chromatography on silica-gel with 0-50% EtOAc in hexane as eluent on the TELEDYNE ISCO system to give 1f as white solids (155 mg, yield: 70%), MS (ESI): m/z=600 [M+1].

Step 5

(((((2R,3S,4R,5R)-5-(6-chloro-4-(2-azaspiro[3.5]nonan-2-yl)-1H-pyrazolo[3,4-d]pyrimidin-1-yl)-3,4-dihydroxytetrahydrofuran-2-yl)methoxy)methyl)phosphonic acid 1

To a solution of diethyl ((((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl)methoxy)methyl)phosphonate 1f (103.8 mg, 0.17 mmol) in DCM (2 mL) was added TMSBr (0.23 mL, 1.73 mmol) dropwise at 0° C. After 5 h stirring at 0° C., the reaction mixture was quenched with aq. sat. NaHCO₃ solution, purified by HPLC to yield 1 as white solids (25 mg, yield: 29%): ¹H NMR (500 MHz, DMSO-d6) δ 8.19 (s, 1H), 6.02 (d, J=4.3 Hz, 1H), 4.57 (t, J=4.7 Hz, 1H), 4.33 (t, J=4.9 Hz, 1H), 4.21-4.12 (m, 2H), 4.06 (m, 2H), 3.92 (brs, 3H), 3.80-3.70 (m, 3H), 3.70-3.10 (m, 3H), 1.73-1.71 (m, 2H), 1.54-1.44 (m, 4H), 1.42-1.35 (m, 2H), 1.34-1.24 (m, 2H). ³¹P NMR (203 MHz, DMSO-d6) δ 17.00 (s). MS (ESI): m/z=504 [M+1].

Example 2

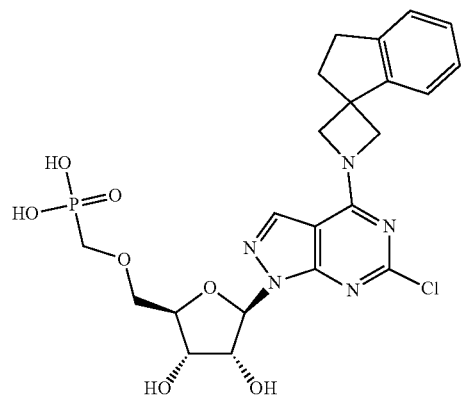

(((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 2

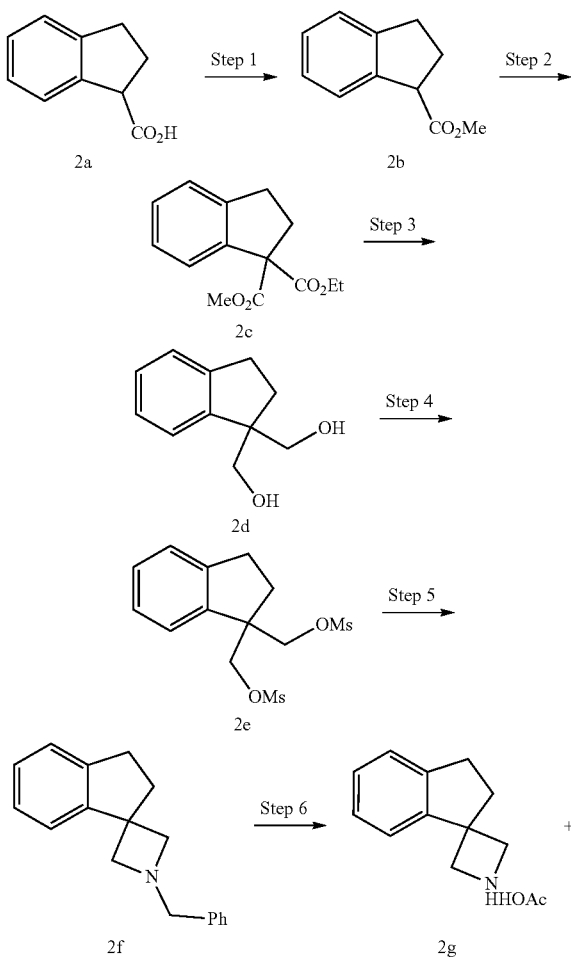

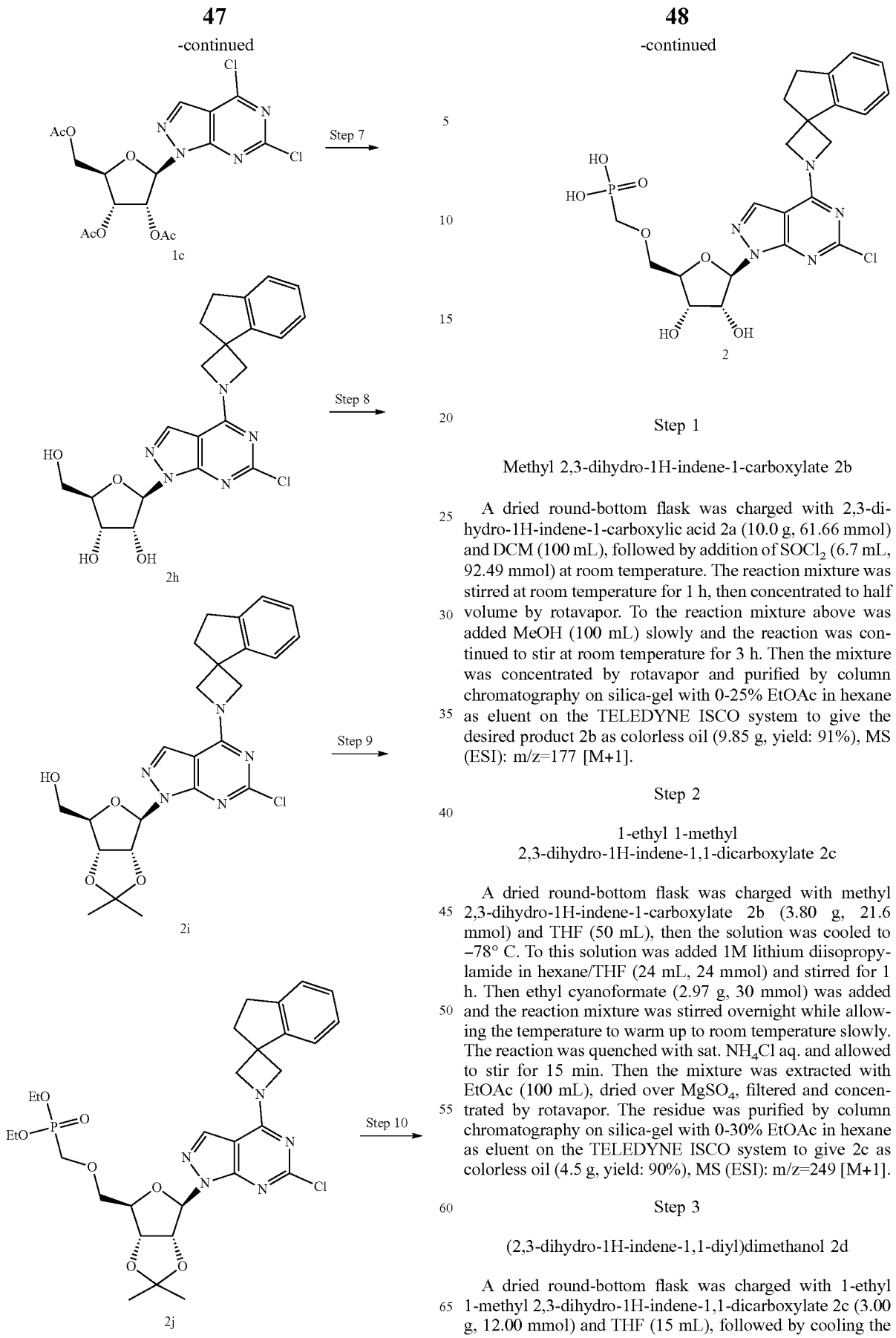

Step 1

Methyl 2,3-dihydro-1H-indene-1-carboxylate 2b

A dried round-bottom flask was charged with 2,3-dihydro-1H-indene-1-carboxylic acid 2a (10.0 g, 61.66 mmol) and DCM (100 mL), followed by addition of $SOCl_2$ (6.7 mL, 92.49 mmol) at room temperature. The reaction mixture was stirred at room temperature for 1 h, then concentrated to half volume by rotavapor. To the reaction mixture above was added MeOH (100 mL) slowly and the reaction was continued to stir at room temperature for 3 h. Then the mixture was concentrated by rotavapor and purified by column chromatography on silica-gel with 0-25% EtOAc in hexane as eluent on the TELEDYNE ISCO system to give the desired product 2b as colorless oil (9.85 g, yield: 91%), MS (ESI): m/z=177 [M+1].

Step 2

1-ethyl 1-methyl 2,3-dihydro-1H-indene-1,1-dicarboxylate 2c

A dried round-bottom flask was charged with methyl 2,3-dihydro-1H-indene-1-carboxylate 2b (3.80 g, 21.6 mmol) and THF (50 mL), then the solution was cooled to −78° C. To this solution was added 1M lithium diisopropylamide in hexane/THF (24 mL, 24 mmol) and stirred for 1 h. Then ethyl cyanoformate (2.97 g, 30 mmol) was added and the reaction mixture was stirred overnight while allowing the temperature to warm up to room temperature slowly. The reaction was quenched with sat. $NH_4Cl$ aq. and allowed to stir for 15 min. Then the mixture was extracted with EtOAc (100 mL), dried over $MgSO_4$, filtered and concentrated by rotavapor. The residue was purified by column chromatography on silica-gel with 0-30% EtOAc in hexane as eluent on the TELEDYNE ISCO system to give 2c as colorless oil (4.5 g, yield: 90%), MS (ESI): m/z=249 [M+1].

Step 3

(2,3-dihydro-1H-indene-1,1-diyl)dimethanol 2d

A dried round-bottom flask was charged with 1-ethyl 1-methyl 2,3-dihydro-1H-indene-1,1-dicarboxylate 2c (3.00 g, 12.00 mmol) and THF (15 mL), followed by cooling the solution down to 0° C. To this solution was added 1M lithium aluminum hydride in THF (96 mL, 96 mmol) dropwise and the mixture was stirred overnight to allow the temperature to rise to room temperature. The mixture was quenched with sat. NH₄Cl aq. and 4M HCl respectively at 0° C. to get a clear solution, then extracted with EtOAc (3×100 mL). The combined organic phases were dried over MgSO₄, filtered and concentrated by rotavapor. The resulted residue was purified by column chromatography on silica-gel with 0-50% EtOAc in hexane as eluent on the TELEDYNE ISCO system to give 2d as white solids (1.6 g, yield: 75%), MS (ESI): m/z=179 [M+1].

Step 4

(2,3-dihydro-1H-indene-1,1-diyl)bis(methylene) dimethanesulfonate 2e

A dried round-bottom flask was charged with (2,3-dihydro-1H-indene-1,1-diyl) dimethanol 2d (1.00 g, 5.61 mmol), Et₃N (2.72 mL, 19.64 mmol) and DCM (15 mL), followed by cooling the solution down to 0° C. To this solution was added methanesulfonyl chloride (1.30 mL, 16.83 mmol) and stirred at 0° C. for 2 h. Then the mixture was diluted with EtOAc (25 mL), washed with water. The organic phase was separated and the aqueous phase was extracted with EtOAc (2×25 mL). The combined organic phases were dried over MgSO₄, filtered, and concentrated by rotavapor. The residue was purified by column chromatography on silica-gel with 0-30% EtOAc in hexane as eluent on the TELEDYNE ISCO system to give 2e as white solids (1.73 g, yield: 92%), MS (ESI): m/z=335 [M+1].

Step 5

1-benzyl-2',3'-dihydrospiro[azetidine-3,1'-indene]2f

A vial was charged with (2,3-dihydro-1H-indene-1,1-diyl)bis(methylene) dimethanesulfonate 2e (1.50 g, 4.49 mmol) and benzylamine (10 mL), followed by stirring at 110° C. for 15 h. After cooling, removal of volatile on rotavapor, the residue was diluted with EtOAc (50 mL) and quenched with sat. NaHCO₃ aq. The organic phase was separated and the aqueous phase was extracted with EtOAc (50 mL). The combined organic phases were dried over MgSO₄, filtered and concentrated by rotavapor. The residue was purified by column chromatography on silica-gel with 0-60% EtOAc in hexane as eluent on the TELEDYNEISCO system to give 2f as white solids (0.26 g, yield: 23%), MS (ESI): m/z=250 [M+1].

Step 6

2',3'-dihydrospiro[azetidine-3,1'-indene] acetate 2 g

A round-bottom flask was charged with 1-benzyl-2',3'-dihydrospirao[azetidine-3,1'-indene] 2f (0.26 g, 1.04 mmol), 20% Pd/C (100 mg), AcOH (0.1 mL) and methanol (15 mL). The flask was capped with septum and exchanged air with nitrogen gas by vacuum and refilling nitrogen gas. The mixture was then stirred under 1 atm H₂ atmosphere at room temperature for 15 h. The solid was removed by filtration and washed with methanol. The filtrate was concentrated on rotavapor and the residue was dried in vacuum to give the crude 2 g, which was used directly for next reaction without further purification, MS (ESI): m/z=160 [M+1].

Step 7

(2R,3R,4S,5R)-2-(6-chloro-4-(2',3'-dihydrospiro[azetidine-3,1'-inden]-1-yl)-1H pyrazolo[3,4-d]pyrimidin-1-yl)-5-(hydroxymethyl)tetrahydrofuran-3,4-diol 2 h A round-bottom flask was charged with the crude 2',3'-dihydrospirao[azetidine-3,1'-indene] 2 g (0.26 g, 1.20 mmol), Et₃N (0.5 mL, 3.6 mmol) and methanol (10 mL), which was then cooled down to 0° C. To this solution was added a solution of (2R,3R,4R,5R)-2-(acetoxymethyl)-5-(4,6-dichloro-1H-pyrazolo[3,4-d]pyrimidin-1-yl)tetrahydrofuran-3,4-diyl diacetate 1c (0.54 g, 1.2 mmol) in methanol (2 mL) and the reaction mixture was stirred at 0° C. for 1 h and room temperature for 1 h respectively. The reaction mixture was then re-cooled down to 0° C., followed by addition of DBU (0.51 mL, 3.6 mmol). The reaction was run for 2 h while allowing the temperature warm to room temperature. The mixture was concentrated by rotavapor and the residue was purified by column chromatography on silica-gel with 0-10% methanol in dichloromethane as eluent on the TELEDYNE ISCO system to give 2 h as white solids (0.33 g, yield: 62%), MS (ESI): m/z=444 [M+1].

Step 8

((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methanol 2i A vial was charged with (2R,3R,4S,5R)-2-(6-chloro-4-(2',3'-dihydrospiro[azetidine-3,1'-inden]-1-yl)-1H-pyrazolo[3,4-d]pyrimidin-1-yl)-5-(hydroxymethyl)tetrahydrofuran-3,4-diol 2 h (0.33 g, 0.74 mmol), 2,2-dimethoxypropane (1.12 mL, 8.88 mmol) and acetone (5 mL). To this solution was added p-toluenesulfonic acid monohydrate (0.13 g, 0.68 mmol) and the reaction was stirred at room temperature for 4 h. The reaction mixture was concentrated by rotavapor and the residue was taken into EtOAc (25 mL), followed by quenching with sat. NaHCO₃ aq. and extracting with EtOAc (2×25 mL). The combined organic phases were washed with brine, dried over anhydrous MgSO₄, filtered and concentrated by rotavapor. The residue was purified by column chromatography on silica-gel with 0-40% EtOAc in DCM as eluent on the TELEDYNE ISCO system to give 2i as white solids (0.18 g, yield: 50%), MS (ESI): m/z=484 [M+1].

Step 9 diethyl ((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl) phosphonate 2j A dried vial was charged with ((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methanol 2i (0.10 g, 0.21 mmol), Mg(OtBu)₂ (0.11 g, 0.32 mmol) and DMF (1.5 mL), followed by stirring at room temperature for 5 min. To this mixture was added a solution of (diethoxyphosphoryl)methyl nosylate (72 mg, 0.42 mmol) in DMF (0.5 mL) and stirred at 40° C. for 3 h. The reaction mixture was then diluted with H₂O (5 mL), quenched with sat NH₄Cl aq. (2 mL) and extracted with EtOAc (3×15 mL). The combined organic phases were washed with brine, dried over anhydrous MgSO₄, filtered and concentrated by rotavapor. The residue was purified by column chromatography on silica-gel with 0-70% EtOAc in DCM as eluent on the TELEDYNE ISCO system to give 2j as colorless sticky oil (0.13 g, yield: 98%), MS (ESI): m/z=634 [M+1].

Step 10

(((((2R,3S,4R,5R)-5-(6-chloro-4-(2',3'-dihydrospiro [azetidine-3,1'-inden]-1-yl)-1H-pyrazolo[3,4-d]pyrimidin-1-yl)-3,4-dihydroxytetrahydrofuran-2-yl) methoxy)methyl)phosphonic acid 2

A dried vial was charged with diethyl (((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl) phosphonate 2j (130 mg, 0.21 mmol) and DCM (3 mL), followed by cooling the solution down to 0° C. with an ice-bath. To it was added dropwise trimethylsilyl bromide (0.23 mL, 1.68 mmol) and the reaction mixture was stirred at 0° C. for 4 h. The solution was then concentrated at 0° C. by rotavapor and the residue was dried in vacuum. To the residue was added an ice-cold aq. TFA solution (0.64 mL with 5% H₂O). After 1 h stirring at 0° C., the reaction mixture was added dropwise into a solution of sodium carbonate (0.89 g) in H₂O (10 mL) under stirring. After 30 min, the suspended mixture was mixed with acetonitrile and water to get a clear solution, which was used for the purification by HPLC with 10-70% methanol in H₂O+0.5% NH₄HCO₃ to give 2 as white solids (56 mg, yield: 49%). MS (ESI): m/z=538 [M+1]. ¹H NMR (500 MHz, Methanol-d₄) δ 8.10 (s, 1H), 7.53 (t, J=7.0 Hz, 1H), 7.35-7.19 (m, 3H), 6.25 (d, J=4.0 Hz, 1H), 4.76 (t, J=4.6 Hz, 1H), 4.74-4.58 (m, 2H), 4.52 (t, J=5.2 Hz, 1H), 4.50-4.38 (m, 2H), 4.22 (q, J=5.2 Hz, 1H), 3.79 (dd, J=10.5, 4.6 Hz, 1H), 3.71 (dd, J=10.5, 6.0 Hz, 1H), 3.62 (dd, J=9.0, 1.7 Hz, 2H), 3.01 (t, J=7.1 Hz, 2H), 2.54 (q, J=7.5 Hz, 2H). ³¹P NMR (203 MHz, Methanol-d₄) δ 14.89 (s).

Examples 3 and 4

((((((2R,3S,4R,5R)-5-(6-chloro-4-(2',3'-dihydrospiro [azetidine-3,1'-inden]-1-yl)-1H-pyrazolo[3,4-d]pyrimidin-1-yl)-3,4-dihydroxytetrahydrofuran-2-yl) methoxy)methyl)(hydroxy)phosphoryl)oxy)methyl isopropyl carbonate 3 and ((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl) phosphoryl)bis(oxy))bis(methylene) diisopropyl decarbonate 4

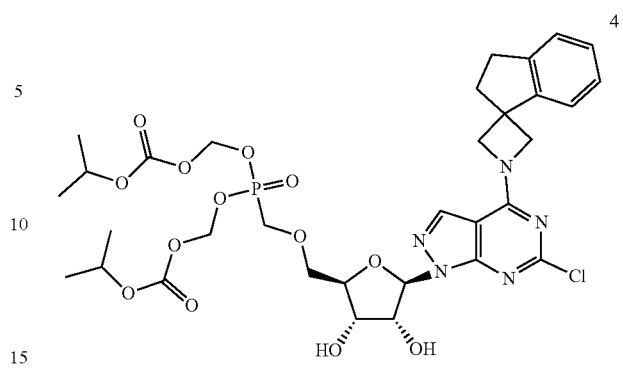

4

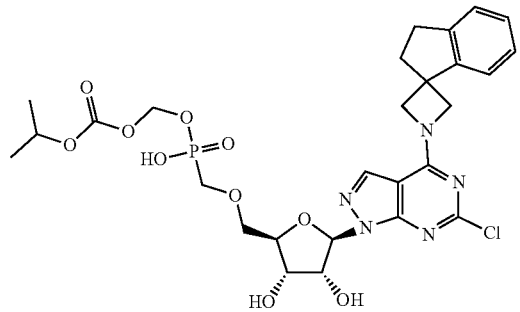

3 and

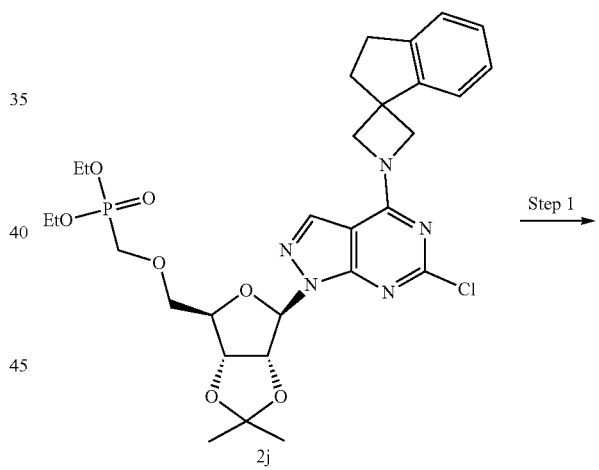

2j

Step 1

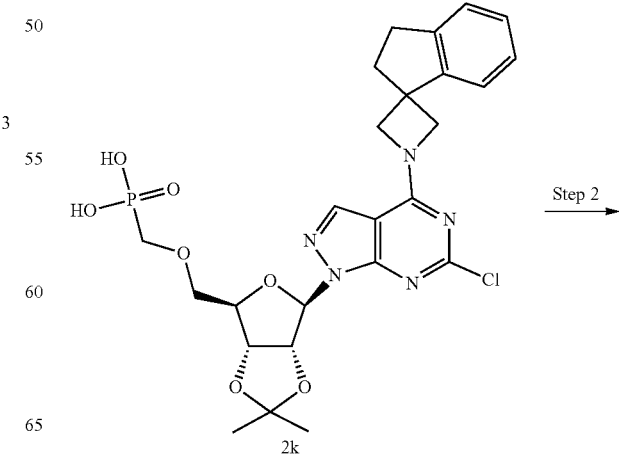

2k

Step 2

-continued

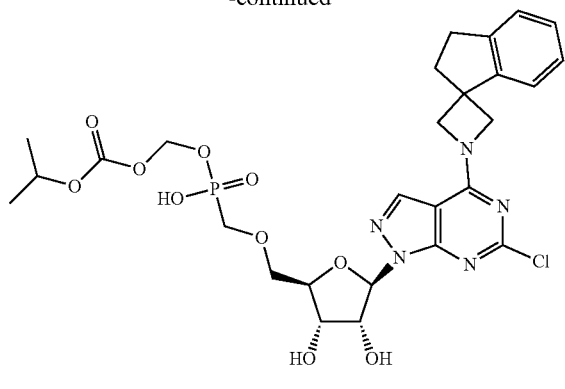

3

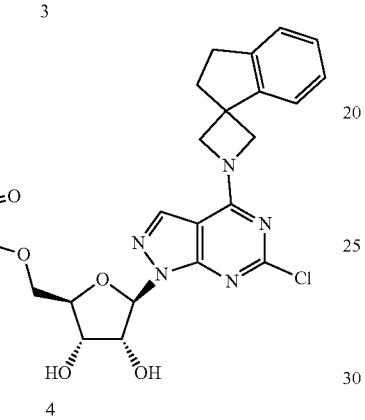

4

Step 1

(((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl)phosphonic acid 2k A dried round-bottom flask was charged with 2j (478 mg, 0.75 mmol) and DCM (10 mL). The resulted solution was cooled down to 0° C. before addition of TMSBr (1.0 mL, 7.54 mmol) dropwise. After 3 h stirring at 0° C., the reaction mixture was concentrated by rotavapor and further dried in vacuum. The resulted residue was taken up into ice-cold DCM before addition into a solution of NH$_4$HCO$_3$ (119 mg, 1.51 mmol) in H$_2$O (3 mL) dropwise at 0° C. After 30 min stirring at 0° C., the mixture was purified by HPLC with 40-90% MeOH in H$_2$O as eluent to give 2k as white solids (210 mg, 49%), MS (ESI): m/z=578 [M+1].

Step 2

((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)(hydroxy)phosphoryl)oxy)methyl isopropyl carbonate 3 and ((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphoryl)bis(oxy))bis(methylene) diisopropyl decarbonate 4

A dried round-bottom flask was charged with 2k (180 mg, 0.31 mmol), chloromethyl isopropyl carbonate (285 mg, 1.87 mmol), n-Bu$_4$NBr (400 mg, 1.24 mmol) and N-methyl pyrrolidinone (1.5 m), followed by addition of Et$_3$N (0.13 mL, 0.93 mmol) at room temperature. After 4 h stirring at 55° C., the reaction mixture was cooled to room temperature, diluted with H$_2$O (10 m), and extracted with EtOAc (2×50 m). The combined organic phases were washed with brine, dried over anhydrous MgSO$_4$, filtered, concentrated by rotavapor, and further dried in vacuum. The resulted residue was taken up into ice-cooled TFA (0.47 mL with 5% H$_2$O). After 1 h stirring at 0° C., the reaction mixture was slowly dropped into a solution of NaHCO$_3$ (822 mg) in H$_2$O (15 mL) at 0° C. and stirred at room temperature for 15 mins. The resulting mixture was purified by HPLC with 30-80% MeCN in H$_2$O to give 3 as white solids (32 mg, yield: 16%), MS (ESI): m/z=654 [M+1] and 4 as white solids (16 mg, yield: 7%), MS (ESI): m/z=770 [M+1], respectively.

Example 5

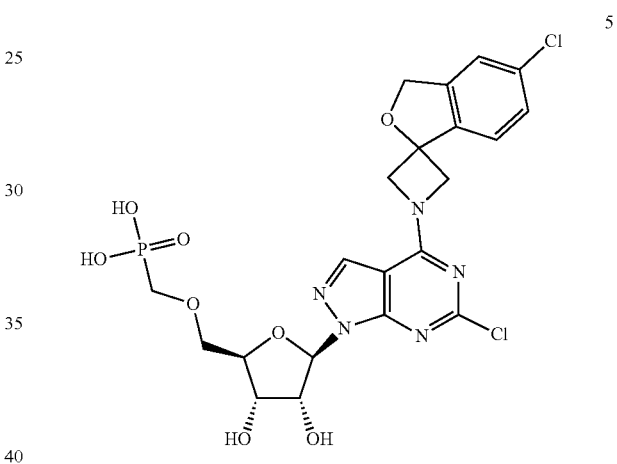

5

(((((2R,3S,4R,5R)-5-(6-chloro-4-(5'-chloro-3'H-spiro[azetidine-3,1'-isobenzofuran]-1-yl)-1H-pyrazolo[3,4-d]pyrimidin-1-yl)-3,4-dihydroxytetrahydrofuran-2-yl)methoxy)methyl)phosphonic acid 5

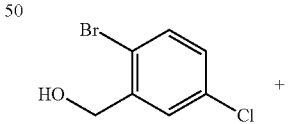

5a

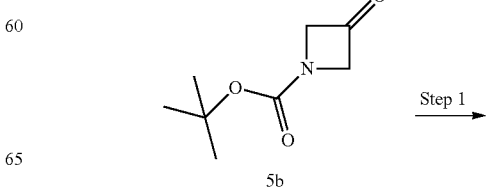

5b

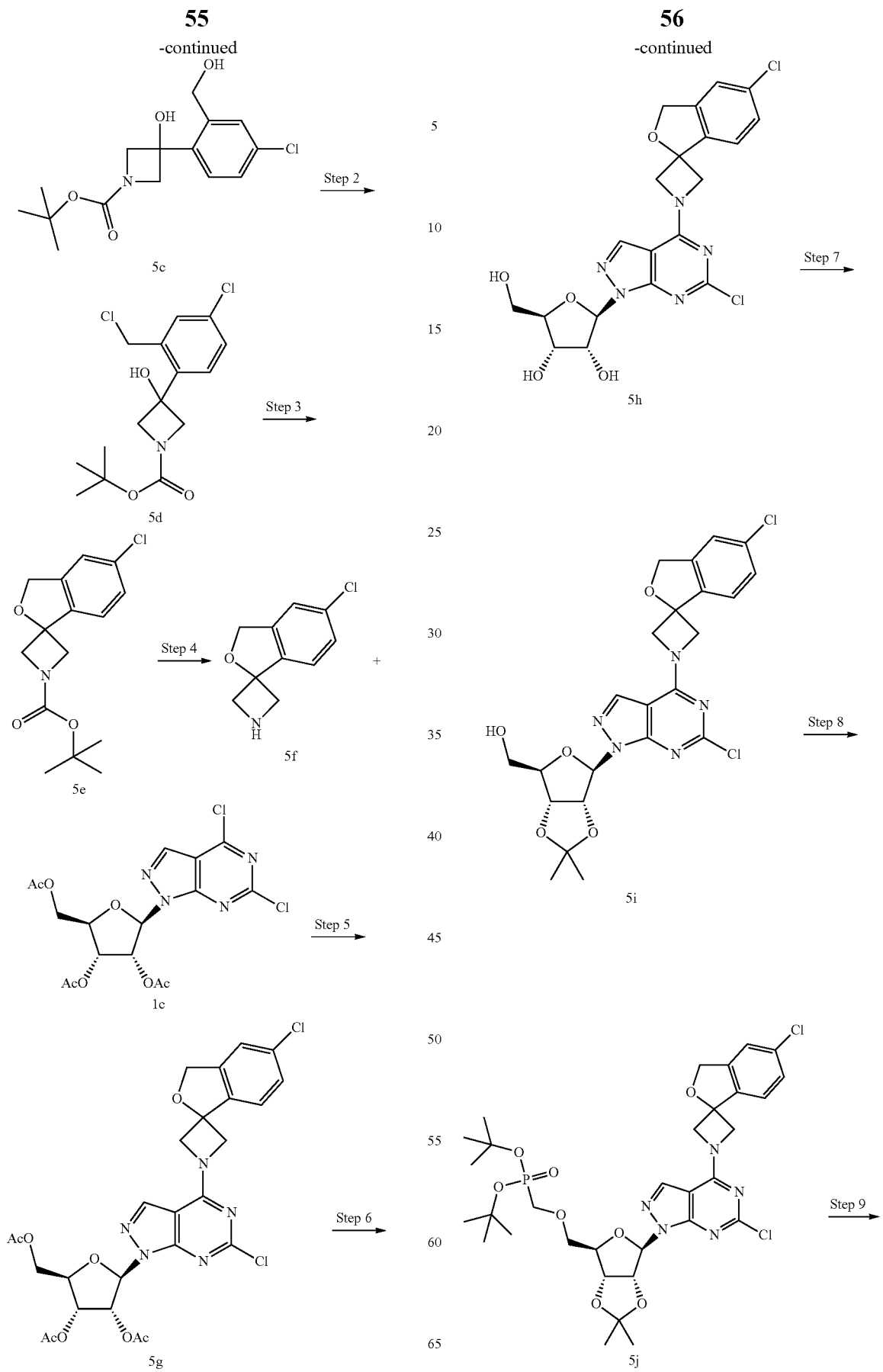

-continued

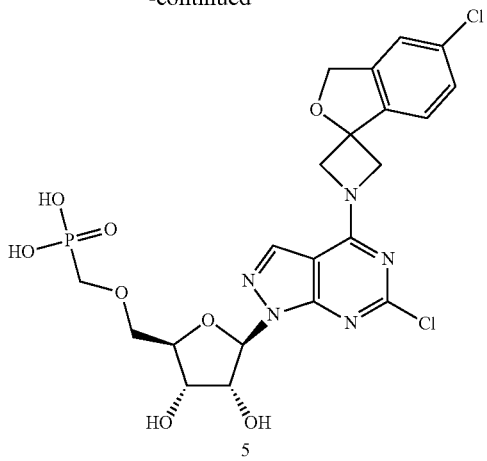

5

Step 1 tert-Butyl 3-(4-chloro-2-(hydroxymethyl)phenyl)-3-hydroxyazetidine-1-carboxylate 5c To a solution of (2-bromo-5-chlorophenyl)methanol 5a (2.00 g, 9.03 mmol) in anhydrous THF (20 mL) at −78° C. was added n-butyllithium (8.50 mL, 1.6M in hexane, 13.60 mmol) dropwise. After 1 h stirring at −78° C., to the reaction mixture was added a solution of N-Boc-3-azetidinone 5b (1.60 g, 9.35 mmol) in anhydrous THF (5 mL). The reaction mixture was warmed to room temperature and stirred for 16 hrs. The reaction mixture was quenched with ice-cold aqueous NH$_4$Cl solution (10 mL, 10%), extracted with ethyl acetate (3×50 mL). The combined organic phases were washed with brine, dried over anhydrous sodium sulfate, filtered, and concentrated under vacuum. The resulting residue was purified by column chromatography on silica gel (EtOAc:hexanes=3:7) to afford 5c (0.50 g, yield: 17.6%). MS (ESI): m/z=314 [M+1].

Step 2 tert-Butyl 3-(4-chloro-2-(chloromethyl)phenyl)-3-hydroxyazetidine-1-carboxylate 5d To a solution of tert-butyl 3-(4-chloro-2-(hydroxymethyl)phenyl)-3-hydroxyazetidine-1-carboxylate 5c (0.5 g, 1.59 mmol) in DCM (10 mL) were added solution methanesulfonyl chloride (0.537 mL, 6.94 mmol) and triethylamine (1.095 mL, 8.01 mmol) at room temperature. After 3 h stirring at room temperature, to the reaction mixture was added saturated aqueous ammonium chloride solution and extracted with DCM. The organic layer was washed with brine, dried over anhydrous sodium sulfate, filtered, and then concentrated under vacuum. The residue was purified by column chromatography on silica gel (EtOAc:hexanes=3:7) to afford 5d (0.1 g, yield: 18.9%). MS (ESI): m/z=333 [M+1].

Step 3 tert-butyl 5'-chloro-3'H-spiro[azetidine-3,1'-isobenzofuran]-1-carboxylate 5e To a solution of tert-butyl 3-(4-chloro-2-(chloromethyl)phenyl)-3-hydroxyazetidine-1-carboxylate (0.1 g, 0.30 mmol) 5d in THF (5 mL) was added sodium hydride (27 mg, 0.70 mmol, 60% in mineral oil) in small portions at 0° C. The resulted mixture was stirred at room temperature for 2 hrs, was then quenched by ice water followed by extraction with EtOAc (3×25 mL). The combined organic layers were washed with water and brine, dried over anhydrous sodium sulfate, filtered, and concentrated under vacuum. The residue was purified by column chromatography on silica gel (EtOAc:hexanes=3:7) to afford 5e (80 mg, yield: 90%). MS (ESI): m/z=296 [M+1].

Step 4

5'-chloro-3'H-spiro[azetidine-3,1'-isobenzofuran] 5f

A solution of tert-butyl 5'-chloro-3'H-spiro[azetidine-3,1'-isobenzofuran]-1-carboxylate 5e (80 mg, 0.27 mmol) and trifluoroacetic acid (1 mL) in DCM (2 mL) was stirred at room temperature for 2 hrs. The solution was concentrated in vacuo to afford 5f (50 mg, yield: 95%). MS (ESI): m/z=196.0 [M+1].

Step 5

(2R,3R,4R,5R)-2-(acetoxymethyl)-5-(6-chloro-4-(5'-chloro-3'H-spiro[azetidine-3,1'-isobenzofuran]-1-yl)-1H-pyrazolo[3,4-d]pyrimidin-1-yl)tetrahydrofuran-3,4-diyl diacetate 5 g To a solution of 5'-chloro-3'H-spiro[azetidine-3,1'-isobenzofuran] 5f (50 mg, 0.26 mmol) in ethanol (10 mL) was added (2R,3R,4R,5R)-2-(acetoxymethyl)-5-(4,6-dichloro-1H-pyrazolo[3,4-d]pyrimidin-1-yl)tetrahydrofuran-3,4-diyl diacetate 1e (125 mg, 0.28 mmol) and DIPEA (50 mg, 0.39 mmol) at 0° C. The reaction mixture was stirred at 0° C. for 15 mins then at room temperature for 3.0 hrs. The reaction mixture was concentrated under vacuum and the residue was purified by column chromatography on silica-gel (EtOAc:hexanes=1:1) to afford 5 g (146 mg, yield: 93%). MS (ESI): m/z=606 [M+1].

Step 6

(2R,3R,4S,5R)-2-(6-chloro-4-(5'-chloro-3'H-spiro[azetidine-3,1'-isobenzofuran]-1-yl)-1H-pyrazolo[3,4-d]pyrimidin-1-yl)-5-(hydroxymethyl)tetrahydrofuran-3,4-diol 5 h To a solution of (2R,3R,4R,5R)-2-(acetoxymethyl)-5-(6-chloro-4-(5'-chloro-3'H-spiro[azetidine-3,1'-isobenzofuran]-1-yl)-1H-pyrazolo[3,4-d]pyrimidin-1-yl)tetrahydrofuran-3,4-diyl diacetate 5 g (230 mg, 0.38 mmol) in ethanol (15 mL) was added DBU (116 mg, 0.76 mmol) at room temperature. After 1 h stirring at room temperature, the reaction mixture was concentrated under vacuum and the residue was purified by column chromatography on silica-gel (EtOAc:hexanes=4:1) to give 5 h (135 mg, yield: 74%). MS (ESI): m/z=480.0 [M+1].

Step 7

((3aR,4R,6R,6aR)-6-(6-chloro-4-(5'-chloro-3'H-spiro[azetidine-3,1'-isobenzofuran]-1-yl)-1H-pyrazolo[3,4-d]pyrimidin-1-yl)-2,2-dimethyltetrahydrofuro[3,4-d][1,3]dioxol-4-yl)methanol 5i To a solution of (2R,3R,4S,5R)-2-(6-chloro-4-(5'-chloro-3'H-spiro[azetidine-3,1'-isobenzofuran]-1-yl)-1H-pyrazolo

[3,4-d]pyrimidin-1-yl)-5-(hydroxymethyl)tetrahydrofuran-3,4-diol 5 h (135 mg, 0.28 mmol) in acetone (5 mL) was added 2,2-dimethoxypropane (43.9 mg, 0.42 mmol) and p-TsOH monohydrate (71.7 mg, 0.42 mmol) at room temperature. After 2 h stirring at room temperature, the reaction was neutralized by Et₃N (200 μL) and concentrated under vacuum. The crude product was purified by column chromatography on silica-gel (75% to 100% of EtOAc in hexanes) giving 5i (88 mg, yield: 60.2%). MS (ESI): m/z=520 [M+1].

Step 8 di-tert-butyl ((((3aR,4R,6R,6aR)-6-(6-chloro-4-(5'-chloro-3'H-spiro[azetidine-3,1'-isobenzofuran]-1-yl)-1H-pyrazolo[3,4-d]pyrimidin-1-yl)-2,2-dimethyltetrahydrofuro[3,4-d][1,3]dioxol-4-yl)methoxy)methyl)phosphonate 5j To a solution of ((3aR,4R,6R,6aR)-6-(6-chloro-4-(5'-chloro-3'H-spiro[azetidine-3,1'-isobenzofuran]-1-yl)-1H-pyrazolo[3,4-d]pyrimidin-1-yl)-2,2-dimethyltetrahydrofuro[3,4-d][1,3]dioxol-4-yl)methanol 5i (88 mg, 0.17 mmol) in anhydrous DMF (2.5 mL) was added (di-tert-butoxyphosphoryl)methyl 4-nitrobenzenesulfonate (104 mg, 0.25 mmol) and magnesium 2-methylpropan-2-olate (72.1 mg, 0.42 mmol) at room temperature. The reaction mixture was stirred at 50° C. for 18 hrs, and then cooled to room temperature followed by addition of water (10 mL) and ethyl acetate (20 mL). The reaction mixture was passed through a short pad of celite. The organic layer was separated, washed with brine, dried over sodium sulfate, filtered and concentrated in vacuo. The residue was purified by flash chromatography on silica gel (DCM:methanol=10:1) to give 5j (80 mg, yield: 65%). MS (ESI): m/z=726 [M+1].

Step 9

(((((2R,3S,4R,5R)-5-(6-chloro-4-(5'-chloro-3'H-spiro[azetidine-3,1'-isobenzofuran]-1-yl)-1H-pyrazolo[3,4-d]pyrimidin-1-yl)-3,4-dihydroxytetrahydrofuran-2-yl)methoxy)methyl)phosphonic acid 5

To a solution of di-tert-butyl((((3aR,4R,6R,6aR)-6-(6-chloro-4-(5'-chloro-3'H-spiro[azetidine-3,1'-isobenzofuran]-1-yl)-1H-pyrazolo[3,4-d]pyrimidin-1-yl)-2,2-dimethyltetrahydrofuro[3,4-d][1,3]dioxol-4-yl)methoxy)methyl)phosphonate 5j (80 mg, 0.11 mmol) was dissolved in DCM (2 mL) was added TFA (0.5 mL) and water (0.5 mL). The reaction mixture was stirred at room temperature for 0.5 hrs. The reaction mixture was concentrated in vacuo. The resulted residue was diluted with MeOH (2 mL) and neutralized with 7.0 M NH3 in MeOH (2 mL) to pH7.0. The mixture was concentrated in vacuo and the residue was purified by reverse phase HPLC (C-18 column, 0 to 30% gradient of acetonitrile and water with 0.1% HCOOH) to give 5 as yellow solids (20 mg, yield: 32%): $^1$H NMR (400 MHz, Methanol-d4) δ 8.09 (s, 1H), 7.58 (s, 1H), 7.41 (d, J=8.3 Hz, 1H), 7.36 (s, 1H), 6.24 (s, 1H), 5.17 (s, 2H), 4.82 (brs, 2H), 4.74 (t, J=4.8 Hz, 1H), 4.62 (brs, 2H), 4.50 (t, J=5 Hz, 1H), 4.22-4.18 (m, 1H), 3.79-3.75 (m, 1H), 3.71-3.67 (m, 1H), 3.00 (s, 1H), 2.86 (s, 1H). MS (ESI): m/z=574 [M+1].

Example 6

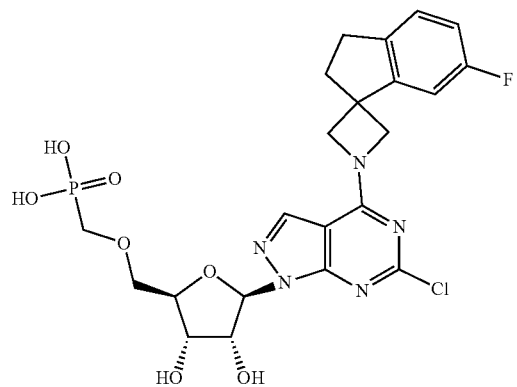

(((((2R,3S,4R,5R)-5-(6-chloro-4-(6'-fluoro-2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 6

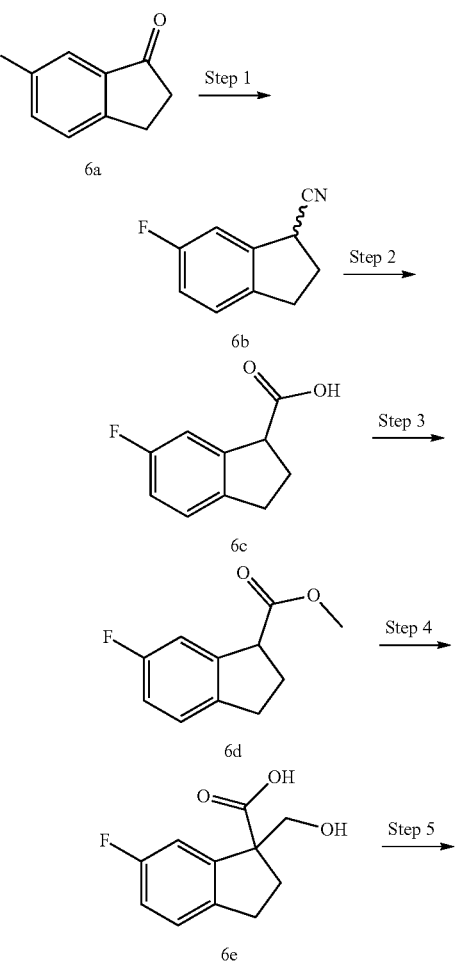

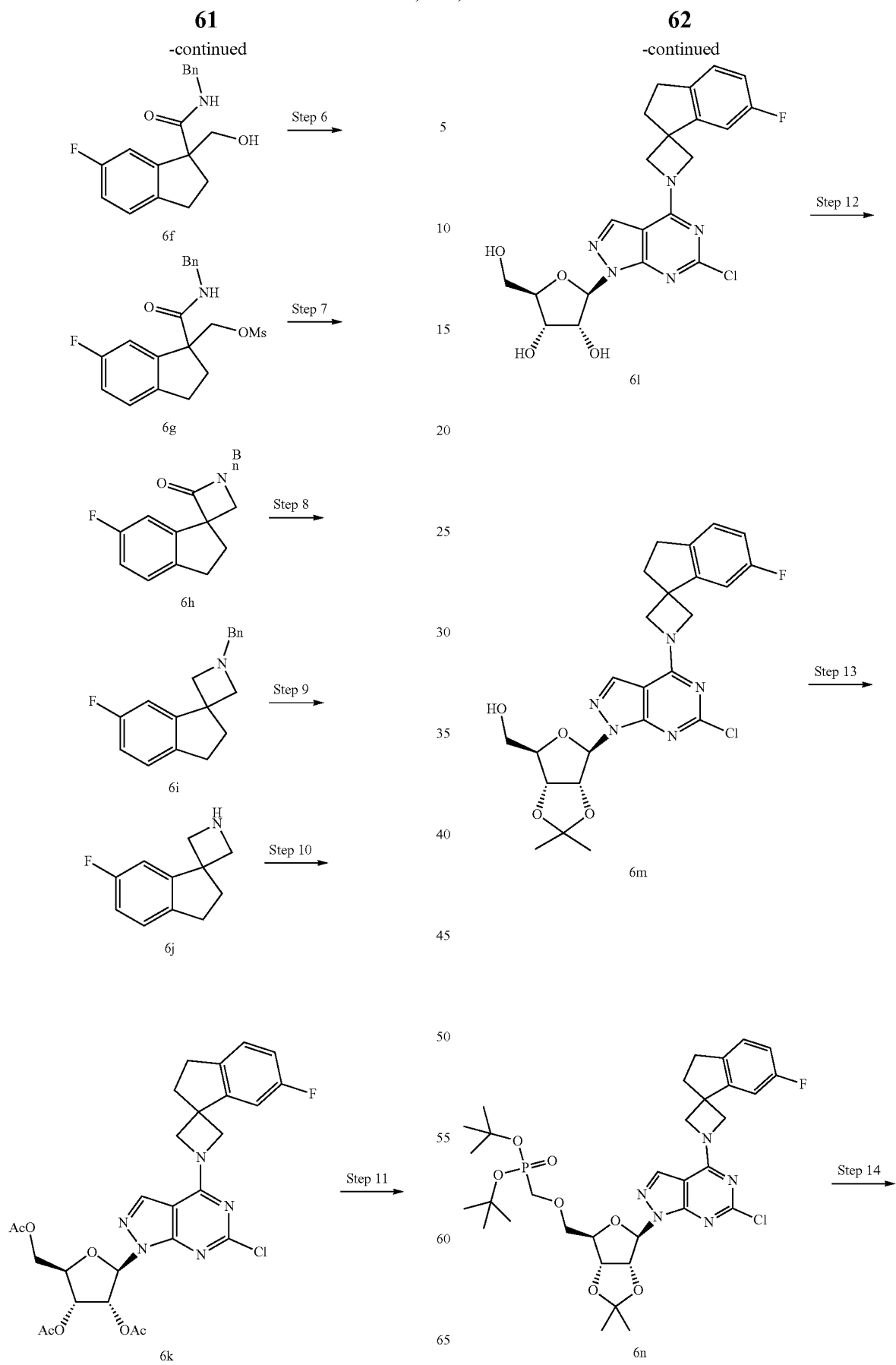

-continued

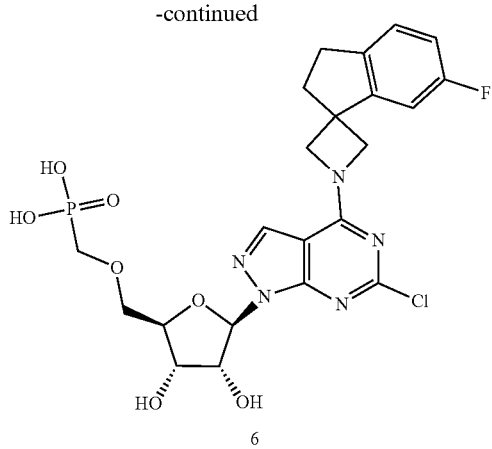

6

Step 1

6-fluoro-2,3-dihydro-1H-indene-1-carbonitrile 6b

To a solution of 6-fluoro-2,3-dihydro-1H-inden-1-one 6a (20.0 g, 133.2 mmol) in THF-Ethanol (100 mL, 1:1) was added potassium tert-butoxide (30.0 g, 267.4 mmol) in THF (35 mL) at 0° C. The reaction mixture was warmed to 20° C. followed by addition of p-tolylsulfonylmethyl isocyanide (40.0 g, 204.88 mmol) in small portions in 1 h. The reaction mixture was continued to stir for 16 hrs at the same temperature, and then cooled to 0° C. before addition of brine (100 mL) with vigorous stirring. The mixture was poured into brine (500 mL) and extracted with EtOAc (4×250 mL). The combined organic phases were dried over anhydrous sodium sulfate, filtered, and concentrated in vacuo. The residue was purified by column chromatography on silica gel to afford 6b (13.0 g, yield: 60.6%). $^1$H NMR (400 MHz, CDCl3) δ 7.27-7.21 (m, 1H), 7.15-7.12 (m, 1H), 7.00-6.99 (m, 1H), 4.10 (t, J=8.3 Hz, 1H), 3.06-3.00 (m, 1H), 2.95-2.85 (m, 1H), 2.65-2.60 (m, 1H), 2.47-2.40 (m, 1H).

Step 2

6-fluoro-2,3-dihydro-1H-indene-1-carboxylic acid 6c

A mixture of 6-fluoro-2,3-dihydro-1H-indene-1-carbonitrile 6b (5.0 g, 31.0 mmol) and sodium hydroxide (2.50 g, 62.5 mmol) in water (50 mL) was heated to reflux for 5.0 hrs. After cooled to room temperature, the solution was extracted with EtOAc (2×25 mL). The aqueous phase was diluted with water (50 mL) and adjusted the pH value to 2-3 at 0° C. by careful addition of concentrated hydrochloric acid. The resulted cloudy mixture was extracted with DCM (50 mL), and the DCM layer was dried over anhydrous sodium sulfate, filtered, and concentrated in vacuo. The residue was purified by column chromatography on silica gel with hexane/EtOAc eluent to afford 6c (5.0 g, yield: 89.5%). MS (ESI): m/z=179 [M−1].

Step 3 methyl 6-fluoro-2,3-dihydro-1H-indene-1-carboxylate 6d

To a solution of 6-fluoro-2,3-dihydro-1H-indene-1-carboxylic acid 6c (5.0 g, 27.8 mmol) in DCM (25 mL) and pyridine (220 mg, 2.78 mmol) was added thionyl chloride (2.01 mL, 27.8 mmol) at 0° C. The solution was stirred at room temperature for 2.0 hrs before addition of methanol (25 mL). After additional 2 h stirring at room temperature, the reaction mixture was concentrated in vacuo. The resulted residue was purified by column chromatography on silica gel (EtOAc:hexanes=1:2) to afford 6d (5.20 g, yield: 96.5%).

Step 4

6-fluoro-1-(hydroxymethyl)-2,3-dihydro-1H-indene-1-carboxylic acid 6e

A mixture of methyl 6-fluoro-2,3-dihydro-1H-indene-1-carboxylate 6d (2.0 g, 10.30 mmol), formaldehyde (1.75 g, 20.75 mmol, 38% in water) and potassium carbonate (4.3 g, 31.1 mmol) in DMSO (20 ml) was stirred at room temperature for 16 hrs. Then the mixture was poured into ice water (50 mL) and extracted with EtOAc (3×25 mL). The combined organic phases were dried on anhydrous sodium sulfate, filtered, and concentrated in vacuo. The resulted residue was purified by column chromatography on silica gel (EtOAc:hexanes=1:2) to afford 6e (2.1 g, yield: 97.1%). MS (ESI): m/z=209 [M−1].

Step 5

N-benzyl-6-fluoro-1-(hydroxymethyl)-2,3-dihydro-1H-indene-1-carboxamide 6f

To a solution of 6-fluoro-1-(hydroxymethyl)-2,3-dihydro-1H-indene-1-carboxylic acid 6e (2.1 g, 10.0 mmol) in DMF (25 mL) was added phenylmethanamine (1.2 g, 11.2 mmol), DIPEA (1.95 g, 15.1 mmol), and HATU (3.6 g, 15.3 mmol). The reaction mixture was stirred at room temperature for 16 hrs, and partitioned between DCM and water. The organic layers were washed with brine (50 mL), dried over anhydrous sodium sulfate, filtered, and concentrated in vacuo. The residue was purified by column chromatography on silica gel (10% MeOH in DCM) to afford 6f (2.70 g, yield: 90.3%). MS (ESI): m/z=300 [M+1].

Step 6

(1-(benzylcarbamoyl)-6-fluoro-2,3-dihydro-1H-inden-1-yl)methyl methanesulfonate 6 g To a solution of N-benzyl-6-fluoro-1-(hydroxymethyl)-2,3-dihydro-1H-indene-1-carboxamide 6f (2.70 g, 9.02 mmol) in DCM (40 mL) was added triethylamine (1.89 mL, 13.54 mmol) and methanesulfonyl chloride (0.89 mL, 11.35 mmol) in sequence at 0-5° C. After 12 h stirring at room temperature, the reaction mixture was poured into ice water (50 mL) and extracted with DCM (3×25 mL). The combined organic phases were washed with saturated aqueous NaHCO3 solution, brine, dried over anhydrous sodium sulfate, and concentrated in vacuo. The residue was purified by column chromatography on silica gel (hexanes:EtOAc=6:1) to give 6 g (3.0 g, yield: 88.2%). MS (ESI): m/z=378 [M+1].

Step 7

1-benzyl-6'-fluoro-2',3'-dihydrospiro[azetidine-3,1'-inden]-2-one 6 h

To a solution of (1-(benzylcarbamoyl)-6-fluoro-2,3-dihydro-1H-inden-1-yl)methyl methanesulfonate 6 g (3.0 g, 7.95 mmol) in acetonitrile (25 ml) was added potassium carbonate (2.2 g, 15.92 mmol). After 16 h stirring at room temperature, the mixture was poured into ice water (50 mL) and extracted with EtOAc (3×25 mL). The combined organic phases were dried on anhydrous sodium sulfate, filtered, and concentrated in vacuo. The residue was purified by column chromatography on silica gel (EtOAc:hexanes=1:2) to afford 6 h (2.0 g, yield: 89.5%). MS (ESI): m/z=282 [M+1].

Step 8

1-benzyl-6'-fluoro-2',3'-dihydrospiro[azetidine-3,1'-indene] 6i

To a solution of aluminum chloride (0.95 g, 7.15 mmol) in THF (10 mL) was added lithium aluminum hydride (4.36 mL, 10.91 mmol, 2.5 M in THF) at 0° C. The mixture was stirred at 0° C. for 30 min. To the mixture was added a solution of 1-benzyl-6'-fluoro-2',3'-dihydrospiro[azetidine-3, 1'-inden]-2-one 6 h (1.0 g, 3.55 mmol) in THF (5 mL) dropwise at 0° C. The reaction mixture was stirred at 25° C. for 16 hrs before addition of water (25 mL), aqueous sodium hydroxide solution (15%, 25 mL), water (75 mL) dropwise at 0° C. After 10 min stirring at 0° C., to the mixture was added EtOAc (50 mL) and filtered through celite. The organic layer of the filtrate was separated and the aqueous layer was extracted with EtOAc (2×50 mL). The organic layers were combined, washed with water (50 mL), brine (50 mL), dried over anhydrous sodium sulfate, filtered, and concentrated in vacuo. The residue was purified by column chromatography on silica gel (EtOAc:hexanes=1:1) to afford 6i (0.66 g, yield: 69.6%). MS (ESI): m/z=268 [M+1].

Step 9

6'-fluoro-2',3'-dihydrospiro[azetidine-3,1'-indene] 6j

To a solution of 1-benzyl-6'-fluoro-2',3'-dihydrospiro[azetidine-3,1'-indene] 6i (0.53 g, 1.98 mmol) in methanol (20 ml) was added dihydroxypalladium (278 mg, 395.9 umol, 20% on carbon, wetted with ca. 50% Water), and ammonium formate (150 mg, 2.38 mmol). The reaction mixture was stirred under a balloon of hydrogen gas at 60° C. for 16 hrs. The reaction mixture was filtered, washed with methanol (30 mL). The filtrate was concentrated in vacuo and purified by column chromatography on silica gel (EtOAc:hexanes=1:1) to afford 6j (0.2 g, yield: 57%) MS (ESI): m/z=178 [M+1].

Step 10

(2R,3R,4R,5R)-2-(acetoxymethyl)-5-(6-chloro-4-(6'-fluoro-2',3'-dihydrospiro[azetidine-3,1'-inden]-1-yl)-1H-pyrazolo[3,4-d]pyrimidin-1-yl)tetrahydrofuran-3,4-diyl diacetate 6k To a solution of 6'-fluoro-2',3'-dihydrospiro[azetidine-3, 1'-indene] 6j (0.26 g, 1.47 mmol in ethanol (10 mL) was added (2R,3R,4R,5R)-2-(acetoxymethyl)-5-(4,6-dichloro-1H-pyrazolo[3,4-d]pyrimidin-1-yl)tetrahydrofuran-3,4-diyl diacetate 1e (660 mg, 1.48 mmol) and DIPEA (285 mg, 2.21 mmol) at 0° C. The reaction mixture was stirred at 0° C. for 15 min then at room temperature for 3.0 hrs. The reaction mixture was concentrated in vacuo and the residue was purified by column chromatography on silica gel (EtOAc: hexanes=1:1) to afford 6k (0.73 g, yield: 84.5%). MS (ESI): m/z=588 [M+1].

Step 11

Synthesis of (2R,3R,4S,5R)-2-(6-chloro-4-(6'-fluoro-2',3'-dihydrospiro[azetidine-3,1'-inden]-1-yl)-1H-pyrazolo[3,4-d]pyrimidin-1-yl)-5-(hydroxymethyl)tetrahydrofuran-3,4-diol 6l To a solution of (2R,3R,4R,5R)-2-(acetoxymethyl)-5-(6-chloro-4-(6'-fluoro-2',3'-dihydrospiro[azetidine-3,1'-inden]-1-yl)-1H-pyrazolo[3,4-d]pyrimidin-1-yl)tetrahydrofuran-3,4-diyl diacetate 6k (730 mg, 1.24 mmol) in ethanol (25 mL) was added DBU (0.47 g, 0.87 mmol) at room temperature. After 1.0 h stirring at room temperature, the reaction mixture was concentrated in vacuo and the residue was purified by column chromatography on silica gel (EtOAc:hexanes=4:1) to give 6l (400 mg, 70%). MS (ESI): m/z=462 [M+1]

Step 12

Synthesis of ((3aR,4R,6R,6aR)-6-(6-chloro-4-(6'-fluoro-2',3'-dihydrospiro[azetidine-3,1'-inden]-1-yl)-1H-pyrazolo[3,4-d]pyrimidin-1-yl)-2,2-dimethyltetrahydrofuro[3,4-d] [1,3]dioxol-4-yl)methanol 6m A solution of (2R,3R,4S,5R)-2-(6-chloro-4-(6'-fluoro-2',3'-dihydrospiro[azetidine-3,1'-inden]-1-yl)-1H-pyrazolo[3,4-d]pyrimidin-1-yl)-5-(hydroxymethyl)tetrahydrofuran-3,4-diol 6l (400 mg, 0.87 mmol), 2,2-dimethoxypropane (95.0 mg, 0.91 mmol) and p-TsOH (165.0 mg, 0.96 mmol) in acetone (15 mL) was stirred at room temperature for 2 hrs. The reaction mixture was neutralized by Et3N (200 μL) and concentrated in vacuo. The residue was purified by flash chromatography on silica gel (75% to 100% EtOAc in hexanes) to afford 6m (360 mg, yield: 82.4%). MS (ESI): m/z=502 [M+1].

Step 13 di-tert-butyl (((((3aR,4R,6R,6aR)-6-(6-chloro-4-(6'-fluoro-2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl) phosphonate 6n A mixture of ((3aR,4R,6R,6aR)-6-(6-chloro-4-(6'-fluoro-2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methanol 6m (50 mg, 0.099 mmol), (di-tert-butoxyphosphoryl)methyl 4-nitrobenzenesulfonate (50 mg, 0.12 mmol) and magnesium 2-methylpropan-2-olate (45 mg, 0.26 mmol) in DMF (2.0 mL) was stirred at 50° C. for 18 hours. After cooled to ambient temperature, to the reaction mixture was added water (10 mL) and ETOAc (20 mL). The reaction mixture was passed through a short pad of celite. The organic layer was separated, washed with brine, dried over anhydrous sodium sulfate, filtered, and concentrated in vacuo. The residue was purified by flash chromatography on silica gel (DCM:methanol=10:1) to afford 6n (20 mg, yield: 28.5%). MS (ESI): m/z=708 [M+1].

Step 14

(((((2R,3S,4R,5R)-5-(6-chloro-4-(6'-fluoro-2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 6

To a solution of di-tert-butyl (((((3aR,4R,6R,6aR)-6-(6-chloro-4-(6'-fluoro-2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl) phosphonate 6n (20 mg, 0.03 mmol) in DCM (2 mL) was added TFA (0.5 mL) and water (0.5 mL) at room temperature. After 0.5 h stirring at room temperature, the reaction mixture was concentrated in vacuo. The residue was dissolved in methanol (2 mL) and neutralized with 7.0 M NH3 in MeOH (2 mL) to pH≈7.0. The reaction mixture was concentrated in vacuo. The residue was purified by reverse phase HPLC (C-18 column, 0 to 30% gradient of acetonitrile and water with 0.1 percent HCOOH) to give the product 6 as a yellow solid (12 mg, yield: 76.4%): $^1$H NMR (400 MHz, Methanol-$d_4$) δ 8.11 (s, 1H), 7.96-7.94 (m, 1H), 7.25 (brs, 1H), 6.23 (d, J=4 Hz, 1H), 4.50-4.43 (m, 2H), 4.23-4.15 (m, 2H), 3.79-3.73 (m, 2H), 3.64 (d, J=8.8 Hz, 2H), 3.01 (s, 2H), 2.96-2.93 (m, 2H), 2.87 (s, 2H), 2.56 (s, 2H). MS (ESI): m/z=556 [M+1].

Example 7

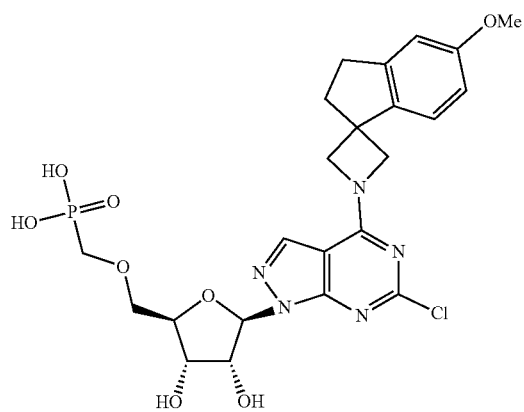

7

(((((2R,3S,4R,5R)-5-(6-chloro-4-(5'-methoxy-2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonic acid 7

The title compound was synthesized in the similar method to example 6: $^1$HNMR (400 MHz, Methanol-$d_4$) δ 8.10 (s, 1H), 7.41 (d, J=8.0 Hz, 1H), 6.92-6.81 (m, 2H), 6.21 (s, 1H), 4.71-4.58 (m, 2H), 4.49-4.40 (m, 3H), 4.24 (s, 1H), 3.79 (s, 3H), 3.75-3.61 (m, 2H), 3.01-2.86 (m, 3H), 2.56-2.43 (m, 2H), 1.30-1.26 (m, 2H). MS (ESI): m/z=566 [M-1].

Examples 8 and 9

8 and

9

((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphoryl)bis(oxy))bis(ethane-1,1-diyl)bis(2,2-dimethylpropanoate)8 and 1-((((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)(hydroxy)phosphoryl)oxy)ethyl pivalate 9

The title compounds were synthesized in the same method to examples 3 and 4: MS (ESI) m/z=794 [M+1] for compound 8 and MS (ESI) m/z=666 [M+1] for compound 9, respectively.

Examples 10 and 11
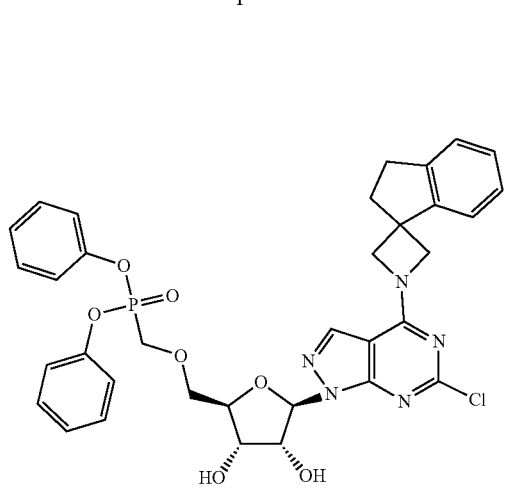
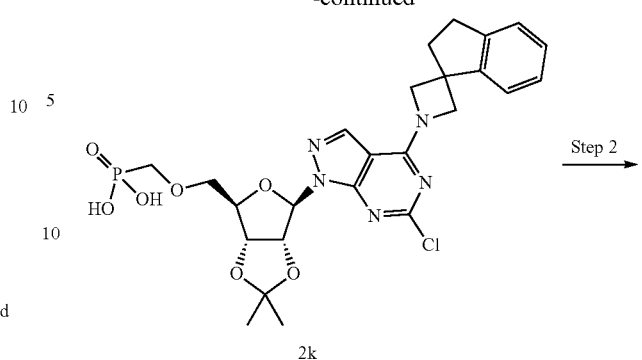
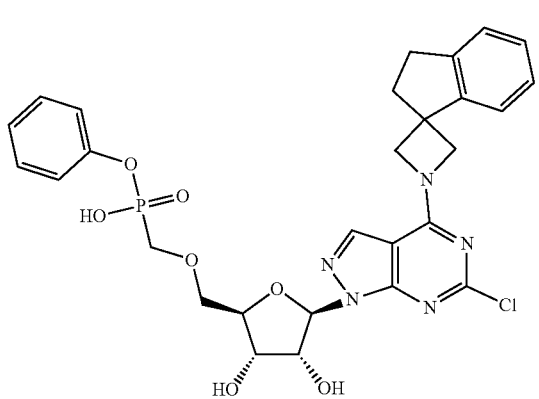
diphenyl(((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonate 10
and phenyl hydrogen ((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonate 11
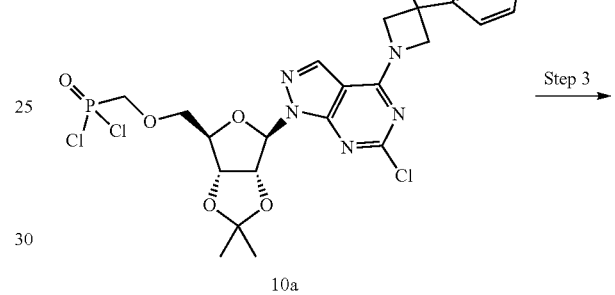
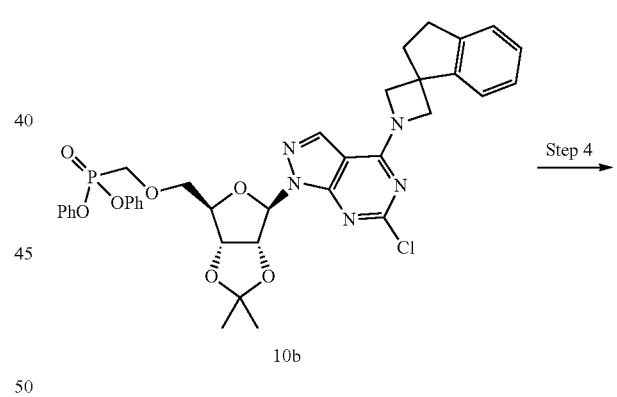
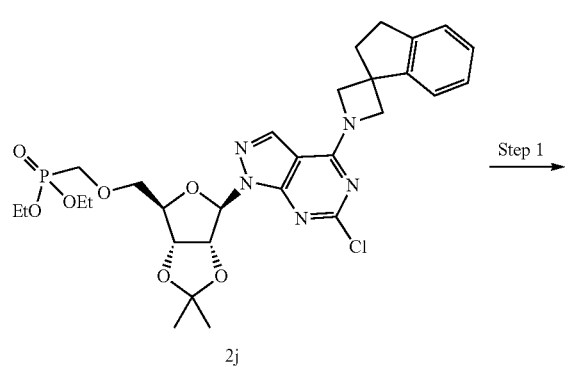
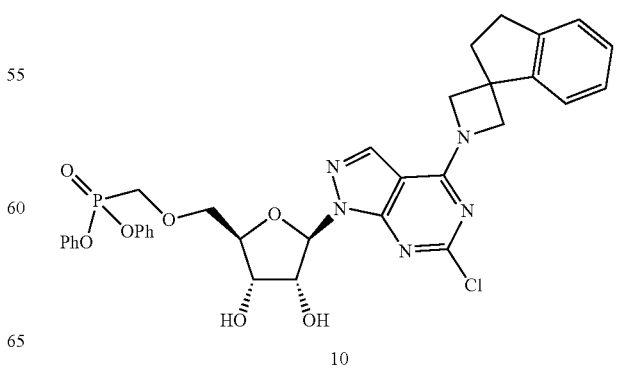

-continued

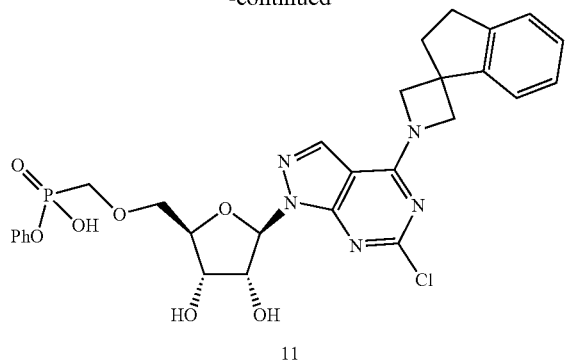

11

Step 1

(((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl)phosphonic acid 2k To a solution of diethyl (((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl)phosphonate 2j (330 mg, 0.52 mmol) in DCM (5 mL) was added TMSBr (0.64 mL, 4.89 mmol) and pyridine (0.48 mL, 5.88 mmol) at 0° C. After 3.5 h stirring at 0° C., the reaction mixture was concentrated in vacuo. The residue was purified by HPLC with 40-90% MeOH in $H_2O$ as eluent to give 2k as white solids (240 mg, 80%), MS (ESI): m/z=578 [M+1].

Step 2

(((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl)phosphonic dichloride 10a To a solution of (((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl)phosphonic acid 2k (100 mg, 0.17 mmol) in DCM (2.5 mL) was added oxalyl chloride in DCM (2M, 0.16 mL, 0.32 mmol) and DMF (2 drops) at room temperature. After 30 min stirring at room temperature, volatiles were removed in vacuo. The residue was added anhydrous toluene and evaporated in vacuo twice. Thus, the treated residue was used directly for next step without further purification.

Step 3 diphenyl (((((3aR,4R,6R,6aR)-6-(6-chloro-4-(2',3'-dihydrospiro[azetidine-3,1'-inden]-1-yl)-1H-pyrazolo[3,4-d]pyrimidin-1-yl)-2,2-dimethyltetrahydrofuro[3,4-d][1,3]dioxol-4-yl)methoxy)methyl)phosphonate 10b The residue including 10a was dissolved in DCM (1 mL) before addition of the solution of phenol (64 mg, 0.68 mmol) in DCM (1 mL) and Et3N (0.22 mL, 1.54 mmol) in sequence at 0° C. After 20 min stirring at 0° C. and 15 min stirring at room temperature, the reaction mixture was concentrated in vacuo. The residue was purified by column chromatography on silica gel (0 to 2% of methanol in DCM) to give 10b (23 mg, yield: 18.5% over 2 steps). MS (ESI): m/z=730 [M+1].

Step 4 diphenyl ((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonate 10 and phenyl hydrogen ((((2R,3S,4R,5R)-5-(6-chloro-4-(2',3'-dihydrospiro[azetidine-3,1'-inden]-1-yl)-1H-pyrazolo[3,4-d]pyrimidin-1-yl)-3,4-dihydroxytetrahydrofuran-2-yl)methoxy)methyl)phosphonate 11

To a solution of 10b (23 mg, 0.031 mmol) in DCM (1 mL) was added formic acid (80%, 0.5 mL) at 0° C. The reaction mixture was warmed to room temperature and continued to stir for 16 hrs at room temperature. The resulting mixture was purified by HPLC with 30-80% acetonitrile in water to give 10 as white solids (1.2 mg, yield: 5.6%): $^1$HNMR (400 MHz, Methanol-$d_4$) δ 7.91 (s, 1H), 7.47-7.10 (m, 14H), 6.21 (s, 1H), 4.71-4.40 (m, 6H), 4.20-4.12 (m, 3H), 3.90-3.75 (m, 2H), 3.01-2.89 (m, 2H), 2.52-2.45 (m, 2H). $^{31}$P NMR (160 MHz, Methanol-$d_4$) δ 15.68 (s). MS (ESI): m/z=690 [M+1]; and 11 as white solids (3.8 mg, yield: 20%): $^1$HNMR (400 MHz, Methanol-$d_4$) δ 8.01 (s, 1H), 7.30-7.02 (m, 9H), 6.24 (s, 1H), 4.75-4.30 (m, 6H), 4.26-4.15 (m, 1H), 3.80-3.55 (m, 4H), 3.01-2.88 (m, 2H), 2.54-2.48 (m, 2H). $^{31}$P NMR (160 MHz, Methanol-$d_4$) δ 15.53 (s). MS (ESI): m/z=614 [M+1], respectively.

Example 12

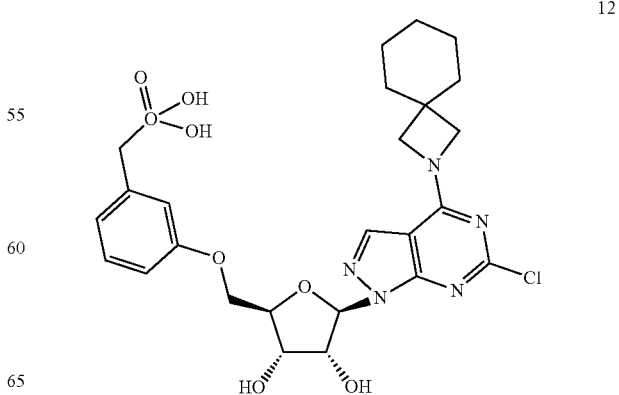

12

73

(3-(((2R,3S,4R,5R)-5-(6-chloro-4-(2-azaspiro[3.5]
nonan-2-yl)-1H-pyrazolo[3,4-d]pyrimidin-1-yl)-3,4-
dihydroxytetrahydrofuran-2-yl)methoxy)benzyl)
phosphonic acid 12

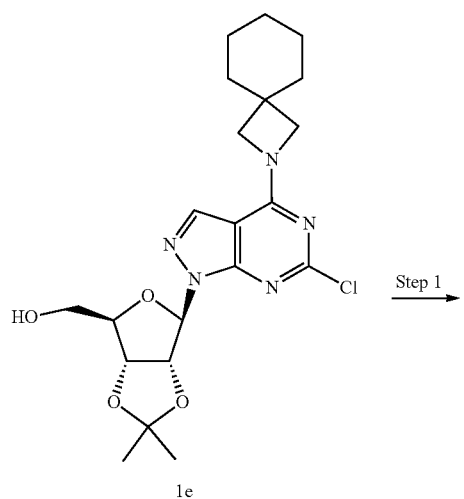

1e

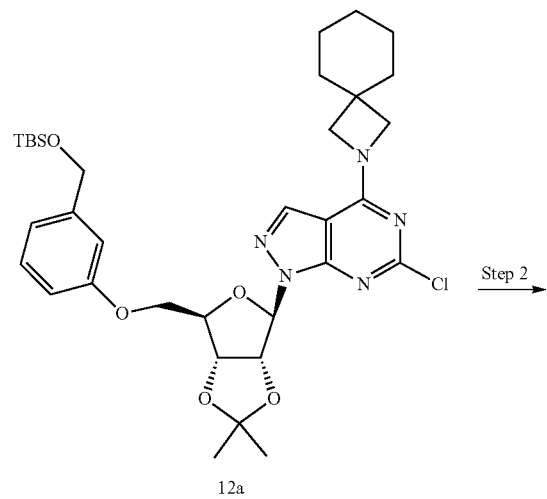

12a

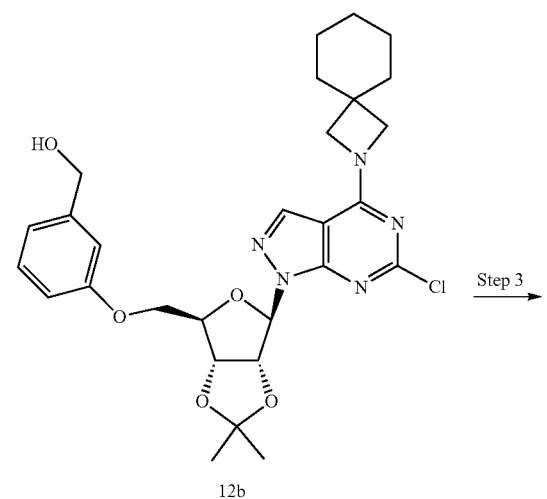

12b

74

-continued

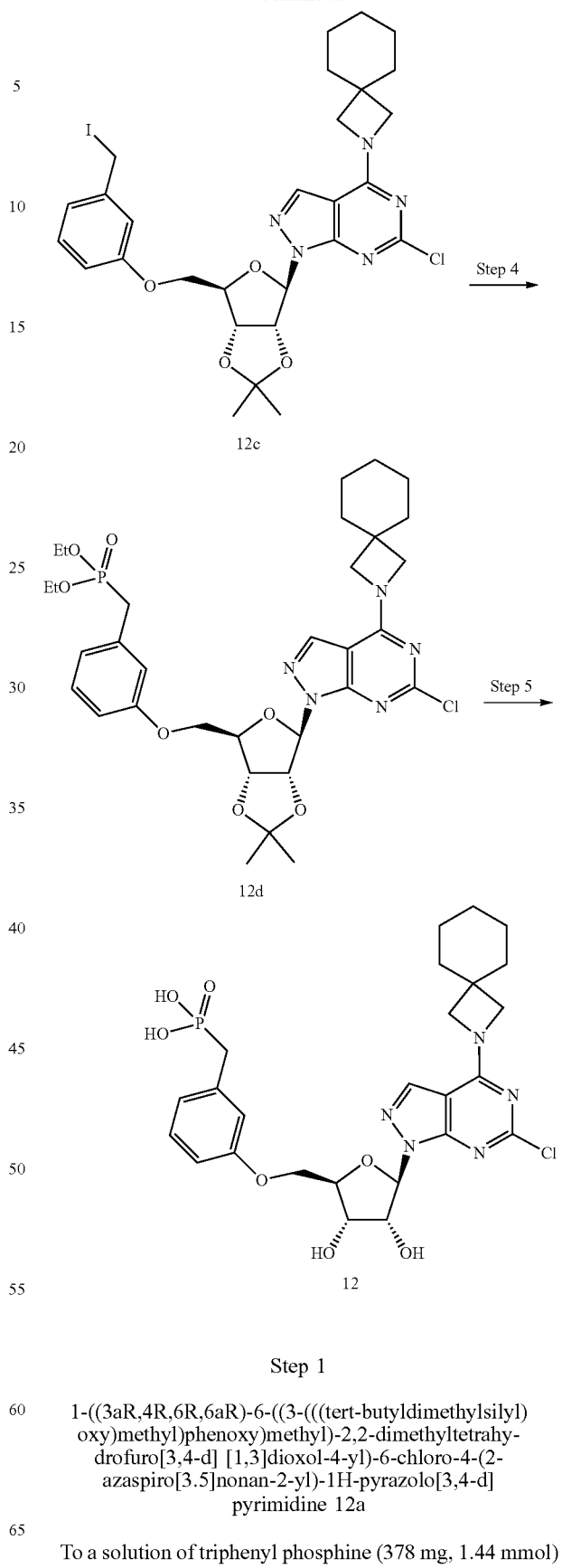

Step 1

1-((3aR,4R,6R,6aR)-6-((3-(((tert-butyldimethylsilyl)
oxy)methyl)phenoxy)methyl)-2,2-dimethyltetrahy-
drofuro[3,4-d][1,3]dioxol-4-yl)-6-chloro-4-(2-
azaspiro[3.5]nonan-2-yl)-1H-pyrazolo[3,4-d]
pyrimidine 12a To a solution of triphenyl phosphine (378 mg, 1.44 mmol)
in THF (6 mL) was added ((3aR,4R,6R,6aR)-6-(6-chloro- 4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl)methanol 1e (400 mg, 0.89 mmol) and DIAD (0.33 mL, 1.68 mmol) in sequence at room temperature. After 30 min stirring at room temperature, to the reaction mixture was added a solution of 3-(((tert-butyldimethylsilyl)oxy)methyl)phenol (217 mg, 0.91 mmol) in THF (1 mL). After refluxing for 16 hrs, the reaction mixture was cooled to room temperature and concentrated in vacuo. The residue was purified by column chromatography on silica gel (0-50% EtOAc in hexanes) to give 12a as white solids (114.5 mg, yield: 19%). MS (ESI): m/z=670 [M+1].

Step 2

(3-(((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d] [1,3]dioxol-4-yl)methoxy)phenyl)methanol 12b To a solution of 1-((3aR,4R,6R,6aR)-6-((3-(((tert-butyldimethylsilyl)oxy)methyl)phenoxy)methyl)-2,2-dimethyltetrahydrofuro[3,4-d] [1,3]dioxol-4-yl)-6-chloro-4-(2-azaspiro[3.5]nonan-2-yl)-1H-pyrazolo[3,4-d]pyrimidine 12a (170.5 mg, 0.25 mmol) in THF (1.5 mL) was added TBAF (1M in THF, 0.31 mL, 0.31 mmol) at room temperature. After 2 h stirring at room temperature, the reaction mixture was concentrated in vacuo and the residue was purified by column chromatography on silica gel (first 0-30% EtOAc in hexanes then 0-5% methanol in DCM) to give 12b as off-white solids (102 mg, yield: 72%). MS (ESI): m/z=556 [M+1].

Step 3

6-chloro-1-((3aR,4R,6R,6aR)-6-((3-(iodomethyl)phenoxy)methyl)-2,2-dimethyltetrahydrofuro[3,4-d][1,3]dioxol-4-yl)-4-(2-azaspiro[3.5]nonan-2-yl)-1H-pyrazolo[3,4-d]pyrimidine 12c To the solution of (3-(((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl)methoxy)phenyl)methanol 12b (50 mg, 0.09 mmol) in DMF (1 mL) was added methyl triphenoxy phosphonium iodide (81.4 mg, 0.18 mmol) at room temperature. After 30 min stirring at room temperature, methanol was added to the reaction mixture and the solution was stirred for 15 more minutes. The solvents were evaporated to dryness; the residue was re-dissolved in DCM and washed once with 5% aq. $Na_2S_2O_3$, then once with water. The organic layer was dried over anhydrous sodium sulfate, filtered and evaporated to dryness. The crude residue was purified by column chromatography on silica gel (0-30% EtOAc in hexanes) to give 12c as white solids (46.3 mg, yield: 77%). MS (ESI): m/z=666 [M+1].

Step 4 diethyl (3-(((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl)methoxy)benzyl)phosphonate 12d 6-Chloro-1-((3aR,4R,6R,6aR)-6-((3-(iodomethyl)phenoxy)methyl)-2,2-dimethyltetrahydrofuro[3,4-d] [1,3]dioxol-4-yl)-4-(2-azaspiro[3.5]nonan-2-yl)-1H-pyrazolo[3,4-d]pyrimidine 12c (36 mg, 0.054 mmol) was dissolved in triethyl phosphite (1 mL) and the solution was irradiated by microwave to 150° C. for 5 minutes. The solution was evaporated to dryness and the residue was purified by column chromatography on silica gel (0-50% EtOAc in hexanes) to give 12d (23 mg, yield: 63%). MS (ESI): m/z=676 [M+1].

Step 5

(3-(((2R,3S,4R,5R)-5-(6-chloro-4-(2-azaspiro[3.5]nonan-2-yl)-1H-pyrazolo[3,4-d]pyrimidin-1-yl)-3,4-dihydroxytetrahydrofuran-2-yl)methoxy)benzyl)phosphonic acid 12

To a solution of diethyl (3-(((3aR,4R,6R,6aR)-6-(6-chloro-4-(2-azaspiro[3.5]nonan-2-yl)-1H-pyrazolo[3,4-d]pyrimidin-1-yl)-2,2-dimethyltetrahydrofuro[3,4-d][1,3]dioxol-4-yl)methoxy)benzyl)phosphonate 12d (19.6 mg, 0.029 mmol) in DCM (1 mL) was added TMSBr (0.02 mL, 0.18 mmol) and pyridine (0.02 mL, 0.25 mmol) at 0° C. After 5 h stirring at 0° C., the reaction mixture was evaporated to dryness. To the residue was added an ice-cold aq. TFA solution (0.5 mL with 5% $H_2O$). After 1 h stirring at 0° C., the reaction mixture was neutralized by saturated aqueous sodium carbonate solution under stirring. The mixture was mixed with acetonitrile and water to get a clear solution, which was used for the purification by HPLC with 10-70% methanol in $H_2O+0.5\%$ $NH_4HCO_3$ to give 12 as white solids (6.6 mg, yield: 39%): $^1H$ NMR (500 MHz, Methanol-$d_4$) δ 8.00 (s, 1H), 7.08 (t, J=7.8 Hz, 1H), 6.98 (s, 1H), 6.92 (d, J=7.4 Hz, 1H), 6.66 (d, J=8.2 Hz, 1H), 6.24 (d, J=3.3 Hz, 1H), 4.66-4.58 (m, 2H), 4.37 (td, J=6.0, 3.5 Hz, 1H), 4.27 (dd, J=10.8, 3.6 Hz, 1H), 4.18-4.08 (m, 3H), 3.94 (t, J=6.6 Hz, 2H), 2.88 (d, J=19.8 Hz, 2H), 1.77 (dt, J=13.0, 5.8 Hz, 4H), 1.53 (q, J=5.8 Hz, 4H), 1.45 (q, J=6.3 Hz, 2H). $^{31}P$ NMR (203 MHz, Methanol-$d_4$) δ 18.46 (s). MS (ESI): m/z=580 [M+1].

Biological Assays

The present invention will be further described with reference to the following test examples, but the examples should not be considered as limiting the scope of the invention.

Test Example 1, Test of the Compounds of the Present Invention for their Inhibition on CD73 Enzyme Activity In Vitro CD73 enzyme, an ecto-5'-Nucleotidase, converts extracellular nucleoside-5'-monophosphates to nucleosides, with AMP or CMP as the preferred substrate. In this assay, recombinant human CD73 expressed from a Chinese hamster ovary cell line (R&D Systems) was used to convert cytidine monophosphate (CMP) to cytidine and phosphate. Before adding substrate, CD73 enzyme was pre-incubated with compounds for 2 hours. The amount of phosphate was then measured by Malachite Green Phosphate Detection Kit. The experimental method is summarized as follows:

I. Experimental Materials and Equipment

1. Malachite green phosphate detection kit (R & D Systems, Cat #, DY996)
2. Recombinant human 5'-nucleotidase (CD73) (R & D Systems, Cat #, 5795-EN)
3. HEPES buffer (Gibco, Cat #, 15630-080)
4. CMP (Sigma, Cat #, C1006)

5. DMSO (Fisher Chemical, Cat #, D128-1)

6. NaCl 5M (Boston Bioproducts, Cat #, BM-244)

7. 384-well plate (Fisher, Cat #, 5795-EN)

8. TECAN plate reader (TECAN)

II. Experimental Procedure

Compounds are first dissolved in DMSO to 10 mM as a stock solution. When determining the $IC_{50}$ of the compound, prepare 3-fold serial dilutions with a highest concentration of 125 μM for a total of 12 concentration points and ensure each dilution containing equal amount of DMSO. In each well of 384-well plate, 0.34 nM of recombinant human 5'-nucleotidase (CD73) was pre-incubated at 37° C. for 2 hours with the compounds tested in assay buffer containing 20 mM HEPES buffer (pH 7.4), 137 mM NaCl, 0.001% Tween 20. The final reaction volume of the reaction in each well was 12 μL. The highest concentration of compound was 125 μM and the DMSO concentration was 1.25%. After pre-incubation, 3 μL of CMP dissolved in assay buffer was added to each reaction. The final CMP concentration was 45 μM. The reaction was incubated at 37° C. for 15 minutes. Then 3 μL of Malachite Green Reagent A was added to each reaction. Spin the plate briefly in centrifuge for 30 seconds. After incubation for additional 10 minutes at room temperature, 3 μL of malachite green Reagent B was added to each reaction. Spin the plate briefly in centrifuge for 30 seconds. After 20 minutes of incubation at room temperature, the signal was read on a TECAN reader at $OD_{620}$. The reaction containing CD73 enzyme, substrate CMP and DMSO (no compound) is used as an assay positive control while the reaction containing substrate CMP and DMSO without the CD73 enzyme as an assay negative control. $IC_{50}$ values were calculated by plotting the logarithm of the compound concentration and the percent inhibition using the appropriate program in GraphPad Prism.

The biochemical inhibitions of CD73 enzymatic activities by the compounds of the present invention were determined by the assay described above, and the resulting $IC_{50}$ values are shown in Table 1.

TABLE 1

$IC_{50}$ values of biochemical inhibition of CD73 enzymatic activity of the compounds of the invention

| Example number | $IC_{50}$ (nM) |
| --- | --- |
| 1 | 0.11 |
| 2 | 0.013 |
| 3 | 2.1 |
| 4 | 710 |
| 5 | 0.074 |
| 6 | 0.25 |
| 7 | 0.13 |
| 8 | 270 |
| 9 | 8.5 |
| 10 | 7.6 |
| 11 | 0.9 |
| 12 | 300 |

Conclusion: The compounds of the present invention have a significant inhibitory effect on CD73 enzyme activity in vitro.

Test Example 2 Determination of Compound of the Present Invention Modulates Cellular Immune Function by IFNγ Cytokine Production

I. EXPERIMENTAL MATERIALS AND EQUIPMENT

1. Cells: Cryopreserved human peripheral blood mononuclear cells (PBMCs) (Stemcell, Cat #70025). 1, 15 to 25 million cells per bottle
2. Lymphocyte culture medium (Zenbio, Cat #LYMPH-1)
3. TexMACS medium (Miltenyi, Cat #130-097-196)
4. CD3 and CD28 antibody beads (Fisher Scientific, Cat #1 161D)
5. HTRF human IFNγ Cytokine kit (Cisbio, human IFNγ Cat #62HIFNGPEH)
6. PHERAstar FSX Multilabel Reader (BMG Labtech)

II. EXPERIMENTAL PROCEDURE

Lymphocyte medium and TexMACS medium were incubated in a water bath at 37° C. 10 mL of incubated lymphocyte medium was added to a 50 mL conical tube. The cells were quickly thawed in a 37° C. water bath and transferred to a 50 ml tube and the tube gently swirled. The cell suspension was centrifuged at 1100 rpm for 10 minutes at room temperature. The supernatant was removed, and the cell pellet gently resuspended in 10 mL of TexMACS medium. The cells were counted to make $5 \times 10^5$ cells/ml. 100 μL of $5 \times 10^5$ cells/ml of PBMCs seeds, inserted into a 96-well plate (cell density of 50,000 cells/well), and the most outer edge wells of the 96-well plate were filled with water and were not used for the test. To mimic tumor microenvironment in human PBMC from normal donor and measure inhibition activity of the compound against CD73 enzyme, the CD73 substrate AMP was added to human PBMC cell culture in order to generate more adenosine via CD73 enzyme. Added 50 μL of 200 μM AMP (Sigma A2252) to each of the other wells. The final AMP concentration was 50 μM. Compounds were diluted to 40 μM in TexMACS media. In addition to the "AMP only" wells, 50 μL of compound was added to each well. The final compound concentration was 10 μM in 0.1% DMSO. A 0.4% DMSO was prepared in TexMACS medium and 50 μL was added to AMP control wells. Gently tapped the board to mix it evenly. After 2 hours of incubation with 5% $CO_2$ at 37° C., CD3 and CD28 antibody beads were washed twice with TexMACS media and a magnet rack. Added 2 μL of CD3 and CD28 antibody beads to each well. The final antibody beads and cells ratio was 1:1. Pipetted cells and antibody beads several times to homogenize. Incubated at 37° C. for 72 hours in a 5% $CO_2$ humidified incubator. After incubation, the cells were spun (1000 rpm for 5 minutes), 90 μL of cell culture supernatant was carefully collected, and the culture supernatant was stored with HTRF IFNγ cytokine reagent and assayed immediately or frozen at −80° C. In a sample diluted in TexMACS medium (25 and 100 times), 12.8 μL of sample was added to each well of a 384-well plate (Proxiplate-384plus). The IFN Cryptate was mixed with XL (1:1) and 3.2 μL of the mixed solution was added to each well in the plate. Swirl swiftly spinned down. Protected from light at room temperature. Read the values of 665 nm and 620 nm on a PHERAstar FSX Multilabel Reader.

III. DATA ANALYSIS

Calculated ratio=(signal at 665 nm/signal at 620 nm)×$10^4$, which reflected the "raw signal". Delta Ratio reflected the specific signal. Delta Ratio=Standard or Sample Ratio—Standard 0 Ratio, where Standard 0 was negative control and was used as an internal assay control. Drawed a standard curve using ratios with a quadratic curve fit method following vendor's instruction. The concentration of IFNγ cytokine of each sample corresponding to the standard curve was calculated. Response rate of IFNγ cytokines by a compound (fold)=(sample-AMP only)/(DMSO-AMP only), where sample=IFNγ produced by 10 μM compound in 0.1% DMOS and 50 μM AMP; DMSO=IFNγ produced by 0.1% DMSO (vehicle control) and 50 μM AMP; AMP only=IFNγ produced by 50 μM AMP (as background).

The production of IFNγ cytokines by the compounds of the present invention was measured by the above test. The compounds at 10 μM were able to produce IFNγ cytokines 4.1 folds for 1 and 4.3 folds for 2 as compared to vehicle control (DMSO), respectively.

IV. CONCLUSION

The compounds of the invention can stimulate the production of IFNγ cytokines and thus have a significant modulating effect on the cellular immune functions.

The foregoing embodiments and examples are provided for illustration only and are not intended to limit the scope of the invention. Various changes and modifications to the disclosed embodiments will be apparent to those skilled in the art based on the present disclosure, and such changes and modifications may be made without departure from the spirit and scope of the present invention. All literature and references cited are incorporated herein by reference in their entireties.

What is claimed is:
1. A compound of formula (I):

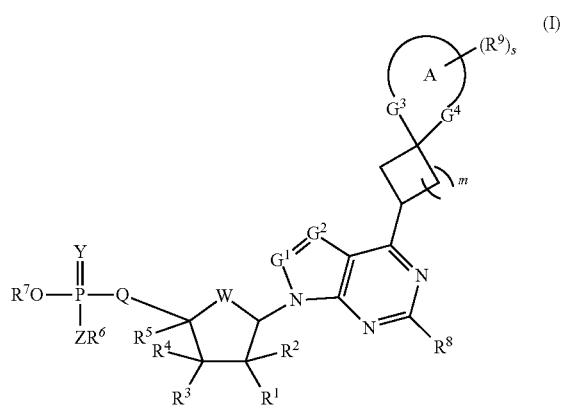

or a tautomer, or a pharmaceutically acceptable salt or solvate thereof, wherein:
Y is O or S;
Z is O or NH;
W is selected from the group consisting of O, S, NH, $NR^a$ and $C(R^b)_2$, wherein $R^a$ is alkyl, and $R^b$ at each occurrence is independently selected from the group consisting of hydrogen, halogen, alkyl, and alkenyl;
$G^1$ and $G^2$ are each independently N or $CR^c$, wherein $R^c$ is selected from the group consisting of hydrogen, halogen, alkyl, alkoxy, hydroxy, amino, nitro, cyano, cycloalkyl, heterocyclyl, aryl, and heteroaryl;
$G^3$ and $G^4$ are each independently selected from the group consisting of C, CH, $CH_2$, N, NH, O, S, and $SO_2$;

Q is selected from the group consisting of —$CH_2$—O—$C(R^s)(R^t)$—, —$CH_2$—$N(R^m)$—$C(R^s)(R^t)$—, —$CH_2$—S—$C(R^s)(R^t)$—, —$CH_2$—$S(O)_2$—$C(R^s)(R^t)$—, —phenylene—O—$C(R^s)(R^t)$—, —$CH_2$—phenylene—O—$C(R^s)(R^t)$—, —$CH_2$-heterocyclylene-, —$C(R^m)(R^n)$—, —$CH_2$—$C(R^m)(R^n)$—$C(R^s)(R^t)$—, —$C(R^s)$=$C(R^t)$—, —$C(R^m)(R^n)$—$C(R^s)(R^t)$—, —$C(R^m)(R^n)$—$C(R^s)$=$C(R^t)$—, and —$C(R^s)$=$C(R^t)$—$C(R^m)(R^n)$);
$R^s$, $R^t$, $R^m$ and $R^n$ are each independently selected from the group consisting of H, D, halogen, alkyl, alkoxy, haloalkyl, haloalkoxy, hydroxy, hydroxyalkyl, and amino;
or $R^s$ and $R^t$ in any —$C(R^s)(R^t)$— together form oxo;
or $R^m$ and $R^n$ together form oxo;
ring A is selected from the group consisting of $C_{5-8}$cycloalkyl, 5 to 8-membered heterocyclyl, aryl fused $C_{5-8}$cycloalkyl, heteroaryl fused $C_{5-8}$cycloalkyl, aryl fused 5 to 8-membered heterocyclyl, and heteroaryl fused 5 to 8-membered heterocyclyl;
$R^1$, $R^2$, $R^3$ and $R^4$ are each independently selected from the group consisting of hydroxy, hydrogen, halogen, alkyl, alkoxy, haloalkyl, hydroxyalkyl, cyano, amino, azide group, and $OR^{10}$;
or $R^1$ and $R^2$ together with the carbon atom to which they are attached form a cycloalkyl or heterocyclyl, wherein the heterocyclyl contains 1 to 2 heteroatoms independently selected from the group consisting of N, O, and S; and wherein the cycloalkyl and heterocyclyl are each optionally substituted by one or more substituents independently selected from the group consisting of halogen, alkyl, alkoxy, haloalkyl, haloalkoxy, hydroxy, hydroxyalkyl, cyano, amino, nitro, cycloalkyl, and heterocyclyl;
$R^5$ is selected from the group consisting of hydrogen, halogen, alkyl, alkenyl, alkynyl, alkoxy, haloalkyl, haloalkoxy, hydroxy, hydroxyalkyl, cyano, amino, nitro, and azide;
$R^6$ and $R^7$ are each independently selected from the group consisting of hydrogen, alkyl, aryl, —$C(R^m)(R^n)$—aryl, —$C(R^m)(R^n)$—O—$C(O)OR^d$, —$C(R^m)(R^n)$—O—$C(O)R^d$, —$C(R^m)(R^n)C(O)OR^d$, cycloalkyl, heterocyclic, aryl, and heteroaryl, wherein the alkyl is optionally substituted by one or more substituents independently selected from the group consisting of cycloalkyl, heterocyclyl, aryl, and heteroaryl; optionally, $R^6$ and $R^7$ together form a 5- to 6-membered heterocyclic ring;
$R^d$ is selected from the group consisting of hydrogen, alkyl, and alkoxy;
$R^8$ is selected from the group consisting of hydrogen, halogen, alkyl, alkenyl, alkynyl, alkoxy, haloalkyl, haloalkoxy, hydroxy, hydroxyalkyl, cyano, amino, nitro, azide, cycloalkyl, and heterocyclyl;
$R^9$ is selected from the group consisting of hydrogen, halogen, alkyl, alkenyl, alkynyl, alkoxy, haloalkyl, haloalkoxy, hydroxy, hydroxyalkyl, cyano, amino, nitro, azide, cycloalkyl, and heterocyclyl;
$R^{10}$ is selected from the group consisting of —$C(O)R^{11}$, —$C(O)OR^{11}$, —$S(O)_2R^{11}$, and —$P(O)(OR^6)(OR^7)$;
$R^{11}$ is selected from the group consisting of hydrogen, halogen, alkyl, haloalkyl, hydroxyl, and hydroxyalkyl;
m is 1, 2, or 3; and
s is 0, 1, 2, 3, or 4.

2. The compound of claim 1, being a compound of formula (II):

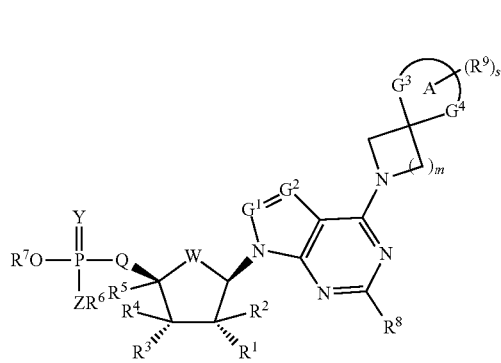

(II)

or a tautomer, or a pharmaceutically acceptable salt or solvate thereof, wherein:

Z, Y, W, Q, $G^1$, $G^2$, $G^3$, $G^4$, ring A, $R^1$ to $R^9$, m, and s are as defined in claim 1.

3. The compound of claim 1, being a compound of formula (III):

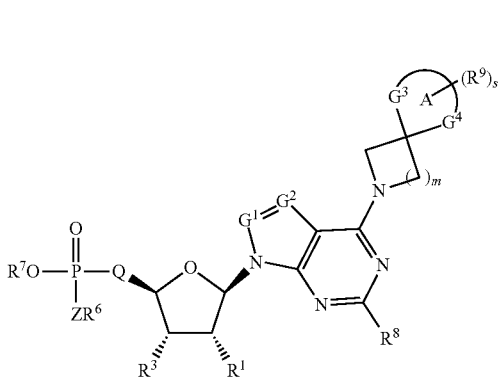

(III)

or a tautomer, or a pharmaceutically acceptable salt or solvate thereof, wherein:

Z, Q, $G^1$, $G^2$, $G^3$, $G^4$, ring A, $R^1$, $R^3$, $R^6$ to $R^9$, m, and s are as defined in claim 1.

4. The compound according to claim 1, or a tautomer, or a pharmaceutically acceptable salt or solvate thereof, wherein Q is selected from the group consisting of —$CH_2$—O—C($R^s$)($R^t$)—, —$CH_2$—NH—C($R^s$)($R^t$)—, —$CH_2$—S—C($R^s$)($R^t$)—, —$CH_2S(O)_2$—C($R^s$)($R^t$)—, —phenylene—O—C($R^s$)($R^t$)—, —$CH_2$—phenylene—O—C($R^s$)($R^t$)—, and —$CH_2$—heterocyclylene—;

and wherein $R^s$ and $R^t$ are as defined in claim 1.

5. The compound according to claim 1, or a tautomer, or a pharmaceutically acceptable salt or solvate thereof, wherein $R^2$ and $R^4$ are each hydrogen; and $R^1$ and $R^3$ are each independently selected from the group consisting of hydroxy, hydrogen, halogen, alkyl, alkoxy, haloalkyl, haloalkoxy, and hydroxyalkyl.

6. The compound according to claim 1, or a tautomer, or a pharmaceutically acceptable salt or solvate thereof, being a compound of formula (IV):

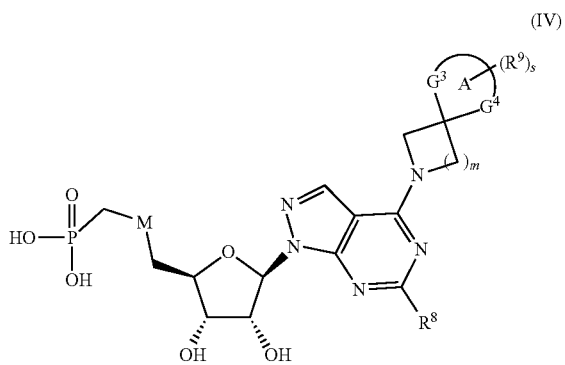

(IV)

or a tautomer, a pharmaceutically acceptable salt or solvate thereof, wherein:

M is selected from the group consisting of O, S, $SO_2$, NH, and —phenylene—O; and ring A, $G^3$, $G^4$, $R^8$, $R^9$, m, and s are as defined in claim 1.

7. The compound according to claim 1, or a tautomer, or a pharmaceutically acceptable salt or solvate thereof, wherein

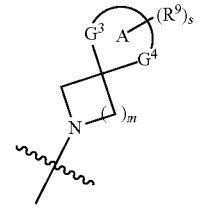

is selected from the group consisting of

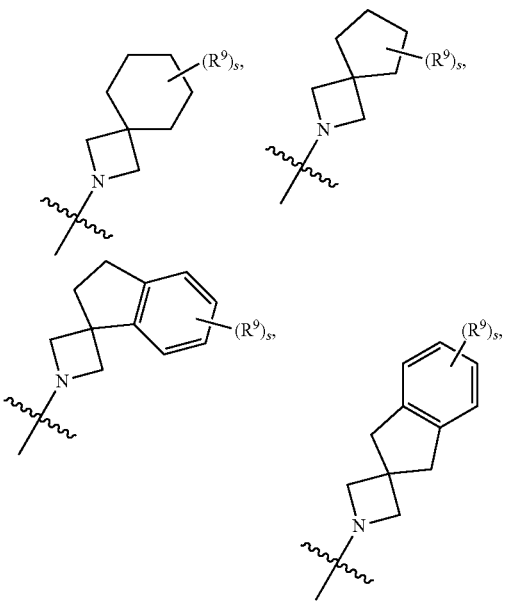

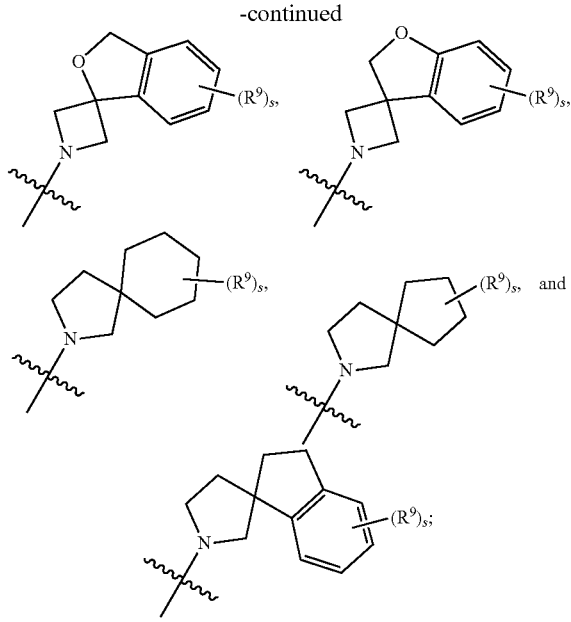

and R⁹ and s are as defined in claim 1.

8. The compound according to claim 1, or a tautomer, or a pharmaceutically acceptable salt or solvate thereof, wherein R⁶ and R⁷ are each independently selected from the group consisting of hydrogen, alkyl, and —C(R'''R'')—O—C(O)OR$^d$, wherein R''', R'' and R$^d$ are as defined in claim 1.

9. The compound according to claim 1, or a tautomer, or a pharmaceutically acceptable salt or solvate thereof, wherein R⁸ is selected from the group consisting of hydrogen, halogen, alkyl, alkoxy, haloalkyl, and haloalkoxy.

10. The compound according to claim 1, or a tautomer, or a pharmaceutically acceptable salt or solvate thereof, wherein R⁹ is selected from the group consisting of hydrogen, halogen, alkyl, alkoxy, haloalkyl, and haloalkoxy.

11. The compound of claim 1, or a tautomer, or a pharmaceutically acceptable salt or solvate thereof, being a compound of formula (V):

wherein:

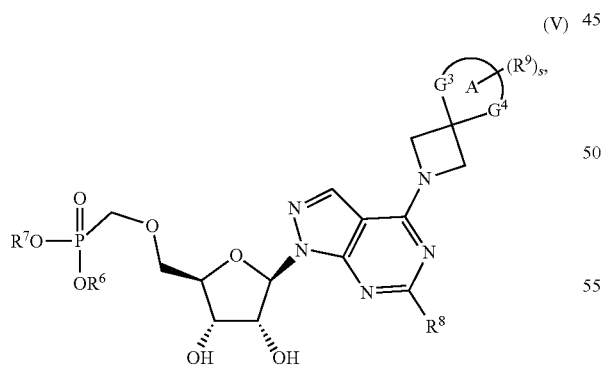
(V)

R⁶ and R⁷ are each independently selected from the group consisting of hydrogen, C₁-C₆ alkyl, C₆-C₁₀ aryl, —C(R'''R'')—aryl, —C(R'''R'')—O—C(O)OR$^d$, and —C(R'''R'')—O—C(O)R$^d$, wherein the C₁-C₆ alkyl is optionally substituted by one or more groups selected from the group consisting of C₃-C₆ cycloalkyl, 5- to 10-membered heterocyclyl, C₆-C₁₀ aryl, and 5- to 10-membered heteroaryl;

R''' and R'' are each independently selected from the group consisting of H, D, halogen, C₁-C₄ alkyl, C₁-C₄ alkoxy, C₁-C₄ haloalkyl, and C₁-C₄ haloalkoxy;

R$^d$ is C₁-C₆ alkyl;

R⁸ is selected from the group consisting of hydrogen, halogen, and C₁-C₄ alkyl;

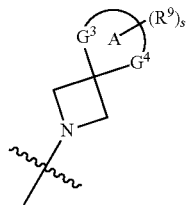

is selected from the group consisting of

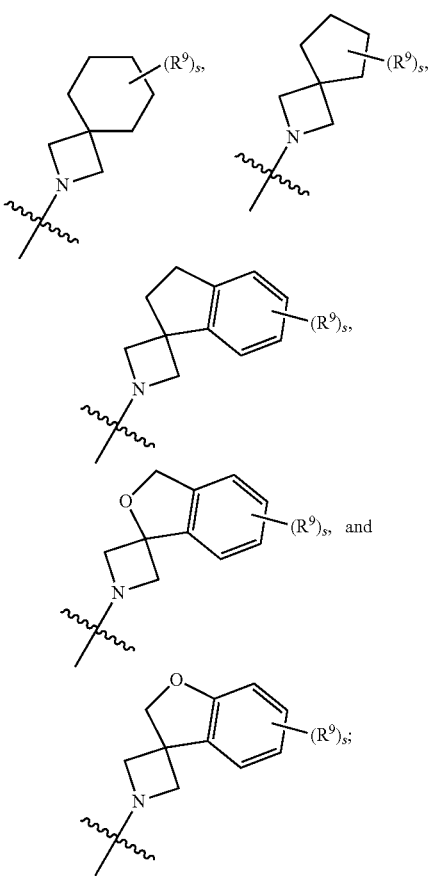

s is 0, 1, or 2; and

R⁹ at each occurrence is independently selected from the group consisting of halogen, C₁-C₄ alkyl, C₁-C₄ alkoxy, C₁-C₄ haloalkyl, and C₁-C₄ haloalkoxy.

12. The compound of claim 11, or a tautomer, or a pharmaceutically acceptable salt or solvate thereof, wherein:

R⁶ and R⁷ are each independently selected from the group consisting of hydrogen, C₁-C₄ alkyl, phenyl, —CH(R''')—O—C(O)OR$^d$, and —CH(R''')—O—C(O)R$^d$;

R''' is H, D, or C₁-C₄ alkyl;

R$^d$ is C₁-C₆ alkyl;

R⁸ is hydrogen or halogen;

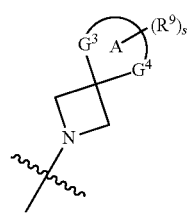
is selected from the group consisting of
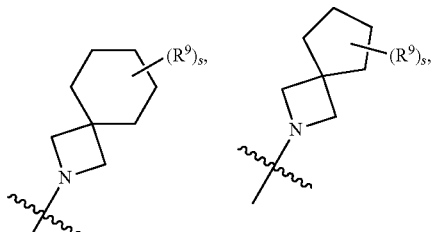
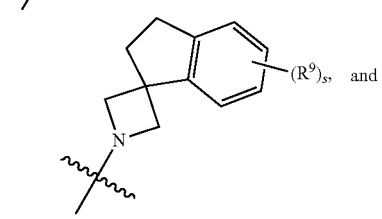
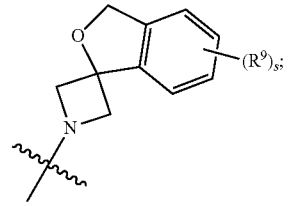
s is 0, 1, or 2; and
R$^9$ at each occurrence is independently selected from the group consisting of halogen, C$_1$-C$_4$ alkyl, and C$_1$-C$_4$ alkoxy.
13. The compound according to claim 1, or a tautomer, or a pharmaceutically acceptable salt or solvate thereof, wherein the compound is selected from the group consisting of:
1
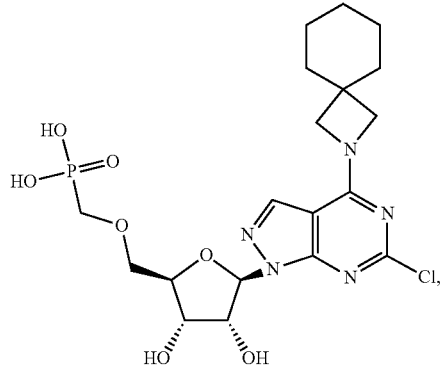
2
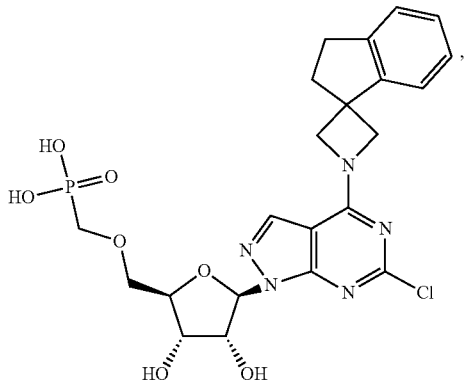
3
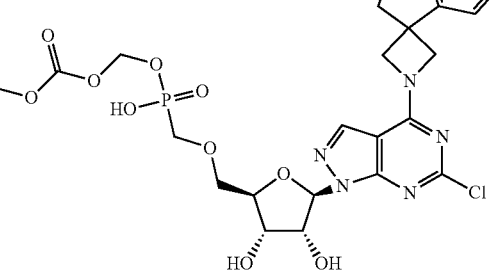
4
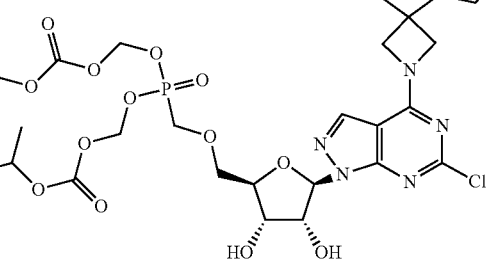
5
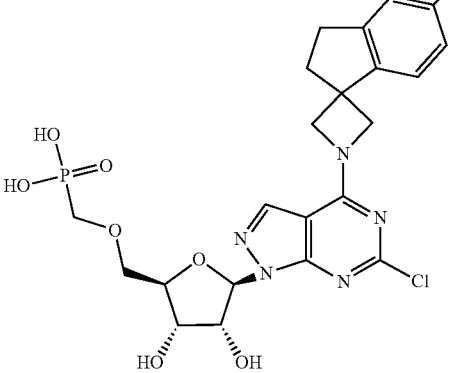

87
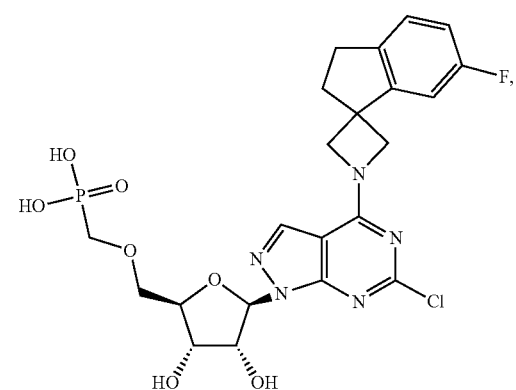
6
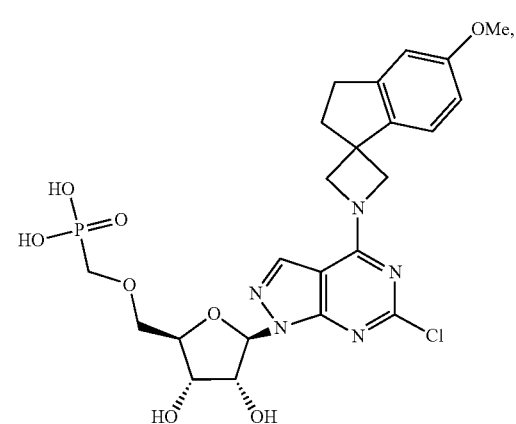
7
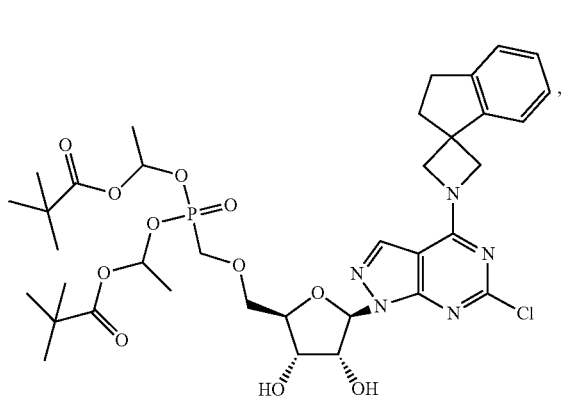
8
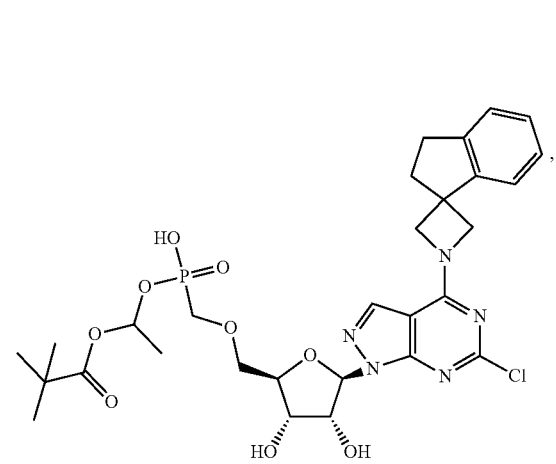
9
88
10
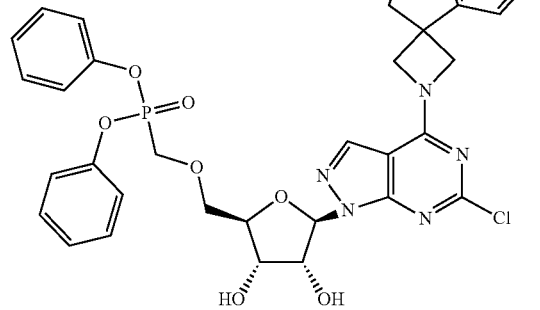
11
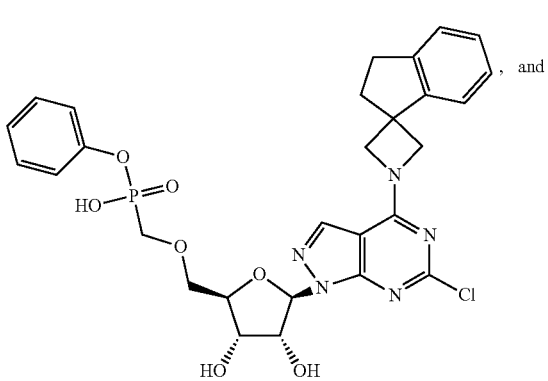
12
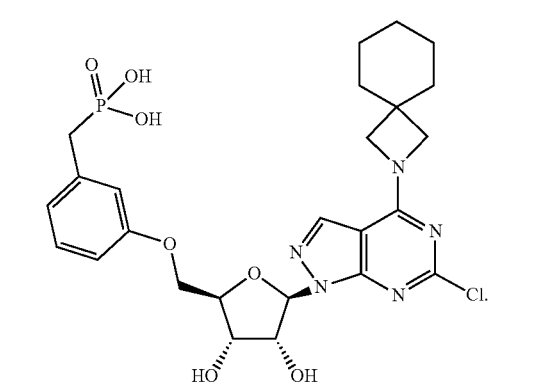
14. A compound of formula (IA):
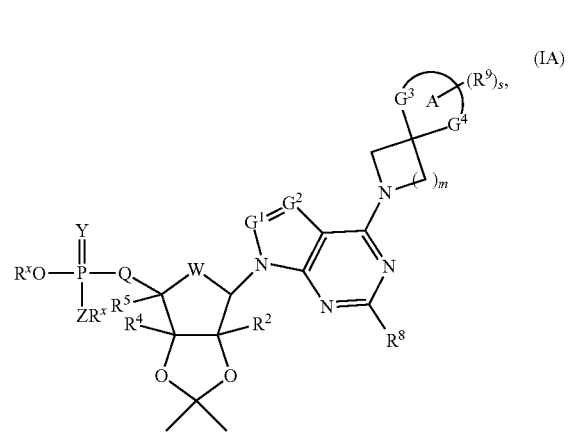
(IA)

or a tautomer, or a pharmaceutically acceptable salt or solvate thereof, wherein:

Z is O;

$R^x$ is alkyl; and

Y, W, Q, $G^1$, $G^2$, $G^3$, $G^4$, ring A, $R^2$, $R^4$, $R^5$, $R^8$, $R^9$, m, and s are as defined in claim 1.

15. The compound of claim 14, being a compound of formula (IVA):

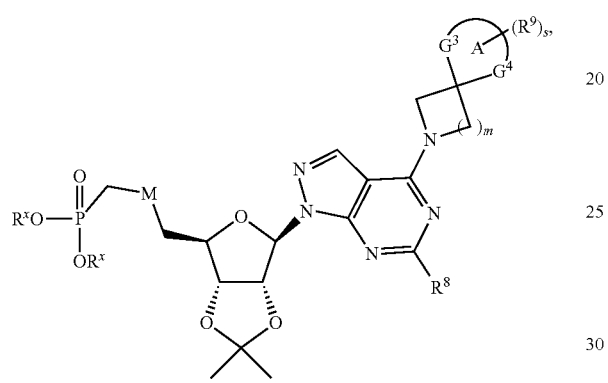

(IVA)

or a tautomer, or a pharmaceutically acceptable salt or solvate thereof, wherein:

$R^x$ is alkyl;

M is O; and ring A, $G^3$, $G^4$, $R^8$, $R^9$, m, and s are as defined in claim 14.

16. The compound of claim 14, wherein the compound is selected from the group consisting of:

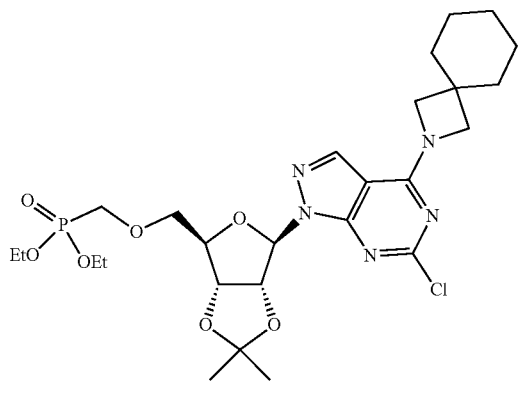

1f

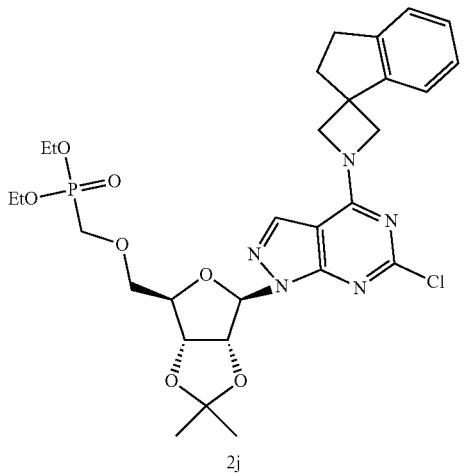

2j

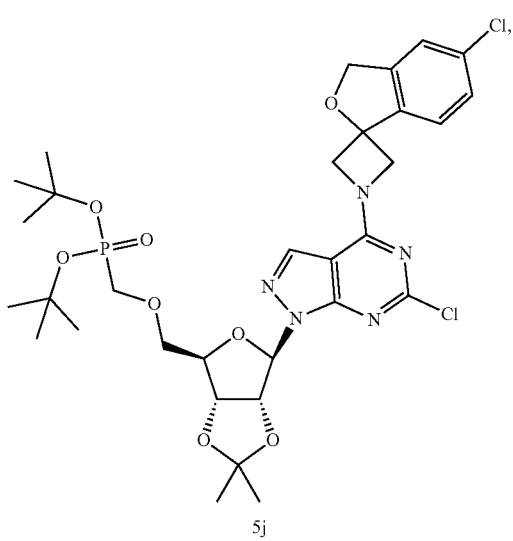

5j

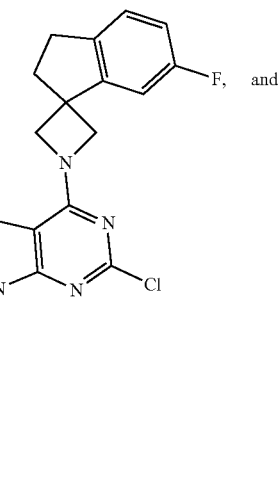

and

6n

-continued

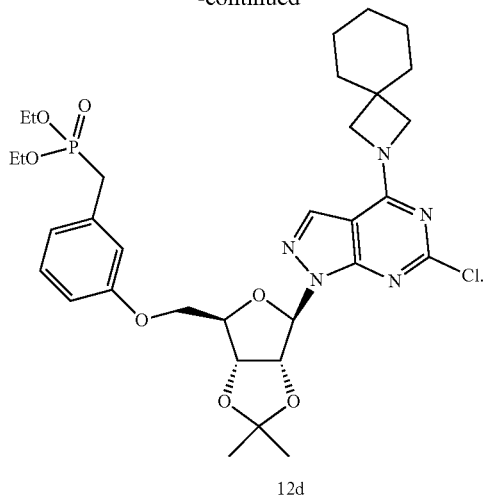

12d

17. A process for preparing the compound of formula (I) according to claim 1, comprising a step of:

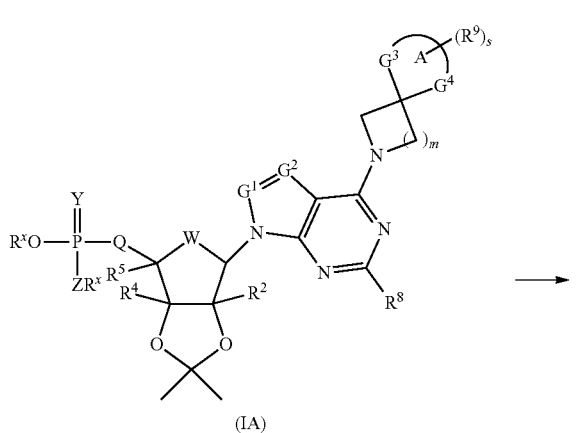

reacting a compound of formula (IA) to remove the protecting groups $R^x$ and acetal to obtain a compound of formula (I);
wherein:
$R^x$ is alkyl;
Z is O;
$R^6$ and $R^7$ are each hydrogen;
$R^1$ and $R^3$ are each hydroxy; and
Y, W, Q, $G^1$, $G^2$, $G^3$, $G^4$, ring A, $R^2$, $R^4$, $R^5$, $R^8$, $R^9$, m, and s are as defined in claim 1.

18. A process for preparing the compound of formula (IV) according to claim 6, comprising a step of:

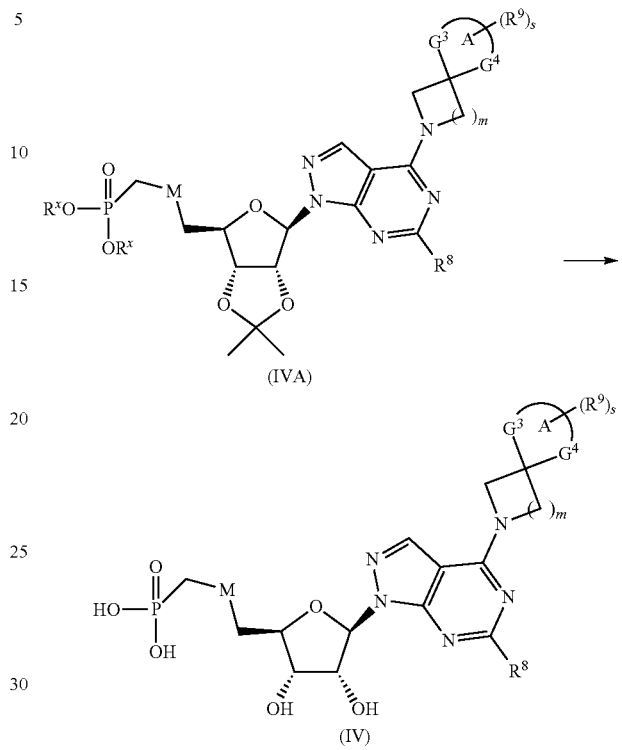

reacting a compound of formula (IVA) to remove the protecting groups $R^x$ and acetal to obtain the compound of formula (IV);
wherein:
$R^x$ is alkyl;
M is O; and
ring A, $G^3$, $G^4$, $R^8$, $R^9$, m, and s are as defined in claim 6.

19. A pharmaceutical composition comprising a therapeutically effective amount of a compound according to claim 1, or a pharmaceutically acceptable salt or solvate thereof, and one or more pharmaceutically acceptable carriers, diluents and/or other excipients.

20. A method for inhibiting CD73, comprising contacting a biological sample containing CD73 with a compound according to claim 1, or a pharmaceutically acceptable salt or solvate thereof.

21. A method for treating a disease or disorder, comprising administering to a subject in need thereof a therapeutically effective amount of a compound according to claim 1, or a pharmaceutically acceptable salt or solvate thereof, wherein the disease or disorder is selected from the group consisting of tumor, cancer, immune-related diseases, inflammatory-related diseases, nervous system, neurodegenerative and central nervous system diseases, depression, Parkinson's disease, ischemic diseases of the brain and heart, sleep disorders, endometriosis, polycythemia vera, and fibrosis.

22. A method for treating a disease or condition mediated by CD73, comprising administering to a subject in need thereof a therapeutically effective amount of a compound according to claim 1, or a pharmaceutically acceptable salt or solvate thereof, wherein the disease or condition is selected from the group consisting of tumor, cancer, immune-related diseases, inflammatory-related diseases, nervous system, neurodegenerative and central nervous system diseases, depression, Parkinson's disease, ischemic diseases of the brain and heart, sleep disorders, endometriosis, polycythemia vera, and fibrosis.

23. The method according to claim 22, wherein cancer is selected from the group consisting of melanoma, brain tumor, esophageal cancer, gastric cancer, liver cancer, pancreatic cancer, colorectal cancer, lung cancer, kidney cancer, breast cancer, ovarian cancer, metrocarcinoma, prostate cancer, skin cancer, neuroblastoma, sarcoma, osteochondroma, osteoma, osteosarcoma, seminoma, testicular tumor, uterine cancer, head and neck cancer, multiple myeloma, lymphoma, leukemia, thyroid tumor, ureteral tumor, bladder cancer, gallbladder cancer, cholangiocarcinoma, chorionic epithelial cancer, and pediatric tumor.

* * * * *